United States Patent
Scher et al.

(10) Patent No.: US 8,062,967 B1
(45) Date of Patent: Nov. 22, 2011

(54) PROCESS FOR GROUP III-V SEMICONDUCTOR NANOSTRUCTURE SYNTHESIS AND COMPOSITIONS MADE USING SAME

(75) Inventors: Erik C. Scher, San Francisco, CA (US); Mihai A. Buretea, San Francisco, CA (US); William P. Freeman, San Mateo, CA (US); Joel Gamoras, Vallejo, CA (US); Baixin Qian, Sunnyvale, CA (US); Jeffery A. Whiteford, Belmont, CA (US)

(73) Assignee: Nanosys, Inc., Palo Alto, CA (US)

( * ) Notice: Subject to any disclaimer, the term of this patent is extended or adjusted under 35 U.S.C. 154(b) by 0 days.

(21) Appl. No.: 12/475,772

(22) Filed: Jun. 1, 2009

Related U.S. Application Data

(62) Division of application No. 11/178,257, filed on Jul. 8, 2005, now Pat. No. 7,557,028.

(60) Provisional application No. 60/628,455, filed on Nov. 15, 2004, provisional application No. 60/591,987, filed on Jul. 28, 2004.

(51) Int. Cl.
*H01L 21/3205* (2006.01)

(52) U.S. Cl. ......... 438/604; 257/E33.023; 257/E29.089; 977/773; 977/815; 977/816; 977/818; 977/819

(58) Field of Classification Search ........... 257/E33.023, 257/E33.049, E29.089, E29.144; 438/604; 977/754, 762, 773, 815, 816, 818, 819, 820, 977/821, 822, 823
See application file for complete search history.

(56) References Cited

U.S. PATENT DOCUMENTS

| | | | |
|---|---|---|---|
| 5,260,957 A | 11/1993 | Hakimi et al. |
| 5,262,357 A | 11/1993 | Alivisatos et al. |
| 5,505,928 A | 4/1996 | Alivisatos et al. |
| 5,537,000 A | 7/1996 | Alivisatos et al. |
| 5,751,018 A | 5/1998 | Alivisatos et al. |
| 5,990,479 A | 11/1999 | Weiss et al. |
| 6,207,229 B1 | 3/2001 | Bawendi et al. |
| 6,207,392 B1 | 3/2001 | Weiss et al. |
| 6,225,198 B1 | 5/2001 | Alivisatos et al. |
| 6,251,303 B1 | 6/2001 | Bawendi et al. |
| 6,306,610 B1 | 10/2001 | Bawendi et al. |

(Continued)

FOREIGN PATENT DOCUMENTS

WO 03054953 7/2003

(Continued)

OTHER PUBLICATIONS

Alivisatos, A.P. "Semiconductor clusters, nanocrystals, and quantum dots" Science (1996) 271:933-937.

(Continued)

*Primary Examiner* — Matthew Landau
*Assistant Examiner* — Colleen E Snow
(74) *Attorney, Agent, or Firm* — Andrew L. Filler

(57) ABSTRACT

Methods for producing nanostructures, particularly Group III-V semiconductor nanostructures, are provided. The methods include use of novel Group III and/or Group V precursors, novel surfactants, oxide acceptors, high temperature, and/or stable co-products. Related compositions are also described. Methods and compositions for producing Group III inorganic compounds that can be used as precursors for nanostructure synthesis are provided. Methods for increasing the yield of nanostructures from a synthesis reaction by removal of a vaporous by-product are also described.

33 Claims, 31 Drawing Sheets where X is a halogen atom or an acid moiety (e.g. phosphonate or carboxylate)

U.S. PATENT DOCUMENTS

| | | |
|---|---|---|
| 6,306,736 B1 | 10/2001 | Alivisatos et al. |
| 6,319,426 B1 | 11/2001 | Bawendi et al. |
| 6,322,901 B1 | 11/2001 | Bawendi et al. |
| 6,326,144 B1 | 12/2001 | Bawendi et al. |
| 6,423,551 B1 | 7/2002 | Weiss et al. |
| 6,426,513 B1 | 7/2002 | Bawendi et al. |
| 6,440,213 B1 | 8/2002 | Alivisatos et al. |
| 6,444,143 B2 | 9/2002 | Bawendi et al. |
| 6,501,091 B1 | 12/2002 | Bawendi et al. |
| 6,576,291 B2 | 6/2003 | Bawendi et al. |
| 6,602,671 B1 | 8/2003 | Bawendi et al. |
| 6,607,829 B1 | 8/2003 | Bawendi et al. |
| 6,617,583 B1 | 9/2003 | Bawendi et al. |
| 6,696,299 B1 | 2/2004 | Empedocles et al. |
| 6,699,723 B1 | 3/2004 | Weiss et al. |
| 6,727,065 B2 | 4/2004 | Weiss et al. |
| 6,774,361 B2 | 8/2004 | Bawendi et al. |
| 6,788,453 B2 | 9/2004 | Banin et al. |
| 6,803,719 B1 | 10/2004 | Miller et al. |
| 6,819,692 B2 | 11/2004 | Klimov et al. |
| 6,821,337 B2 | 11/2004 | Bawendi et al. |
| 6,855,202 B2 | 2/2005 | Alivisatos et al. |
| 6,855,551 B2 | 2/2005 | Bawendi et al. |
| 6,861,155 B2 | 3/2005 | Bawendi et al. |
| 6,864,626 B1 | 3/2005 | Weiss et al. |
| 6,884,478 B2 | 4/2005 | Alivisatos et al. |
| 6,890,777 B2 | 5/2005 | Bawendi et al. |
| 6,914,265 B2 | 7/2005 | Bawendi et al. |
| 6,918,946 B2 | 7/2005 | Korgel et al. |
| 6,921,496 B2 | 7/2005 | Anderson et al. |
| 6,927,069 B2 | 8/2005 | Weiss et al. |
| 6,984,369 B1 | 1/2006 | Alivisatos et al. |
| 7,049,148 B2 | 5/2006 | Bawendi et al. |
| 2003/0010987 A1 | 1/2003 | Banin et al. |
| 2003/0142944 A1 | 7/2003 | Sundar et al. |
| 2003/0145779 A1* | 8/2003 | Alivisatos et al. ............... 117/2 |
| 2003/0226498 A1 | 12/2003 | Alivisatos et al. |
| 2004/0004982 A1 | 1/2004 | Eisler et al. |
| 2004/0017834 A1 | 1/2004 | Sundar et al. |
| 2004/0023010 A1 | 2/2004 | Bulovic et al. |
| 2006/0060862 A1 | 3/2006 | Bawendi et al. |
| 2006/0068154 A1 | 3/2006 | Parce |
| 2006/0110279 A1* | 5/2006 | Han et al. ...................... 420/523 |

FOREIGN PATENT DOCUMENTS

| | | |
|---|---|---|
| WO | 2005022120 | 3/2005 |
| WO | 2005023923 | 3/2005 |

OTHER PUBLICATIONS

Beachley, O.T. Jr. et al. "Reagents based on cyclopentadienyl derivatives of the group 14 elements for the synthesis of indium(I) derivatives. Crystal and molecular structure of In(C5H4SiMe3)" Organometallics (1990) 9:2488-2492.

Beachley, O.T. Jr. et al. "Chemistry of In(C5H5)3 and some heteroleptic organoindium (III) derivatives. Crystal and molecular structures of In(C5H5)3, In(C5H5)3In-PPh3, Me3CCH2)2In(C5H5)" Organometallics (2002) 21:4632-4640.

Beletskaya, I.P. et al. "New approach to phosphinoalkynes based on Pd- and Ni-catalyzed cross-coupling of terminal alkynes with chlorophosphanes" Org. Lett (2003) 5(23):4309-4311.

Boeckman, R.K. Jr. et al. "Cyclic vinyl ether carbanions I: synthetic equivalents of β-acylvinyl and substituted acyl anions" Tet Lett (1977) 48:4187-4190.

Boeckman, R.K. Jr. et al. "Cyclic vinyl ether carbanions II: preparation and applications of the synthesis of carbonyl compounds" Tetrahedron (1981) 37(23):3997-4006.

Bradley, D.C et al. "A penta-indium oxo alkoxide cluster with a central 5-co-ordinate oxygen. Preparation and x-ray crystal structure of (InOPri)5(μ2-OPri)4(μ3-OPri)4(μ5-O)" J. Chem. Soc. Chem. Commun (1987) 18:1258-1259.

Bradley, D.C. et al. "Pentanuclear oxoalkoxide clusters of scandium, yttrium, indium and ytterbium, x-ray crystal structures of [M5(μ5-O)(μ3-OPri)4(μ2-Opri)4(OPri)5] (M=In, Yb)" Polyhedron (1990) 9(5):719-726.

Farina V. et al. "Large rate accelerations in the stille reaction with tri-2-furylphosphine and triphenylarsine as palladium ligands: mechanistic and synthetic implications" J. Am. Chem. Soc. (1991) 113:9585-9595.

Franks, S. et al. "The preparation and properties of tertiary phosphines and tertiary phosphine oxides with long alkyl chains" J. Chem. Soc. Perkin (1979) 1:3029-3033.

Guzelian, A.A. et al. "Colloidal chemical synthesis and characterization of InAs nanocrystal quantum dots" Appl. Phy. Lett (1996) 69(10): 1432-1434.

Guzelian, A.A. et al. "Synthesis of size-selected, surface passivated InP nanocrystals" J. Phys. Chem. (1996) 100:7212-7219.

Ji, H-L et al. "Scope and diastereoselectivity of intramolecular [4+2] diels-alder cycloadditions within the coordination sphere of [(η5-C5H5)Ru(DMPP)3-n(dienophile)n]PF6" Organometallics (1992) 11:1840-1855.

Kost, D. et al. "The barrier to carbon-phosphorus bond rotation in tribenzoylphosphine. An experimental reinvestigation" Tet Lett (1979) 22:1983-1986.

Lehmann, U. et al. "Palladium-catalyzed cross-coupling reactions between dihydrophyranylindium reagents and aryl halides. Synthesis of C-Arl glycols" Org. Lett (2003) 5(14):2405-2408.

MacDonell, G.D. et al. "The barrier to carbon-phosphorus bond rotation in triaroylphosphines" Tet Lett (1978) 10:857-860.

Manna, L. et al. "Shape control of colloidal semiconductor nanocrystals" J. Clus. Sci (2002) 13(4):521-532.

Miinea, L.A. et al. "Indium fluoroalkoxide compounds" Inorg. Chem. (1999) 38:4447-4454.

Murray, C.B. et al. "Synthesis and characterization of nearly monodisperse CdE (E = sulfur, selenium, tellurium) semiconductor nanocrystallites" J. Am. Chem. Soc. (1993) 115: 8706-8715.

Peng, X. et al. "Epitaxial growth of highly luminescent CdSe/CdS core/shell nanocrystals with photostability and electronic accessibility" J. Am. Chem. Soc. (1997) 119:7019-7029.

Peng, X. et al. "Shape control of CdSe nanocrystals" Nature (2000) 404:59-61.

Puntes, V.F. et al. "Colloidal nanocrystal shape and size control: The case of cobalt" Science (2001) 291:2115-2117.

Schiefer, M. et al. "Neutral and ionic aluminum, gallium, and indium compounds carrying two or three terminal ethynyl groups" Inorg. Chem. (2003) 42:4970-4976.

Son, S.U. et al., "Facile synthesis of various phosphine-stabilized monodisperse palladium nanoparticles through the understanding of coordinationi of chemistry of nanoparticles" Nano Lett (2004) 4(6):1147-1151.

Wells, R.L. et al. "Use of Tris(trimethylsilyl)arsine to prepare gallium arsenide and indium arsenide" Chem. of Mat. (1989) 1:4-6.

Yang, Y. et al., "Organic reactions in aqueous media, cyclopentadienylindium(I) as the first example of organoindium (I) reagent for carbon-carbon bond formation and the demonstration of one-pot tandem addition/intramolecular diels—alder reaction in aqueous media" J. Am. Chem. Soc. (2000) 122:402-403.

* cited by examiner

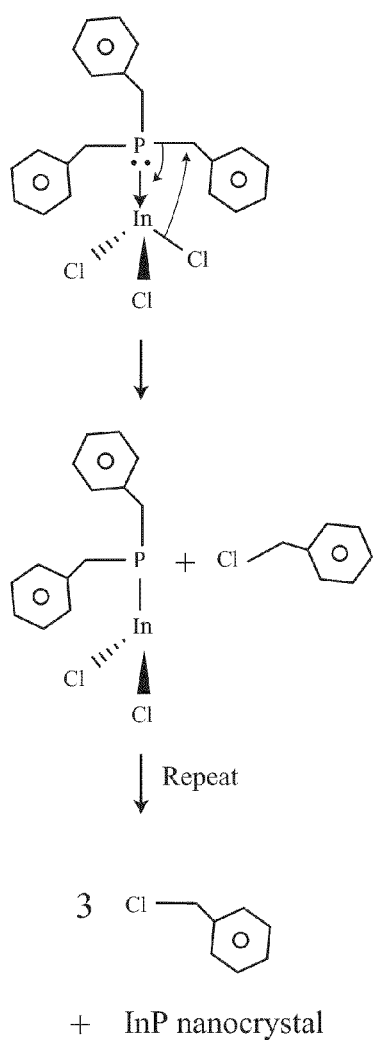
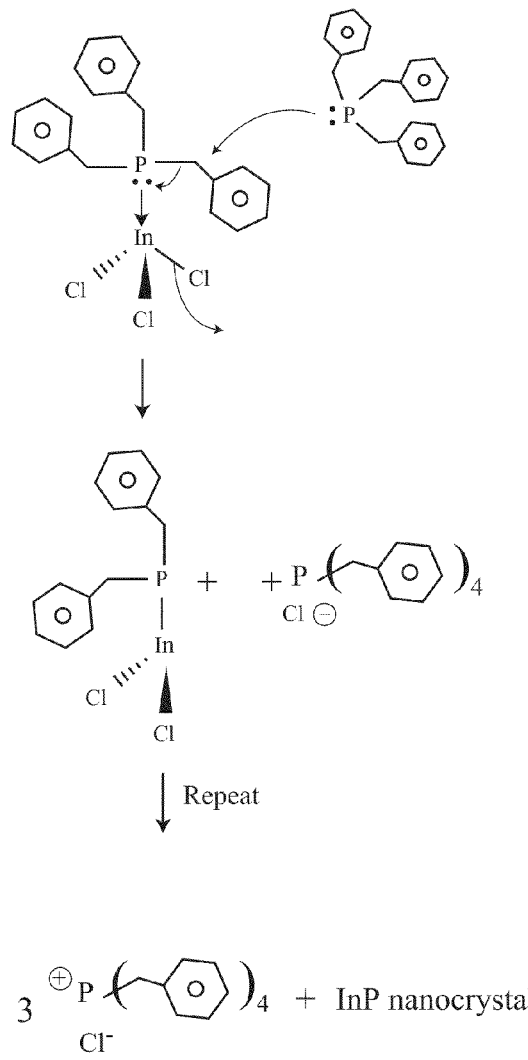
Fig. 1A
Fig. 1B

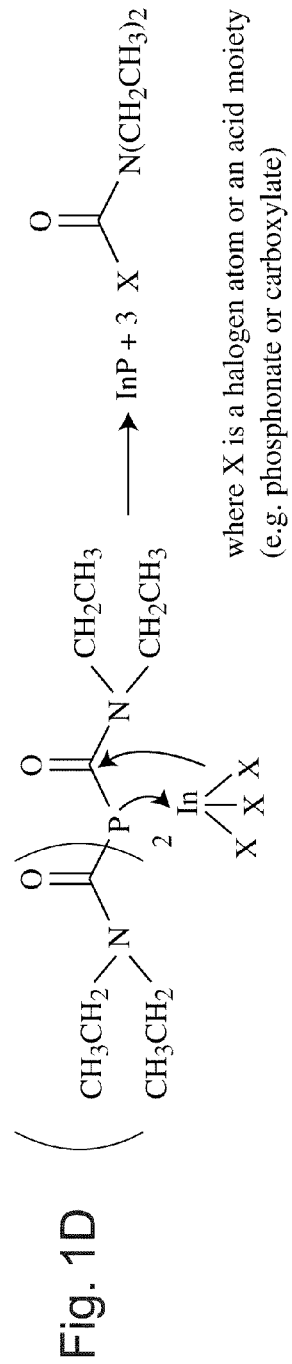
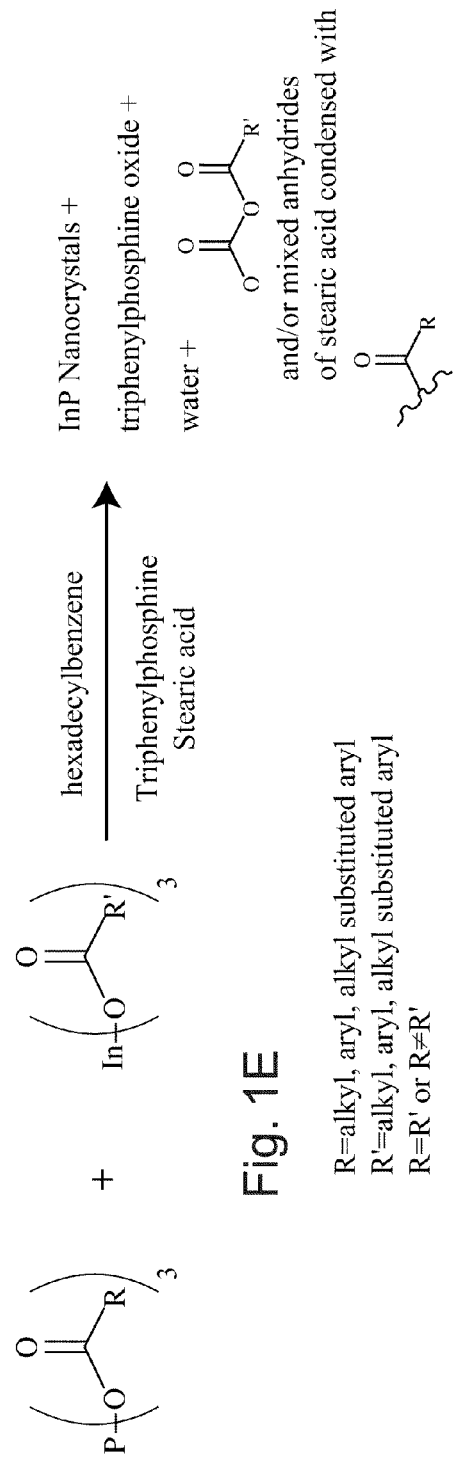
Fig. 1C
Fig. 1D
Fig. 1E

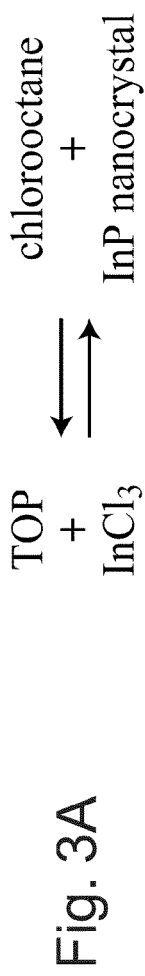
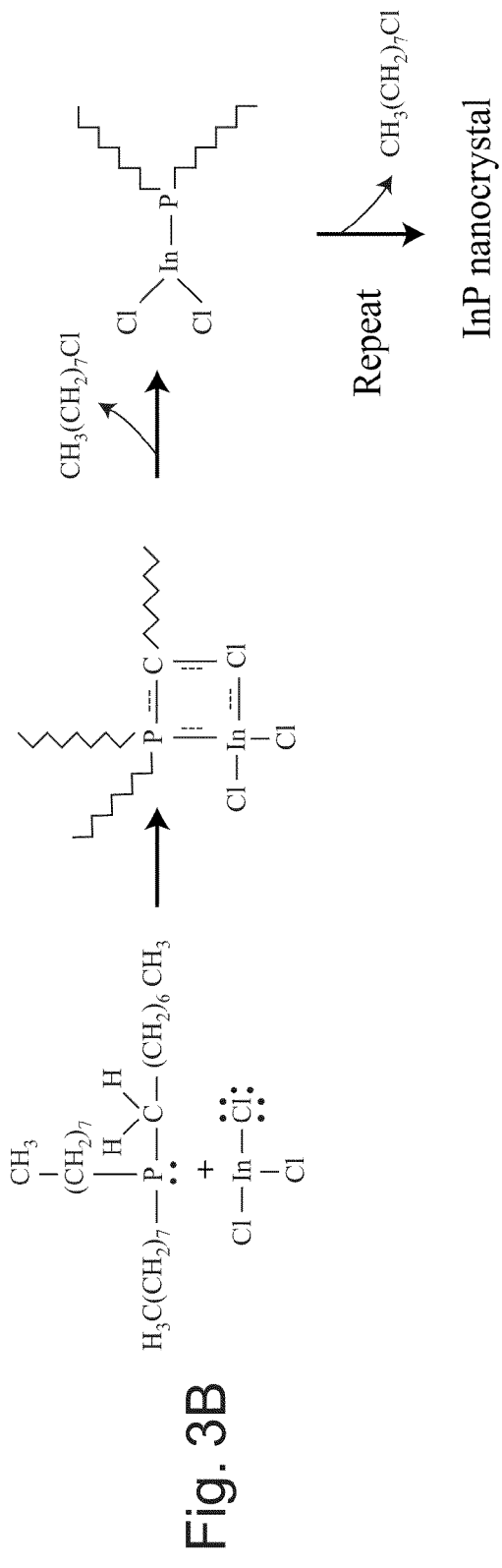
Fig. 3A
Fig. 3B

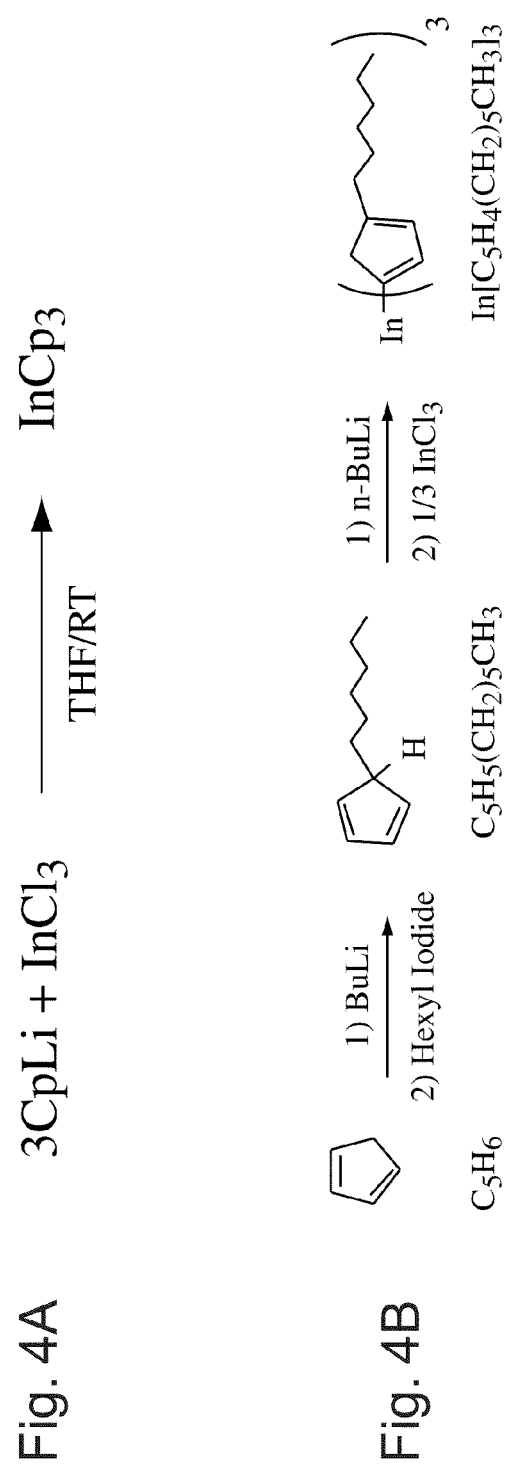
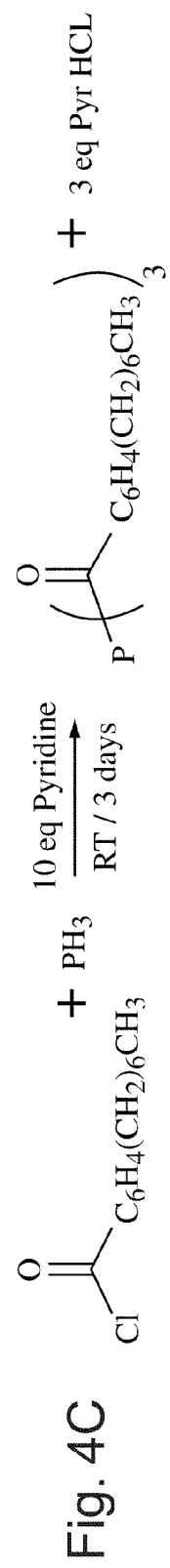
Fig. 4A
Fig. 4B
Fig. 4C

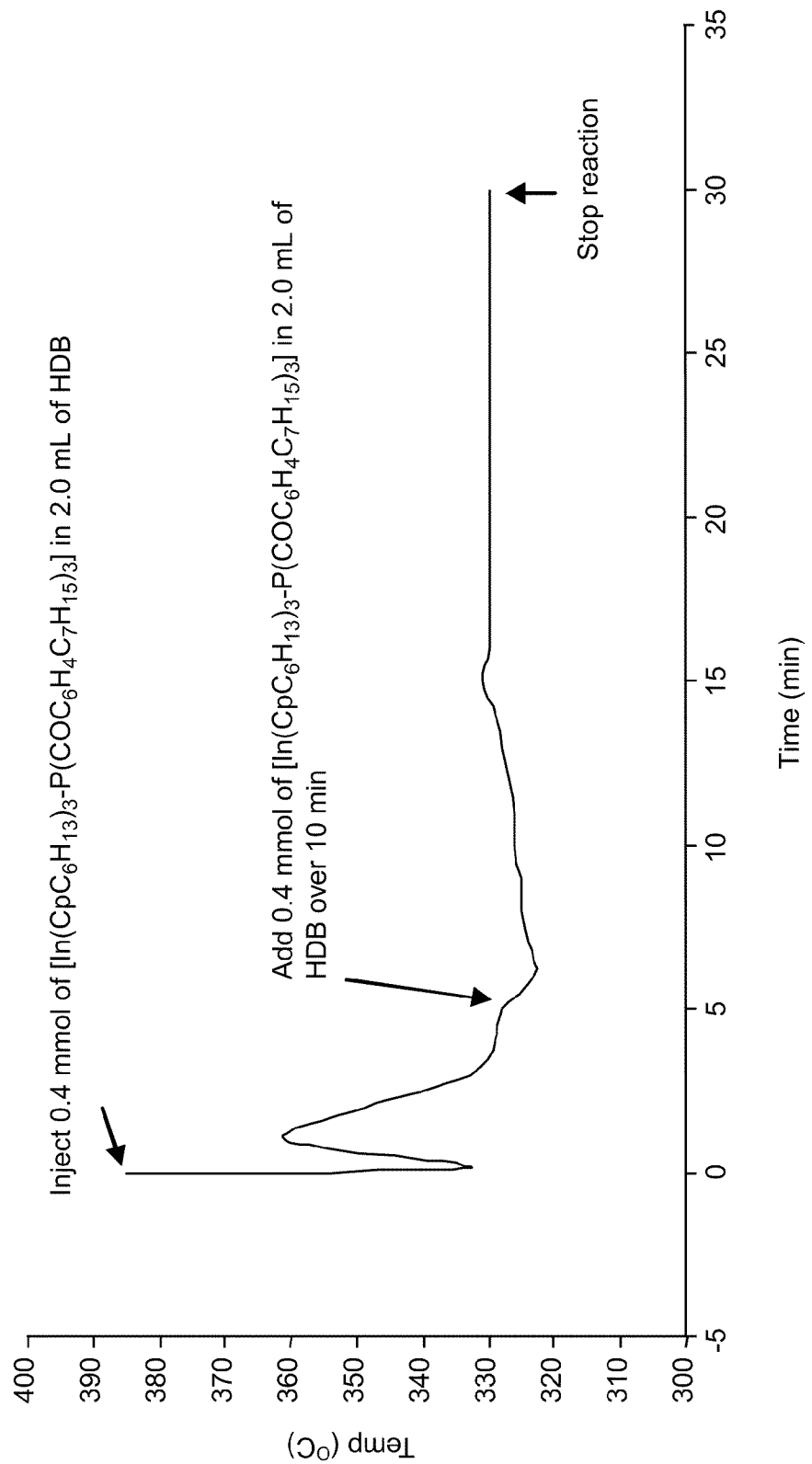

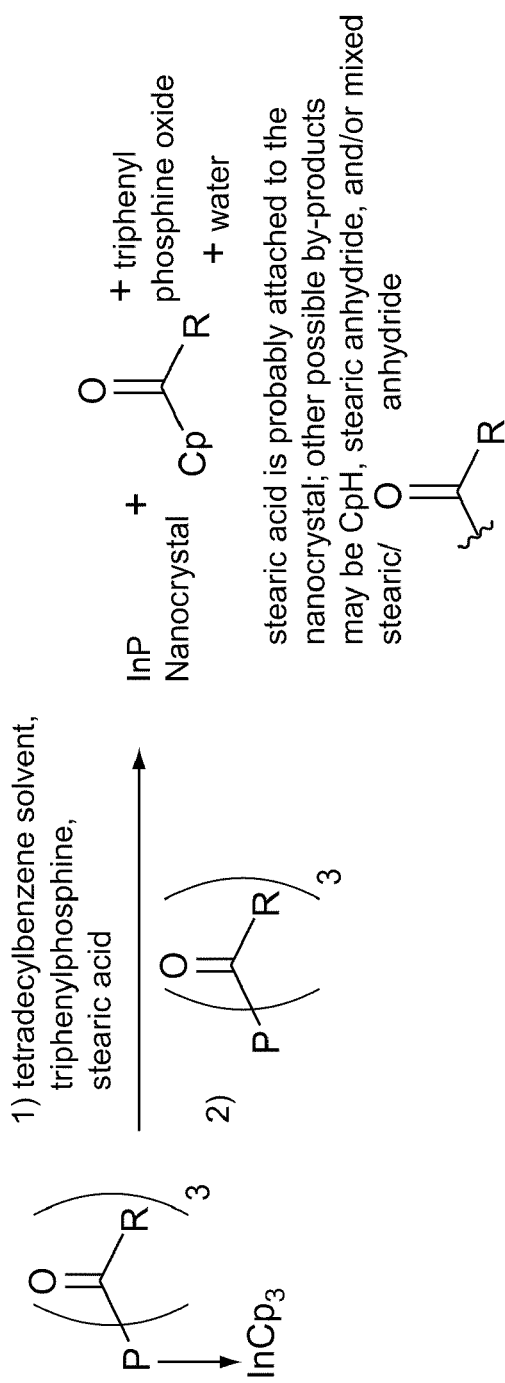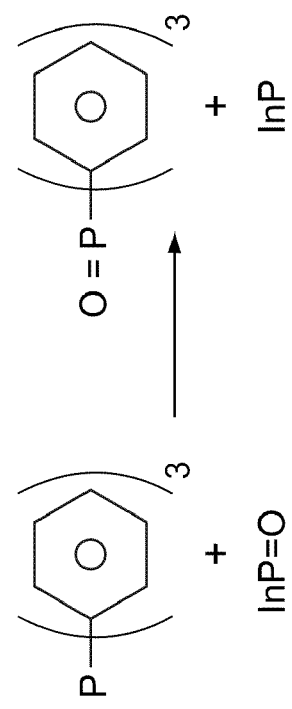
Fig. 8A
Fig. 8B

PROCESS FOR GROUP III-V SEMICONDUCTOR NANOSTRUCTURE SYNTHESIS AND COMPOSITIONS MADE USING SAME

CROSS-REFERENCE TO RELATED APPLICATIONS

This application is a divisional of U.S. patent application Ser. No. 11/178,257, filed Jul. 8, 2005, which claims the benefit of U.S. Provisional Patent Applications No. 60/628,455 filed Nov. 15, 2004 and 60/591,987 filed Jul. 28, 2004, each of which is incorporated by reference in its entirety herein.

FIELD OF THE INVENTION

The invention is in the field of nanostructure synthesis. The invention relates to methods for producing nanostructures, particularly Group III-V semiconductor nanostructures. The invention also relates to compositions useful in producing nanostructures, and to methods and compositions for producing Group III inorganic compounds that can be used as precursors for nanostructure synthesis.

BACKGROUND OF THE INVENTION

Semiconductor nanostructures can be incorporated into a variety of electronic and optical devices, for example, photovoltaic devices and LEDs. The electrical and optical properties of such nanostructures vary, e.g., depending on their composition, shape, and size. Group III-V semiconductors, for example, exhibit a number of desirable electrical properties such as low energy and direct band gap behaviors and high electron mobility, as well as other desirable properties such as thermal stability.

Methods for simply and reproducibly producing Group III-V semiconductor nanostructures, e.g., nanostructures of different sizes and/or shapes, are thus desirable. Among other aspects, the present invention provides such methods. A complete understanding of the invention will be obtained upon review of the following.

SUMMARY OF THE INVENTION

Methods for producing nanostructures, particularly Group III-V semiconductor nanostructures, are provided. The methods include, e.g., use of novel Group III and/or Group V precursors, novel surfactants, sacrificial oxide acceptors, high temperature, and/or stable co-products. Related compositions are also described. Methods and compositions for producing Group III inorganic compounds that can be used as precursors for nanostructure synthesis are provided. Methods for increasing the yield of nanostructures from a synthesis reaction by removal of a vaporous by-product are also described.

A first general class of embodiments provides methods for production of Group III-V semiconductor nanostructures. In the methods, a first precursor and a second precursor are provided, and the first and second precursors are reacted to produce the nanostructures. The first precursor comprises a trisubstituted Group V atom, other than a) a trialkyl substituted Group V atom comprising an unbranched and unsubstituted alkyl group, b) an $H_3$ substituted Group V atom, c) an $H_2$alkyl substituted Group V atom comprising an unbranched and unsubstituted alkyl group, d) an $Halkyl_2$ substituted Group V atom comprising an unbranched and unsubstituted alkyl group, or e) a tris(trialkylsilyl) substituted Group V atom. The second precursor comprises a Group III atom. The Group V atom can be any atom selected from Group V of the periodic table of the elements. In a preferred class of embodiments, the Group V atom is N, P, As, Sb, or Bi.

In one class of embodiments, the first precursor is a Group V organometallic compound. In one aspect, the first precursor comprises a Group V atom substituted with three unsaturated groups. For example, the first precursor can be triallylphosphine, trivinylphosphine, tributadienylphosphine, trialkylethynylphosphine, trialkylethenylphosphine, tri(4-phenylethynyl)phosphine, or trialkylphenylethynylphosphine. As another example, the first precursor can include a Group V atom substituted with three furyl or furfuryl groups; e.g., the first precursor can be tri-2-furylphosphine or tri-2-furfurylphosphine.

In one class of embodiments, the first precursor comprises a triacyl substituted Group V atom. The acyl group can be, e.g., unsubstituted or substituted. For example, the first precursor can be a triacylphosphine or a triacylarsine, e.g., tribenzoylphosphine, trialkylbenzoylphosphine, trihexylbenzoylphosphine, trialkoylphosphine, or trihexoylphosphine. The second precursor optionally includes three unsaturated groups, substituting the Group III atom.

In a related class of embodiments, the first precursor comprises a triaryl substituted Group V atom. The aryl group can be, e.g., unsubstituted or substituted. In one class of example embodiments, the first precursor comprises a tribenzyl substituted Group V atom; for example, the first precursor can be tribenzylphosphine or tribenzylarsine.

In another related class of embodiments, the first precursor comprises a Group V atom substituted with three carboxamide groups. Thus, for example, the first precursor can be a tricarboxamide phosphine, e.g., N,N,N,N,N,N-hexaethylphosphine tricarboxamide.

In another class of embodiments, the first precursor comprises a trialkyl substituted Group V atom comprising a substituted and/or branched alkyl group. For example, the first precursor can include a tri-t-butyl substituted Group V atom; e.g., the first precursor can be tri-t-butylphosphine.

In certain embodiments, the first precursor is a Group V inorganic compound. For example, in one class of embodiments, the first precursor comprises a Group V atom substituted with three carboxylate moieties or with three phosphinate moieties. In one embodiment, the Group V atom is P such that the first precursor is a phosphite ester. The second precursor optionally also includes three carboxylate moieties or with three phosphinate moieties, substituting the Group III atom.

The first precursor can be used in combination with essentially any suitable second precursor, whether previously known in the art or described herein. The Group III atom can be any atom selected from Group III of the periodic table of the elements. In a preferred class of embodiments, the Group III atom is B, Al, Ga, In, or Tl.

In one aspect, the second precursor is a Group III inorganic compound. In one class of embodiments, the second precursor is a Group III halide. Thus, in this class of embodiments, the second precursor is $YZ_3$, where Y is a Group III atom (e.g., B, Al, Ga, In, or Tl) and Z is a halogen atom (e.g., F, Cl, Br, I, or At).

In another class of embodiments, the second precursor comprises one or more phosphonate, phosphinate, carboxylate, sulfonate, and/or boronate moieties bonded to the Group III atom. For example, the second precursor can comprise a bi- or tri-substituted Group III atom (e.g., a tricarboxylate, bi- or tri-phosphonate, or triphosphinate substituted Group III atom). Thus, in one class of embodiments, the second precursor is Y(alkylcarboxylate)$_3$, Y(arylcarboxylate)$_3$, Y(alkylphosphonate)$_3$, Y(arylphosphonate)$_3$, Y(alkylphosphonate)$_2$, Y(arylphosphonate)$_2$, Y(bialkylphosphinate)$_3$, or Y(biarylphosphinate)$_3$, where Y is B, Al, Ga, In, or Tl. The alkyl or aryl group can be, e.g., substituted or unsubstituted. For example, the second precursor can be an indium phosphonate or indium carboxylate (e.g., indium triacetate or indium tristearate).

In yet another class of embodiments, the second precursor is a Group III metal oxide. For example, the second precursor can be indium oxide or gallium oxide. As another example, the second precursor can be a Group III alkoxy or Group III aryloxy (e.g., a Group III phenoxy, e.g., indium phenoxy).

In one class of embodiments, instead of being a Group III inorganic compound, the second precursor is a Group III organometallic compound. For example, the second precursor can be an alkyl metal or a trialkyl metal, e.g., trimethyl indium or triethyl indium. In one aspect, the second precursor comprises a Group III atom substituted with three unsaturated groups. For example, the second precursor can be triallyl indium, trivinyl indium, tributadiene indium, trialkylethynyl indium, trialkylethenyl indium, tri-4-phenylethynyl indium, or trialkylphenylethynyl indium. In other embodiments, the second precursor comprises a Group III atom substituted with three cyclic ketone groups; for example, the second precursor can be tris-alpha-cyclohexanone indium (III). In yet other embodiments, the second precursor comprises a Group III atom substituted with three cyclopentadienyl or substituted cyclopentadienyl groups. For example, the second precursor can be an indium tris-Cp compound or an indium tris-(substituted Cp) compound, for example, tris-cyclopentadienyl indium(III) or tris(n-hexyl cyclopentadienyl) indium(III).

In one class of embodiments, the first precursor comprises a trisubstituted Group V atom where the substituents are dienes, while the second precursor includes a trisubstituted Group III atom where the substituents are dienophiles. In a related class of embodiments, the first precursor comprises a trisubstituted Group V atom where the substituents are dienophiles while the second precursor includes a trisubstituted Group III atom where the substituents are dienes.

The first and second precursors are typically reacted in the presence of at least one surfactant. For example, the precursors can be reacted in the presence of a first surfactant, a second surfactant, or a mixture of first and second surfactants. Suitable first surfactants include, but are not limited to, tri-n-alkyl phosphines (e.g., TOP and tri-n-butyl phosphine (TBP), and C12-C30 tri-n-alkyl phosphines, e.g., tri-n-dodecyl phosphine or tri-n-hexadecyl phosphine), tri-n-alkyl phosphine oxides (e.g., TOPO), alkyl amines (e.g., monoalkyl amines and bialkyl amines, or trialkyl amines such as trioctylamine), and alkyl- and/or aryl-thiols. Suitable first surfactants also include unsaturated Group V derivatives; the first surfactant can comprise a Group V atom substituted with three unsaturated groups (e.g., alkenyl or alkynyl groups). Examples include trisalkylphenylethynylphosphines, e.g., tri(ethynylbenzene-hexyl)phosphine, tris(ethynylbenzene-pentyl)phosphine, and the other unsaturated phosphines noted herein.

Suitable second surfactants include, but are not limited to, alkyl amines (e.g., mono-, bi-, and tri-alkyl amines; typically, the first surfactant is not also an alkyl amine) and phosphonic acids (e.g., a C2-30 alkylphosphonic acid), phosphinic acids (e.g., a C2-30 bialkylphosphinic acid), carboxylic acids (e.g., a C2-30 alkylcarboxylic acid), boronic acids, and sulfonic acids, as well as deprotonated forms or condensates thereof.

In one class of embodiments, the first and second precursors are reacted in the presence of a non-coordinating solvent, e.g., an alkane or an alkene, e.g., hexadecane, octadecane, octadecene, phenyldodecane, phenyltetradecane, or phenylhexadecane. In one class of embodiments, the first and second precursors are reacted in the presence of the non-coordinating solvent and a first and/or second surfactant (e.g., any of those described herein). For example, the first and second precursors can be reacted in the presence of the non-coordinating solvent (e.g., phenylhexadecane) and a carboxylic acid (e.g., stearic acid), and optionally also in the presence of a sacrificial oxide acceptor (e.g., triphenylphosphine).

Using a mixture of surfactants, varying the ratio of the surfactant(s) to the precursors, and/or varying the ratio of the precursors to each other permits the shape and/or size of the resulting nanostructures to be controlled. Thus, in one class of embodiments, reacting the first and second precursors comprises reacting the first and second precursors in the presence of at least a first surfactant and a second surfactant, whereby the shape of the nanostructures produced is capable of being controlled by adjusting the ratio of the first and second surfactants. For example, the ratio of the first and second surfactants can be adjusted to produce substantially spherical nanocrystals, nanorods, branched nanostructures, and/or nanotetrapods. Additional surfactants can also be used to help control the shape of the resulting nanocrystals. Thus, in some embodiments, the first and second precursors are reacted in the presence of a first surfactant, a second surfactant, and a third surfactant.

In a related class of embodiments, reacting the first and second precursors comprises reacting the first and second precursors in the presence of a second surfactant, whereby the shape of the nanostructures produced is capable of being controlled by adjusting the ratio of the second surfactant and the first or second precursor. For example, the ratio of the second surfactant and the first or second precursor can be adjusted to produce substantially spherical nanocrystals, nanorods, branched nanostructures, and/or nanotetrapods.

In another related class of embodiments, the ratio of the first and second precursors is adjusted to control the shape of the nanostructures produced. As for the embodiments above, the ratio of the first and second precursors can be adjusted to produce, e.g., substantially spherical nanocrystals, nanorods, branched nanostructures, and/or nanotetrapods.

Alternatively or in addition, the temperature can be controlled to control the shape and/or size distribution of the resulting nanostructures. Thus, in one class of embodiments, reacting the first and second precursors to produce the nanostructures includes heating at least one surfactant (e.g., a first and a second surfactant) to a first temperature; contacting the first and second precursors and the heated surfactant, whereby the first and second precursors react to form nuclei capable of nucleating nanostructure growth; and maintaining the first and second precursors, the surfactant, and the nuclei at a second temperature. The second temperature permits growth of the nuclei to produce the nanostructures, whereby the first and second precursors react to grow the nanostructures from the nuclei. The first (nucleation) temperature is typically greater than the second temperature, e.g., by about 40-80° C., about 20-40° C., about 10-20° C., about 5-10° C., or about 0-5° C.; the first and second temperatures can, however, be equal, or the first temperature can be less than the second temperature (e.g., by about 40-80° C., about 20-40° C., about 10-20° C., about 5-10° C., or about 0-5° C.). In some embodiments, the first temperature is at least 300° C., at least 330° C., at least 360° C., at least 380° C., at least 400° C., or at least 420° C. In some embodiments, the second temperature is at least 250° C., at least 275° C., at least 300° C., at least 320° C., at least 340° C., at least 360° C., at least 380° C., at least 400° C., or at least 420° C.

Yield of nanostructures from the reaction is optionally increased by removal of one or more by-products during the reaction. Thus, in some embodiments, the first and second precursors react to produce the nanostructures and a by-product that has a boiling point or sublimation temperature that is less than the second temperature. The methods include removing at least a portion of the by-product as a vapor.

The precursors can be added either simultaneously or sequentially to a reaction vessel in which nanostructure synthesis is performed. Thus, in one class of embodiments, reacting the first and second precursors to produce the nanostructures includes contacting the first and second precursors, which form a Group III-V complex. The Group III-V complex is then reacted to produce the nanostructures. The complex is optionally isolated after it is formed.

In one class of embodiments, the first and second precursors are reacted in the presence of a sacrificial oxide acceptor, e.g., a pi-acid such as triphenylphosphine or a substituted triphenylphosphine.

The nanostructures produced by the methods can be essentially any shape and/or size. For example, the resulting nanostructures can include nanocrystals, substantially spherical nanocrystals, nanorods, branched nanostructures, and/or nanotetrapods. Similarly, the nanostructures can comprise essentially any Group III-V semiconductor, including, but not limited to, InN, InP, InAs, InSb, GaN, GaP, GaAs, GaSb, AlN, AlP, AlAs, or AlSb.

Another general class of embodiments provides high temperature methods for production of Group III-V semiconductor nanostructures. In the methods, a first precursor and a second precursor are provided. The first and second precursors are reacted at a first temperature of at least 300° C. to produce the nanostructures. The first precursor comprises a trisubstituted Group V atom, where the three substituents on the Group V atom are independently any alkyl group or hydrogen. The second precursor comprises a Group III atom. The first temperature is optionally at least 330° C., at least 360° C., at least 380° C., at least 400° C., or at least 420° C.

The first precursor can include an $H_3$ substituted Group V atom, an $H_2$alkyl substituted Group V atom, or an $H$alkyl$_2$ substituted Group V atom. In a preferred class of embodiments, the first precursor comprises a trialkyl substituted Group V atom. The alkyl group can be, e.g., substituted or unsubstituted and/or branched or unbranched (linear). For example, the first precursor can comprise a trimethyl substituted Group V atom, a triethyl substituted Group V atom, or a tri-t-butyl substituted Group V atom. Specific examples of first precursors include, but are not limited to, trimethylphosphine, triethylphosphine, and tri-t-butylphosphine.

Essentially all of the features noted above apply to this embodiment as well, as relevant; e.g., for types and composition of nanostructures produced, second precursors, removal of by-product to increase nanostructure yield, use of first and/or second surfactants, and controlling nanostructure shape by adjusting the ratio of the first and second surfactants, the ratio of the second surfactant and the first or second precursor, and/or the ratio of the first and second precursors. It is worth noting that the molar ratio of the first precursor to the second precursor can be varied; for example, the first precursor can be provided at a molar ratio of at least 1:1, at least 2:1, at least 4:1, at least 8:1, or at least 12:1 with respect to the second precursor.

Yet another general class of embodiments also provides methods for production of Group III-V semiconductor nanostructures. In the methods, a first precursor and a second precursor are provided, and the first and second precursors are reacted to produce the nanostructures. The first precursor comprises a Group V atom. The second precursor is either a Group III inorganic compound other than a Group III halide (e.g., $InCl_3$) or a Group III acetate (e.g., $InAc_3$), or a Group III organometallic compound other than a trialkyl substituted Group III atom comprising an unbranched and unsubstituted alkyl group.

The Group III atom can be any atom selected from Group III of the periodic table of the elements. In a preferred class of embodiments, the second precursor comprises B, Al, Ga, In, or Tl as the Group III atom.

In one aspect, the second precursor is a Group III inorganic compound (e.g., a compound in which the Group III atom is directly bonded to at least one oxygen atom or other heteroatom, e.g., nitrogen).

In one class of embodiments, the second precursor is a Group III inorganic compound comprising one or more phosphonate, phosphinate, carboxylate, sulfonate, and/or boronate moieties bonded to a Group III atom. For example, the second precursor can comprise a bi- or tri-substituted Group III atom (e.g., a tricarboxylate, bi- or tri-phosphonate, or triphosphinate substituted Group III atom). Thus, in one class of embodiments, the Group III inorganic compound is Y(alkylcarboxylate)$_3$, Y(arylcarboxylate)$_3$, Y(alkylphosphonate)$_3$, Y(arylphosphonate)$_3$, Y(alkylphosphonate)$_2$, Y(arylphosphonate)$_2$, Y(bialkylphosphinate)$_3$, or Y(biarylphosphinate)$_3$, where Y is B, Al, Ga, In, or Tl. The alkyl or aryl group can be, e.g., substituted or unsubstituted. For example, the second precursor can be an indium phosphonate or indium carboxylate other than indium triacetate (e.g., indium tristearate).

In another class of embodiments, the Group III inorganic compound is a Group III metal oxide. For example, the Group III inorganic compound can be indium oxide or gallium oxide. As another example, the Group III inorganic compound can be a Group III alkoxy or Group III aryloxy (e.g., a Group III phenoxy, e.g., indium phenoxy).

In another aspect, instead of being a Group III inorganic compound, the second precursor is a Group III organometallic compound. In one aspect, the second precursor comprises a Group III atom substituted with three unsaturated groups. For example, the second precursor can be triallyl indium, trivinyl indium, tributadiene indium, trialkylethynyl indium, trialkylethenyl indium, tri-4-phenylethynyl indium, or trialkylphenylethynyl indium. In one class of embodiments, the second precursor comprises a Group III atom substituted with three cyclic ketone groups; for example, the second precursor can be tris-alpha-cyclohexanone indium (III). In other embodiments, the second precursor comprises a Group III atom substituted with three cyclopentadienyl or substituted cyclopentadienyl groups. For example, the second precursor can be an indium tris-Cp compound or an indium tris-(substituted Cp) compound, for example, tris-cyclopentadienyl indium(III) or tris(n-hexyl cyclopentadienyl) indium(III).

Essentially all of the features noted above apply to this embodiment as well, as relevant; e.g., for types and composition of nanostructures produced, first precursors, non-coordinating solvents, sacrificial oxide acceptors, removal of by-product to increase nanostructure yield, use of first and/or second surfactants, and controlling nanostructure shape by adjusting the ratio of the first and second surfactants, the ratio of the second surfactant and the first or second precursor, and/or the ratio of the first and second precursors.

Another general class of embodiments provides methods of producing a Group III inorganic compound. In the methods, a first reactant and a second reactant are provided and reacted to produce the Group III inorganic compound. In some embodiments, the first reactant is a Group III halide, e.g., $YZ_3$, where Y is B, Al, Ga, In, or Tl and Z is F, Cl, Br, I, or At. In other embodiments, the first reactant comprises a trialkyl substituted Group III atom (e.g., trialkyl indium, e.g., trimethyl indium). The second reactant is an acid, e.g., a phosphonic acid, a phosphinic acid, a carboxylic acid (e.g., stearic acid), a sulfonic acid, or a boronic acid.

The resulting Group III inorganic compound thus, in certain embodiments, comprises one or more phosphonate, phosphinate, and/or carboxylate moieties bonded to the Group III atom. Examples of such compounds include, but are not limited to, $Y(alkylcarboxylate)_3$, $Y(arylcarboxylate)_3$, $Y(alkylphosphonate)_3$, $Y(arylphosphonate)_3$, $Y(alkylphosphonate)_2$, $Y(arylphosphonate)_2$, $Y(bialkylphosphinate)_3$, and $Y(biarylphosphinate)_3$, where Y is B, Al, Ga, In, or Tl. For example, the Group III inorganic compound can be indium phosphonate or indium carboxylate (e.g., indium tristearate).

The second reactant is typically provided at a molar ratio of about 3:1 with respect to the first reactant (e.g., about 2.8-3.2, about 2.9-3.1, or about 2.95-3.05). In other embodiments, the second reactant is provided at a molar ratio of more than 3:1 with respect to the first reactant.

The resulting Group III inorganic compound is optionally used as a precursor in a nanostructure synthesis reaction. Thus, in one class of embodiments, the methods include providing a first precursor comprising a Group V atom and reacting the Group III inorganic compound and the first precursor to produce Group III-V semiconductor nanostructures. The Group III inorganic compound is optionally substantially isolated from any unreacted first reactant and/or second reactant prior to its reaction with the first precursor.

Essentially all of the features noted above apply to this embodiment as well, as relevant; e.g., for first precursors.

Another general class of embodiments provides high-temperature methods for production of Group III-V semiconductor nanostructures. In the methods, one or more surfactants, a first precursor comprising a Group V atom, and a second precursor comprising a Group III atom are provided. The one or more surfactants are heated to a first temperature. The first and second precursors and the one or more heated surfactants are contacted, and the first and second precursors react to form nuclei capable of nucleating nanostructure growth. The first and second precursors, the one or more surfactants, and the nuclei are maintained at a second temperature which permits growth of the nuclei to produce the nanostructures; the first and second precursors react to grow the nanostructures from the nuclei. The first temperature is at least 360° C. and/or the second temperature is at least 300° C.

For example, the first temperature can be at least 380° C., at least 400° C., or at least 420° C. Similarly, the second temperature can be at least 330° C., at least 360° C., at least 380° C., at least 400° C., or at least 420° C. The first temperature can be greater than (or less than) the second temperature, e.g., by about 40-80° C., about 20-40° C., about 10-20° C., about 5-10° C., or about 0-5° C., or the first and second temperatures can be equal. In a preferred class of embodiments, each of the one or more surfactants has a boiling point that is greater than the first and second temperatures.

Essentially all of the features noted above apply to this embodiment as well, as relevant; e.g., for types and composition of nanostructures produced, removal of by-product to increase nanostructure yield, Group III and V atoms, first and second precursors, use of first and/or second surfactants, and controlling nanostructure shape by adjusting the ratio of the first and second surfactants, the ratio of the second surfactant and the first or second precursor, and/or the ratio of the first and second precursors. It is worth noting that, in one class of embodiments, the first surfactant is a tri-n-alkyl phosphine or a tri-n-alkyl phosphine oxide, for example, a C12-C30 tri-n-alkyl phosphine (e.g., tri-n-dodecyl phosphine or tri-n-hexadecyl phosphine).

Yet another general class of embodiments provides methods for production of Group III-V semiconductor nanostructures. In the methods, a first precursor comprising a Group V atom and a second precursor comprising a Group III atom are provided and reacted to produce the nanostructures and at least one co-product. In one class of embodiments, the co-product is an ester, a ketone, or an ether.

Reaction of a variety of combinations of first and second precursors results in formation of an ether, ketone, or ester. For example, when the first precursor comprises a trialkyl substituted Group V atom and the second precursor comprises a tricarboxylate substituted Group III atom, the co-product can be an ester. As another example, the first precursor can comprise a triacyl substituted Group V atom, the second precursor a Group III atom substituted with three cyclic ketone groups (e.g., tris-alpha-cyclohexanone indium (III)), and the co-product an ester. As yet another example, the first precursor can comprise a triacyl substituted Group V atom, the second precursor a tris-Cp or tris-(substituted Cp) Group III atom (e.g., an indium tris-Cp or tris-(substituted Cp) compound, e.g., tris-cyclopentadienyl indium(III) or tris (n-hexyl cyclopentadienyl) indium(III)), and the co-product a ketone.

The methods optionally include substantially purifying the nanostructures away from the co-product (e.g., prior to their use or incorporation into an optoelectronic device, a nanocomposite, or the like).

In one aspect, the invention provides methods for production of nanostructures that can, e.g., increase yield of nanostructures from nanostructure synthesis reactions through removal of a vapor by-product. In the methods, one or more precursors are provided and reacted at a reaction temperature (e.g., a nanostructure growth temperature) to produce the nanostructures and at least one by-product. The by-product has a boiling point or sublimation temperature that is less than the reaction temperature. At least a portion of the by-product is removed as a vapor. Removal of the by-product pushes the reaction equilibrium toward making more nanostructures.

The nanostructures can be of essentially any type and/or composition. For example, the nanostructures can be semiconductor nanostructures, e.g., Group II-VI semiconductor nanostructures, Group III-V semiconductor nanostructures, Group IV semiconductor nanostructures, metal nanostructures, or metal oxide nanostructures.

In one class of embodiments, the one or more precursors comprise a first precursor comprising a group VI atom and a second precursor comprising a group II atom, or a first precursor comprising a group V atom and a second precursor comprising a group III atom. The resulting nanostructures can comprise, e.g., ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, InN, InP, InAs, InSb, GaN, GaP, GaAs, GaSb, AlN, AlP, AlAs, or AlSb.

A number of precursors and reaction temperatures can be selected such that the by-product formed has a boiling point or sublimation temperature less than the reaction temperature. For example, in one class of embodiments, at least two precursors are reacted to form Group III-V semiconductor nanostructures. The first precursor comprises a trialkyl or triaryl substituted Group V atom, the second precursor is a Group III halide, and the by-product is thus an alkyl or aryl halide. Preferably, the Group V atom is N, P, As, Sb, or Bi, and the Group III halide comprises B, Al, Ga, In, or Tl and F, Cl, Br, I, or At. Example by-products include, but are not limited to, chlorooctane, bromooctane, benzylbromide, benzyliodide, or benzylchloride. In one example embodiment, the first precursor is TOP, the second precursor is $InCl_3$, and the by-product is chlorooctane. Essentially all of the features noted above apply to these embodiments as well, as relevant; e.g., for types and composition of nanostructures produced, inclusion of surfactant(s), precursors, and the like.

Methods and compositions including surfactants of the invention (e.g., tri-unsaturated Group V derivatives) form a feature of the invention. Thus, one general class of embodiments provides methods for production of nanostructures. In the methods, a surfactant comprising a Group V atom substituted with three unsaturated groups and one or more precursors are provided. The one or more precursors are reacted in the presence of the surfactant to produce the nanostructures. In one class of embodiments, the nanostructures are Group III-V semiconductor nanostructures; in this class of embodiments, the one or more precursors can, e.g., include a first precursor comprising a Group V atom and a second precursor comprising a Group III atom.

The three unsaturated groups on the Group V atom in the surfactant optionally comprise alkenyl or alkynyl groups. Thus, for example, the surfactant can be a trisalkylphenyl-ethynylphosphine, e.g., trisalkylphenylethynylphosphine or tri(ethynylbenzene-hexyl)phosphine.

Compositions related to the methods are another feature of the invention. Thus, one general class of embodiments provides a composition including a first precursor and a second precursor. The first precursor comprises a trisubstituted Group V atom, other than a) a trialkyl substituted Group V atom comprising an unbranched and unsubstituted alkyl group, b) an $H_3$ substituted Group V atom, c) an $H_2$alkyl substituted Group V atom comprising an unbranched and unsubstituted alkyl group, d) an $H$alkyl$_2$ substituted Group V atom comprising an unbranched and unsubstituted alkyl group, or e) a tris(trialkylsilyl) substituted Group V atom. The second precursor comprises a Group III atom.

Essentially all of the features noted above apply to this embodiment as well, as relevant; e.g., for first and second precursors, non-coordinating solvents, sacrificial oxide acceptors, and first and/or second surfactants. It is worth noting that the composition optionally includes one or more nanostructures comprising the Group III atom and the Group V atom.

A related general class of embodiments provides a composition that includes a first precursor and a second precursor, where the temperature of the composition is at least 300° C. (e.g., at least 330° C., at least 360° C., at least 380° C., at least 400° C., or at least 420° C.). The first precursor comprises a trisubstituted Group V atom, where the three substituents on the Group V atom are independently any alkyl group or hydrogen. The second precursor comprises a Group III atom.

Essentially all of the features noted above apply to this embodiment as well, as relevant; e.g., for first and second precursors, non-coordinating solvents, sacrificial oxide acceptors, and first and/or second surfactants. It is worth noting that, in one class of embodiments, the first surfactant is a tri-n-alkyl phosphine, for example, TOP, TBP, or a C12-C30 tri-n-alkyl phosphine (e.g., tri-n-dodecyl phosphine or tri-n-hexadecyl phosphine). It is also worth noting that the molar ratio of the first precursor to the second precursor can be varied; for example, the first precursor can be present at a molar ratio of at least 1:1, at least 2:1, at least 4:1, at least 8:1, or at least 12:1 with respect to the second precursor. The composition optionally includes one or more nanostructures comprising the Group III atom and the Group V atom.

Another general class of embodiments provides a composition including a first precursor comprising a Group V atom and a second precursor. The second precursor is either a Group III inorganic compound other than a Group III halide (e.g., $InCl_3$) or a Group III acetate (e.g., $InAc_3$), or a Group III organometallic compound other than a trialkyl substituted Group III atom comprising an unbranched and unsubstituted alkyl group. In certain embodiments, second precursors of the invention optionally exclude any trialkyl substituted Group III atom.

Essentially all of the features noted above apply to this embodiment as well, as relevant; e.g., for first and second precursors, non-coordinating solvents, sacrificial oxide acceptors, and first and/or second surfactants. It is worth noting that the composition optionally includes one or more nanostructures comprising the Group III atom and the Group V atom.

Another general class of embodiments provides a composition that can be used, for example, for producing a Group III inorganic compound. The composition includes a first reactant and a second reactant. In some embodiments, the first reactant is a Group III halide, e.g., $YZ_3$, where Y is B, Al, Ga, In, or Tl and Z is F, Cl, Br, I, or At. In other embodiments, the first reactant comprises a trialkyl substituted Group III atom (e.g., trialkyl indium, e.g., trimethyl indium). The second reactant is an acid, e.g., a phosphonic acid, a phosphinic acid, a carboxylic acid (e.g., stearic acid), a sulfonic acid, or a boronic acid.

Essentially all of the features noted above apply to this embodiment as well, as relevant; e.g., for first and second reactants, Group III inorganic compounds, and the like. It is worth noting that the composition optionally includes a first precursor, a nanostructure, and/or the like.

Yet another general class of embodiments provides a composition comprising one or more surfactants, a first precursor comprising a Group V atom, and a second precursor comprising a Group III atom. The temperature of the composition is at least 360° C. (e.g., at least 380° C., at least 400° C., or at least 420° C.). Each of the one or more surfactants preferably has a boiling point that is greater than the temperature of the composition.

Essentially all of the features noted above apply to this embodiment as well, as relevant; e.g., for first and second precursors, surfactants, and the like. It is worth noting that the composition optionally includes one or more nanostructures comprising the Group III atom and the Group V atom.

Another general class of embodiments provides a composition comprising a first precursor comprising a Group V atom, a second precursor comprising a Group III atom, a nanostructure comprising the Group III atom and the Group V atom, and a co-product. In one class of embodiments, the co-product is an ester, a ketone, or an ether. The nanostructure and the co-product were produced by reaction of the precursors.

Essentially all of the features noted above apply to this embodiment as well, as relevant; e.g., for first and second precursors, co-products, composition of the nanostructures, and the like.

Another general class of embodiments provides a composition including a surfactant comprising a Group V atom substituted with three unsaturated groups and one or more precursors. The composition optionally also includes one or more nanostructures, e.g., Group III-V semiconductor nanostructures. The one or more precursors can, e.g., include a first precursor comprising a Group V atom and a second precursor comprising a Group III atom.

Essentially all of the features noted above apply to this embodiment as well, as relevant. For example, the three unsaturated groups on the Group V atom in the surfactant optionally comprise alkenyl or alkynyl groups. Thus, for example, the surfactant can be a trisalkylphenylethynylphosphine, e.g., trisalkylphenylethynylphosphine or tri(ethynyl-benzene-hexyl)phosphine.

Nanostructures (including, but not limited to, nanocrystals, substantially spherical nanocrystals, nanorods, branched nanostructures, or nanotetrapods) produced by any of the methods herein form another feature of the invention. One general class of embodiments provides a nanostructure comprising a Group III-V semiconductor. The nanostructure is substantially free of metallic noble, Group Ib, Group IIb, Group IIIb, and transition metal elements, and is optionally substantially free of any metallic metal element. In one class of embodiments, the nanostructure is a branched nanostructure or a nanostructure having an aspect ratio greater than about 1.2, and the nanostructure has a wurtzite crystal structure or a zinc blende-wurtzite mixed crystal structure. For example, in one class of embodiments, the nanostructure is a nanotetrapod. In another class of embodiments, the nanostructure is a nanorod having an aspect ratio greater than about 1.2, greater than about 1.5, greater than about 2, greater than about 3, or greater than about 5.

The Group III-V semiconductor typically comprises a first atom selected from the group consisting of N, P, As, Sb, and Bi and a second atom selected from the group consisting of B, Al, Ga, In, and Tl.

The nanostructures are optionally substantially free of Si, phosphonic acid, phosphinic acid, carboxylic acid, tri-n-alkyl phosphines and/or tri-n-alkyl phosphine oxides. In certain embodiments, the nanostructures have a sulfonic acid, or a boronic acid, or a deprotonated form or a condensate thereof, associated with a surface of the nanostructures. In other embodiments, the nanostructures have a carboxylic acid or a deprotonated form or a condensate thereof, and/or a surfactant comprising a Group V atom substituted with three unsaturated groups, associated with a surface of the nanostructures.

Another general class of embodiments provides a nanostructure comprising a Group III-V semiconductor, the nanostructure being a tetrahedral nanostructure. In one class of embodiments, the nanostructure has an edge at least 10 nm in length (e.g., at least 12 nm, at least 15 nm, or at least 20 nm). All six edges are optionally at least 10 nm in length. The nanostructure can be, e.g., a nanocrystal, and can have a zinc blende crystal structure. Essentially all of the features noted above apply to this embodiment as well, as relevant; e.g., for composition of the nanostructure. Devices (e.g., photovoltaic devices or other opto-electronic devices) including nanostructures of the invention are also a feature of the invention.

Compositions including nanostructures and one or more Group III precursor, Group V precursor, and/or surfactant of the invention are also a feature of the invention. Thus, one general class of embodiments provides a composition that includes one or more nanostructures (e.g., Group III-V semiconductor nanostructures) having a surfactant associated (covalently or non-covalently) with a surface thereof. The surfactant comprises a Group V atom substituted with three unsaturated groups, e.g., alkenyl or alkynyl groups. Essentially all of the features noted above apply to this embodiment as well, as relevant; e.g., for types and composition of nanostructures, types of surfactant, and the like. For example, the surfactant can be a trisalkylphenylethynylphosphine, e.g., trisalkylphenylethynylphosphine or tri(ethynylbenzene-hexyl)phosphine.

Another general class of embodiments provides a composition that includes one or more Group III-V semiconductor nanostructures and a first precursor of the invention. For example, the first precursor can comprise a Group V atom substituted with three unsaturated groups, a triacyl substituted Group V atom, a Group V atom substituted with three carboxamide groups, a triaryl substituted Group V atom, or a Group V atom substituted with three carboxylate moieties or with three phosphinate moieties, for example, any such precursors described herein. For example, the first precursor can be triallylphosphine, trivinylphosphine, tributadienylphosphine, trialkylethynylphosphine, trialkylethenylphosphine, tri(4-phenylethynyl)phosphine, trialkylphenylethynylphosphine, a triacylphosphine, tribenzoylphosphine, trialkylbenzoylphosphine, trihexylbenzoylphosphine, trialkoylphosphine, trihexoylphosphine, a tricarboxamide phosphine, N,N,N,N,N,N-hexaethylphosphine tricarboxamide, tribenzylphosphine, or tribenzylarsine. As another example, the first precursor can include a Group V atom substituted with three furyl or furfuryl groups; e.g., the first precursor can be tri-2-furylphosphine or tri-2-furfurylphosphine. As yet another example, the first precursor can be a phosphite ester. The composition optionally includes a second precursor, a first surfactant, a second surfactant, and/or a non-coordinating solvent. Essentially all of the features noted above apply to this embodiment as well, as relevant; e.g., for types and composition of nanostructures, second precursors, first and second surfactants, solvents, sacrificial oxide acceptors, and the like.

Yet another general class of embodiments provides a composition that includes one or more Group III-V semiconductor nanostructures and a second precursor of the invention. For example, the second precursor can comprise a Group III atom which is directly bonded to at least one oxygen atom; one or more phosphonate, phosphinate, and/or carboxylate moieties other than an acetate moiety bonded to a Group III atom; a group III metal oxide; a Group III alkoxy or aryloxy; or a Group III atom substituted with three unsaturated groups. Thus, the second precursor can be, e.g., indium phosphonate, indium carboxylate, indium tristearate, indium oxide, gallium oxide, indium phenoxy, triallyl indium, trivinyl indium, tributadiene indium, trialkylethynyl indium, trialkylethenyl indium, tri-4-phenylethynyl indium, trialkylphenylethynyl indium, tris-alpha-cyclohexanone indium (III), an indium tris-Cp compound, an indium tris-(substituted Cp) compound, tris-cyclopentadienyl indium(III) or tris(n-hexyl cyclopentadienyl) indium(III). The composition optionally includes a first precursor, a first surfactant, a second surfactant, and/or a non-coordinating solvent. Essentially all of the features noted above apply to this embodiment as well, as relevant; e.g., for types and composition of nanostructures, first precursors, first and second surfactants, solvents, sacrificial oxide acceptors, and the like.

BRIEF DESCRIPTION OF THE DRAWINGS

FIG. 3 Panel A schematically illustrates an equilibrium between first precursor TOP and second precursor $InCl_3$ and products chlorooctane and InP. Removal of the chlorooctane by-product, e.g., as a vapor, drives the equilibrium to the right, resulting in formation of more InP nanocrystals. Panel B schematically illustrates a proposed mechanism for the reaction, which can be carried out in the presence of one or more suitable surfactants (e.g., TOPO).

FIG. 4 schematically depicts synthesis of example precursors. Panel A illustrates synthesis of tris-cyclopentadienyl indium. Panel B illustrates synthesis of tris-hexylcyclopentadienyl indium. Panel C illustrates synthesis of $P(COC_6H_4(CH_2)_6CH_3)_3$.

DEFINITIONS

Figure 1F:
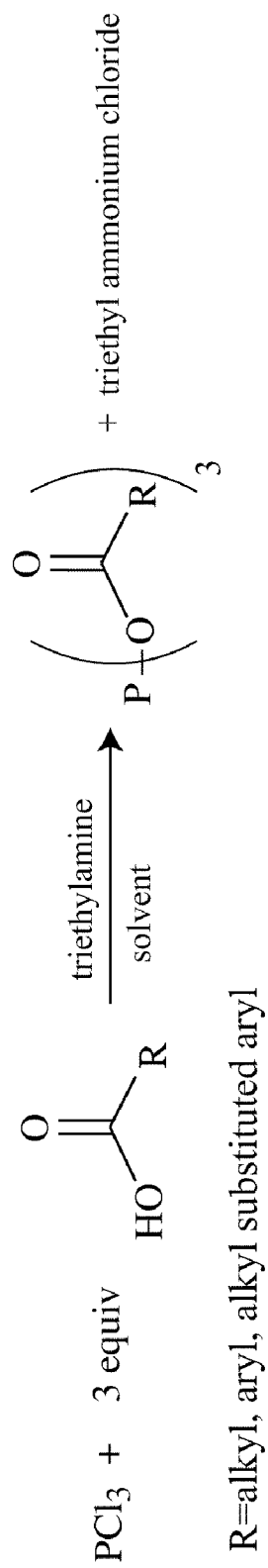
FIG. 1 Panel A depicts a possible sigma bond metathesis mechanism for the reaction of tribenzylphosphine with $InCl_3$. Panel B depicts a possible pseudo SN2 mechanism for the same reaction. Panel C depicts a tribenzylphosphine substituted with an electron withdrawing group. Panel D schematically illustrates reaction of a Group V tricarboxamide, N,N,N,N,N,N-hexaethylphosphine tricarboxamide, with an example Group III precursor (an indium halide, indium phosphonate, indium carboxylate, or the like) to form InP nanocrystals. Panel E schematically illustrates reaction of a first precursor comprising a Group V atom substituted with three carboxylate moieties with a second precursor comprising a Group III atom substituted with three carboxylate moieties. Panel F schematically illustrates an example reaction for synthesis of a first precursor comprising a Group V atom substituted with three carboxylate moieties. Panel G schematically illustrates an example reaction for synthesis of a second precursor comprising a Group III atom substituted with three carboxylate moieties.

Unless defined otherwise, all technical and scientific terms used herein have the same meaning as commonly understood by one of ordinary skill in the art to which the invention pertains. The following definitions supplement those in the art and are directed to the current application and are not to be imputed to any related or unrelated case, e.g., to any commonly owned patent or application. Although any methods and materials similar or equivalent to those described herein can be used in the practice for testing of the present invention, the preferred materials and methods are described herein. Accordingly, the terminology used herein is for the purpose of describing particular embodiments only, and is not intended to be limiting.

As used in this specification and the appended claims, the singular forms "a," "an" and "the" include plural referents unless the context clearly dictates otherwise. Thus, for example, reference to "a nanostructure" includes a plurality of such nanostructures, and the like.

The term "about" as used herein indicates the value of a given quantity varies by +/−10% of the value, or optionally +/−5% of the value, or in some embodiments, by +/−1% of the value so described.

An "acyl group" has the formula RC(O)—, where R is an organic group. The acyl group can be, e.g., substituted or unsubstituted. In a "substituted acyl group", at least one hydrogen in the organic group is replaced with one or more other atoms.

An "alkenyl group" refers to a linear, branched, or cyclic unsaturated hydrocarbon moiety that comprises one or more carbon-carbon double bonds. Alkenyl groups can be substituted or unsubstituted.

An "alkynyl group" refers to a linear, branched, or cyclic unsaturated hydrocarbon moiety that comprises one or more carbon-carbon triple bonds. Alkynyl groups can be substituted or unsubstituted.

An "alkyl amine" is an amine having at least one alkyl substituent on the nitrogen atom. A "monoalkyl amine" contains one alkyl group on the nitrogen, a "bialkyl amine" contains two alkyl groups on the nitrogen, and a "trialkyl amine" contains three alkyl groups on the nitrogen.

The term "alkyl-aryl group" refers to a group that comprises alkyl and aryl moieties.

The term "aryl group" refers to a chemical substituent comprising or consisting of an aromatic group. Exemplary aryl groups include, e.g., phenyl groups, benzyl groups, tolyl groups, xylyl groups, alkyl-aryl groups, or the like. Aryl groups optionally include multiple aromatic rings (e.g., diphenyl groups, etc.). The aryl group can be, e.g., substituted or unsubstituted. In a "substituted aryl group", at least one hydrogen is replaced with one or more other atoms.

An "aspect ratio" is the length of a first axis of a nanostructure divided by the average of the lengths of the second and third axes of the nanostructure, where the second and third axes are the two axes whose lengths are most nearly equal each other. For example, the aspect ratio for a perfect rod would be the length of its long axis divided by the diameter of a cross-section perpendicular to (normal to) the long axis.

A "branched nanostructure" is a nanostructure having three or more arms, where each arm has the characteristics of a nanorod, or a nanostructure having two or more arms, each arm having the characteristics of a nanorod and emanating from a central region that has a crystal structure distinct from that of the arms. Examples include, but are not limited to, bipods, tripods, and nanotetrapods (tetrapods).

Two atoms are "bonded to" each other when they share a chemical bond, e.g., a covalent bond, a polar covalent bond, or an ionic bond.

A "by-product" or "co-product" of a nanostructure synthesis reaction is a product produced in addition to the desired nanostructure.

A "carboxamide group" has the formula —C(O)NRR', where R and R' are independently selected organic groups (e.g., an alkyl or aryl group).

"Cp" represents cyclopentadiene or an unsubstituted cyclopentadienyl group, as will be clear from the context. A cyclopentadienyl group can be, e.g., substituted or unsubstituted. In a "substituted cyclopentadienyl group", at least one hydrogen is replaced with one or more other atoms.

The terms "crystalline" or "substantially crystalline," when used with respect to nanostructures, refer to the fact that the nanostructures typically exhibit long-range ordering across one or more dimensions of the structure. It will be understood by one of skill in the art that the term "long range ordering" will depend on the absolute size of the specific nanostructures, as ordering for a single crystal cannot extend beyond the boundaries of the crystal. In this case, "long-range ordering" will mean substantial order across at least the majority of the dimension of the nanostructure. In some instances, a nanostructure can bear an oxide or other coating, or can be comprised of a core and at least one shell. In such instances it will be appreciated that the oxide, shell(s), or other coating need not exhibit such ordering (e.g. it can be amorphous, polycrystalline, or otherwise). In such instances, the phrase "crystalline," "substantially crystalline," "substantially monocrystalline," or "monocrystalline" refers to the central core of the nanostructure (excluding the coating layers or shells). The terms "crystalline" or "substantially crystalline" as used herein are intended to also encompass structures comprising various defects, stacking faults, atomic substitutions, and the like, as long as the structure exhibits substantial long range ordering (e.g., order over at least about 80% of the length of at least one axis of the nanostructure or its core). In addition, it will be appreciated that the interface between a core and the outside of a nanostructure or between a core and an adjacent shell or between a shell and a second adjacent shell may contain non-crystalline regions and may even be amorphous. This does not prevent the nanostructure from being crystalline or substantially crystalline as defined herein.

The "diameter of a nanocrystal" refers to the diameter of a cross-section normal to a first axis of the nanocrystal, where the first axis has the greatest difference in length with respect to the second and third axes (the second and third axes are the two axes whose lengths most nearly equal each other). The first axis is not necessarily the longest axis of the nanocrystal; e.g., for a disk-shaped nanocrystal, the cross-section would be a substantially circular cross-section normal to the short longitudinal axis of the disk. Where the cross-section is not circular, the diameter is the average of the major and minor axes of that cross-section.

The "diameter of a nanorod" refers to the diameter of a cross-section normal to the major principle axis (the long axis) of the nanorod. Where the cross-section is not circular, the diameter is the average of the major and minor axes of that cross-section.

An "ester" has the formula RC(O)OR', where R and R' are independently selected organic groups (e.g., an alkyl or aryl group).

An "ether" comprises two carbon atoms attached to a single oxygen atom.

A "furyl group" comprises a furan ring.

A "furfuryl group" is an acyl group comprising a furan ring (e.g., furan-2-carboxaldehyde).

A "ketone" comprises two carbon atoms attached to a single carbonyl group.

A "Group III atom" is an atom selected from Group III of the periodic table of the elements. Examples include, but are not limited to, B, Al, Ga, In, and Tl.

A "Group V atom" is an atom selected from Group V of the periodic table of the elements. Examples include, but are not limited to, N, P, As, Sb, and Bi.

A "Group III inorganic compound" contains a Group III atom that is directly bonded to at least one non-carbon atom and that is not directly bonded to a carbon atom. For example, the Group III atom can be bonded to at least one oxygen or halogen atom.

A "Group III alkoxy" contains a Group III atom directly bonded to the oxygen atom of at least one alkoxy group (which contains an alkyl group bonded to the oxygen).

A "Group III aryloxy" contains a Group III atom directly bonded to the oxygen atom of at least one aryloxy group (which contains an aryl group bonded to the oxygen).

A "Group III organometallic compound" contains a Group III atom directly bonded to at least one carbon atom.

A "Group V organometallic compound" contains a Group V atom directly bonded to at least one carbon atom.

The term "Group III-V semiconductor" refers to a semiconductor containing at least one Group III atom and at least one Group V atom. Typically, a Group III-V semiconductor includes one Group III atom and one Group V atom; examples include, but are not limited to, InN, InP, InAs, InSb, GaN, GaP, GaAs, GaSb, AlN, AlP, AlAs, or AlSb.

A "heteroatom" refers to any atom which is not a carbon or hydrogen atom. Examples include, but are not limited to, oxygen, nitrogen, sulfur, phosphorus, and boron.

The term "monocrystalline" when used with respect to a nanostructure indicates that the nanostructure is substantially crystalline and comprises substantially a single crystal. When used with respect to a nanostructure heterostructure comprising a core and one or more shells, "monocrystalline" indicates that the core is substantially crystalline and comprises substantially a single crystal.

A "nanocrystal" is a nanostructure that is substantially monocrystalline. A nanocrystal thus has at least one region or characteristic dimension with a dimension of less than about 500 nm, e.g., less than about 200 nm, less than about 100 nm, less than about 50 nm, or even less than about 20 nm. The term "nanocrystal" is intended to encompass substantially monocrystalline nanostructures comprising various defects, stacking faults, atomic substitutions, and the like, as well as substantially monocrystalline nanostructures without such defects, faults, or substitutions. In the case of nanocrystal heterostructures comprising a core and one or more shells, the core of the nanocrystal is typically substantially monocrystalline, but the shell(s) need not be. In one aspect, each of the three dimensions of the nanocrystal has a dimension of less than about 500 nm, e.g., less than about 200 nm, less than about 100 nm, less than about 50 nm, or even less than about 20 nm. Examples of nanocrystals include, but are not limited to, substantially spherical nanocrystals, branched nanocrystals, and substantially monocrystalline nanowires, nanorods, nanodots, quantum dots, nanotetrapods, tripods, bipods, and branched tetrapods (e.g., inorganic dendrimers).

A "substantially spherical nanocrystal" is a nanocrystal with an aspect ratio between about 0.8 and about 1.2.

A "nanorod" is a nanostructure that has one principle axis that is longer than the other two principle axes. Consequently, the nanorod has an aspect ratio greater than one. Nanorods of this invention typically have an aspect ratio between about 1.5 and about 10, but can have an aspect ratio greater than about 10, greater than about 20, greater than about 50, or greater than about 100, or even greater than about 10,000. Longer nanorods (e.g., those with an aspect ratio greater than about 10) are sometimes referred to as nanowires. The diameter of a nanorod is typically less than about 500 nm, preferably less than about 200 nm, more preferably less than about 150 nm, and most preferably less than about 100 nm, about 50 nm, or about 25 nm, or even less than about 10 nm or about 5 nm. Nanorods can have a variable diameter or can have a substantially uniform diameter, that is, a diameter that shows a variance less than about 20% (e.g., less than about 10%, less than about 5%, or less than about 1%) over the region of greatest variability. Nanorods are typically substantially crystalline and/or substantially monocrystalline, but can be, e.g., polycrystalline or amorphous.

A "nanostructure" is a structure having at least one region or characteristic dimension with a dimension of less than about 500 nm, e.g., less than about 200 nm, less than about 100 nm, less than about 50 nm, or even less than about 20 nm. Typically, the region or characteristic dimension will be along the smallest axis of the structure. Examples of such structures include nanowires, nanorods, nanotubes, branched nanostructures, nanotetrapods, tripods, bipods, nanocrystals, nanodots, quantum dots, nanoparticles, and the like. Nanostructures can be, e.g., substantially crystalline, substantially monocrystalline, polycrystalline, amorphous, or a combination thereof. In one aspect, each of the three dimensions of the nanostructure has a dimension of less than about 500 nm, e.g., less than about 200 nm, less than about 100 nm, less than about 50 nm, or even less than about 20 nm.

A "nanotetrapod" is a generally tetrahedral branched nanostructure having four arms emanating from a central region or core, where the angle between any two arms is approximately 109.5 degrees. Typically, the core has one crystal structure and the arms have another crystal structure.

A "phosphine" has the formula PRR'R", where R, R', and R" are independently an alkyl group, acyl group, aryl group (e.g., alkylaryl group), alkenyl group, alkynyl group, ester group, hydrogen, halide, or the like.

A "tri-n-alkyl phosphine" has the formula $PR_3$, where R is an n-alkyl group.

A "phosphinic acid" has the formula RR'P(O)OH, where R and R' are independently any organic group (e.g., any alkyl or aryl group) or hydrogen. A "phosphinate moiety" thus has the formula RR'P(O)O—.

A "phosphonic acid" has the formula $RP(O)(OH)_2$ or RP(O)(OR')(OH), where R and R' are independently an organic group (e.g., an alkyl or aryl group). A "phosphonate moiety" thus has the formula RP(O)(OH)O— or RP(O)(OR')O—.

A "carboxylic acid" has the formula RC(O)OH, where R is an organic group (e.g., an alkyl group or an aryl group). A "carboxylate moiety" thus has the formula RC(O)O—.

A "boronic acid" has the formula $RB(OH)_2$, where R is an organic group (e.g., an alkyl or aryl group) or hydrogen.

A "sulfonic acid" has the formula $RS(O)_2OH$, where R is an organic group (e.g., an alkyl or aryl group) or hydrogen.

A "precursor" in a nanostructure synthesis reaction is a chemical substance (e.g., a compound or element) that reacts, e.g., with another precursor, and thereby contributes at least one atom to the nanostructure produced by the reaction.

A "surfactant" is a molecule capable of interacting (whether weakly or strongly) with one or more faces of a nanostructure and/or with one or more precursors used in producing the nanostructure.

A "non-coordinating solvent" is one that does not interact with one or more faces of a nanostructure and/or with one or more precursors used in producing the nanostructure. A typical weakly binding surfactant comprises a heteroatom having a free (non-bonded within the surfactant) pair of electrons, while a typical non-coordinating solvent does not include such a heteroatom and free pair of electrons.

A "trisubstituted Group V atom" is a Group V atom that is directly bonded to three other atoms. The three other atoms can be identical or distinct. Each of the three other atoms is optionally part of a chemical group.

A "triacyl substituted Group V atom" is a Group V atom that is bonded to three identical acyl groups. The acyl group can be, e.g., substituted or unsubstituted.

A "trialkyl substituted Group V atom" is a Group V atom that is bonded to three identical alkyl groups. The alkyl group can be, e.g., unbranched or branched and/or substituted or unsubstituted.

A "triaryl substituted Group V atom" is a Group V atom that is bonded to three identical aryl groups. The aryl group can be, e.g., substituted or unsubstituted.

An "alkyl group" refers to a linear, branched, or cyclic saturated hydrocarbon moiety and includes all positional isomers. Alkyl groups can be, e.g., substituted or unsubstituted.

An "unbranched alkyl group" is a linear, n-alkyl group.

An "unsubstituted alkyl group" has the formula —$(CH_2)_nCH_3$, where n is greater than or equal to zero. In a "substituted alkyl group", at least one hydrogen is replaced with one or more other atoms. For example, at least one hydrogen can be replaced with a moiety containing one or more carbon, oxygen, sulfur, nitrogen, or halogen atoms. An alkyl group can, e.g., be branched or unbranched.

An "unsaturated group" contains at least one element of unsaturation. An "element of unsaturation" is a double bond (of any type), a triple bond (of any type), or a ring.

A variety of additional terms are defined or otherwise characterized herein.

DETAILED DESCRIPTION

Methods for colloidal synthesis of Group II-VI semiconductor nanostructures are known in the art. Such methods include techniques for controlling nanostructure growth, e.g., to control the size and/or shape distribution of the resulting nanostructures. For example, methods for colloidal synthesis of Group II-VI substantially spherical nanocrystals, nanorods, and nanotetrapods have been described. See, e.g., Manna et al. (2002) "Shape control of colloidal semiconductor nanocrystals" Journal of Cluster Science 13:521-532; Peng et al. (2000) "Shape control of CdSe nanocrystals" Nature 404:59-61; Puntes et al. (2001) "Colloidal nanocrystal shape and size control: The case of cobalt" Science 291:2115-

2117; U.S. Pat. No. 6,225,198 to Alivisatos et al., entitled "Process for forming shaped group II-VI semiconductor nanocrystals, and product formed using process"; Alivisatos (1996) "Semiconductor clusters, nanocrystals, and quantum dots" Science 271:933-937; Peng et al. (1997) "Epitaxial growth of highly luminescent CdSe/CdS core/shell nanocrystals with photostability and electronic accessibility" J. Am. Chem. Soc. 119:7019-7029; Murray et al. (1993) "Synthesis and characterization of nearly monodisperse CdE (E=sulfur, selenium, tellurium) semiconductor nanocrystallites" J. Am. Chem. Soc. 115: 8706-8715; and WO 03/054953 by Alivisatos et al., entitled "Shaped nanocrystal particles and methods for making the same".

In brief, Group II-VI semiconductor nanostructures can be produced by rapidly injecting precursors that undergo pyrolysis into a hot surfactant. The precursors can be injected simultaneously or sequentially. The precursors rapidly react to form nuclei. Nanostructure growth occurs through monomer addition to the nuclei, typically at a growth temperature that is lower than the injection/nucleation temperature.

The surfactant molecules interact with the surface of the nanostructure. At the growth temperature, the surfactant molecules rapidly adsorb and desorb from the nanostructure surface, permitting the addition and/or removal of atoms from the nanostructure while suppressing aggregation of the growing nanostructures. In general, a surfactant that coordinates weakly to the nanostructure surface permits rapid growth of the nanostructure, while a surfactant that binds more strongly to the nanostructure surface results in slower nanostructure growth. The surfactant can also interact with one (or more) of the precursors to slow nanostructure growth.

Nanostructure growth in the presence of a single surfactant typically results in spherical nanostructures. Using a mixture of two or more surfactants, however, permits growth to be controlled such that non-spherical nanostructures can be produced, if, for example, the two (or more) surfactants adsorb differently to different crystallographic faces of the growing nanostructure. For example, substantially spherical CdSe nanocrystals can be grown in trioctyl phosphine oxide (TOPO), while CdSe nanorods can be grown in a mixture of TOPO and hexyl phosphonic acid (Peng et al., supra).

A number of parameters are thus known to affect nanostructure growth and can be manipulated, independently or in combination, to control the size and/or shape distribution of the resulting nanostructures. These include, e.g., temperature (nucleation and/or growth), precursor composition, time-dependent precursor concentration, ratio of the precursors to each other, number of surfactants, surfactant composition, and ratio of surfactant(s) to each other and/or to the precursors.

Growth of a few types of Group III-V semiconductor nanostructures has also been described (see, e.g., U.S. Pat. No. 6,306,736 by Alivisatos et al. entitled "Process for forming shaped group III-V semiconductor nanocrystals, and product formed using process"). For example, Wells et al. (1989) "The use of tris(trimethylsilyl)arsine to prepare gallium arsenide and indium arsenide" Chem. Mater. 1:4-6, Guzelian et al. (1996) "Colloidal chemical synthesis and characterization of InAs nanocrystal quantum dots" 69: 1432-1434, Guzelian et al. (1996) "Synthesis of size-selected, surface-passivated InP nanocrystals" J. Phys. Chem. 100:7212-7219, and U.S. Pat. No. 5,505,928 to Alivisatos et al. entitled "Preparation of III-V semiconductor nanocrystals" describe the synthesis of substantially spherical group III-V nanocrystals or quantum dots. Published US Patent Application No. 2003/0214699 by Banin et al. entitled "Method for producing inorganic semiconductor nanocrystalline rods and their use" describes the use of a metal catalyst to nucleate the growth of rod-shaped Group III-V nanocrystals. The resulting nanocrystals, however, contain non-semiconducting material at one end, which can undesirably affect the electrical properties of the nanocrystals.

Thus, although growth of Group II-VI semiconductor nanostructures suggests principles that can be applied to growth of Group III-V nanostructures, application of these principles to produce Group III-V nanostructures of desired shapes and/or sizes has not been straightforward, in part due to lack of suitable precursors, surfactants, and combinations thereof. For example, either tris(trimethylsilyl)arsine or tris (trimethylsilyl)phosphine is typically used as the Group V atom source in synthesis of Group III-V nanostructures. Phosphonic acids, which are typically used as surfactants to control the growth of Group II-VI nanostructures to produce nanorods or nanotetrapods, react with the tris(trimethylsilyl) precursors, and can thus not be used in combination with these precursors to control synthesis of Group III-V nanostructures without the potential for non-beneficial side reactions to take place.

In one aspect, the present invention overcomes the above noted difficulties (e.g., the lack of suitable precursors and precursor-surfactant combinations for synthesis of Group III-V nanostructures) by providing novel Group III and Group V precursors. A number of methods for producing Group III-V nanostructures are described, along with related compositions. For example, use of precursors including trimethyl- and triethyl-substituted Group V atoms are described; these precursors do not react with phosphonic acids, which can thus be used as surfactants to control the shape of the resulting nanostructures. Methods and compositions for producing Group III inorganic compounds that can be used as precursors for nanostructure synthesis are provided. Suitable surfactants are also described (e.g., long chain tri-n-alkyl phosphines capable of withstanding higher temperatures, and unsaturated Group V derivatives), as are methods for increasing the yield of nanostructures from a synthesis reaction. Methods for producing nanostructures at high temperatures and/or in conjunction with a stable co-product are also features of the invention, as are compositions related to the methods.

Group V Precursors

In one aspect, the invention relates to novel Group V precursors (e.g., precursors that include a Group V atom substituted with three unsaturated groups). Methods using such precursors in production of Group III-V semiconductor nanostructures are provided. Related methods using Group V precursors at high temperatures are described. Compositions related to the methods are also provided.

Methods

Thus, a first general class of embodiments provides methods for production of Group III-V semiconductor nanostructures. In the methods, a first precursor and a second precursor are provided, and the first and second precursors are reacted to produce the nanostructures. The first precursor comprises a trisubstituted Group V atom. The trisubstituted Group V atom is other than a) a trialkyl substituted Group V atom comprising an unbranched and unsubstituted alkyl group, b) an $H_3$ substituted Group V atom, c) an $H_2$alkyl substituted Group V atom comprising an unbranched and unsubstituted alkyl group, d) an Halkyl$_2$ substituted Group V atom comprising an unbranched and unsubstituted alkyl group, or e) a tris(trialkylsilyl) substituted Group V atom. In certain embodiments, first precursors of the invention optionally exclude any trialkyl substituted, H₂alkyl substituted, or Halkyl₂ substituted Group V atom. The second precursor comprises a Group III atom.

The Group V atom can be any atom selected from Group V of the periodic table of the elements. In a preferred class of embodiments, the Group V atom is N, P, As, Sb, or Bi.

The three substituents on the Group V atom in the first precursor can be identical or distinct. The three substituents can be independently any organic group or hydrogen, for example. In one class of embodiments, the first precursor is a Group V organometallic compound, e.g., which can be used in a low temperature route or in a high temperature precursor decomposition route to solution-based synthesis of Group III-V semiconductor nano structures.

In one aspect, the first precursor comprises a Group V atom substituted with three unsaturated groups (e.g., any group including at least one double or triple bond or ring, including, but not limited to, alkenyl, alkynyl, acyl, and aryl groups). For example, the first precursor can be triallylphosphine, trivinylphosphine, tributadienylphosphine, trialkylethynylphosphine, trialkylethenylphosphine, tri(4-phenylethynyl)phosphine, or trialkylphenylethynylphosphine. See, e.g., Beletskaya et al. (2003) Organic Letters 5:4309-4311 for a description of ethynylphosphine synthesis and example ethynylphosphines. As another example, the first precursor can include a Group V atom substituted with three furyl or furfuryl groups; e.g., the first precursor can be tri-2-furylphosphine or tri-2-furfurylphosphine. See, e.g., Farina and Krishnan (1991) J. Am. Chem. Soc. 113:9585-9595.

In one class of embodiments, the first precursor comprises a triacyl substituted Group V atom. The acyl group can be, e.g., unsubstituted or substituted. For example, the first precursor can be a triacylphosphine or a triacylarsine, e.g., tribenzoylphosphine, trialkylbenzoylphosphine, trihexylbenzoylphosphine, trialkoylphosphine, or trihexoylphosphine. Synthesis of acyl phosphines has been described, e.g., in Tyka et al. (1961) Roczniki. Chem. 35:183, Tyka et al. (1962) Ref. Zh. Khim. 1 Zh 245, Barycki et al. (1978) Tetrahedron Letters 10:857, and Kost (1979) Tetrahedron Letters 22:1983.

In a related class of embodiments, the first precursor comprises a triaryl substituted Group V atom. The aryl group can be, e.g., unsubstituted or substituted. The substituent optionally comprises an electron donating group or an electron withdrawing group (a wide variety of electron donating and withdrawing groups are known in the art and can be adapted for use in the present invention). In one class of example embodiments, the first precursor comprises a tribenzyl substituted Group V atom; for example, the first precursor can be tribenzylphosphine or tribenzylarsine.

Figure 1G:
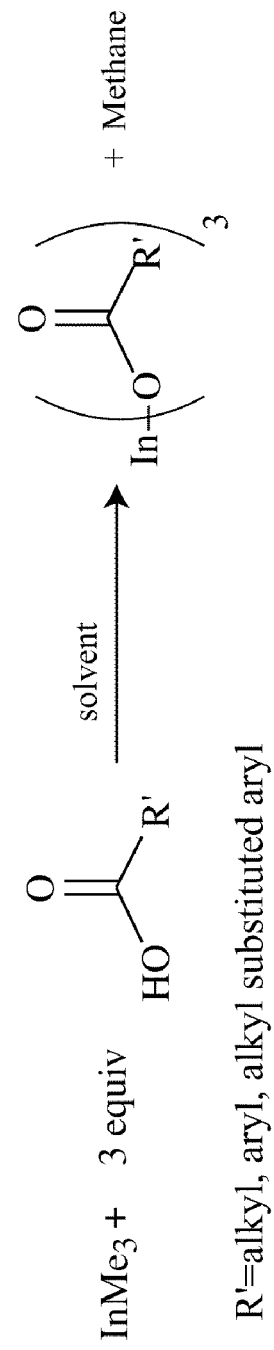
Figure 2A:
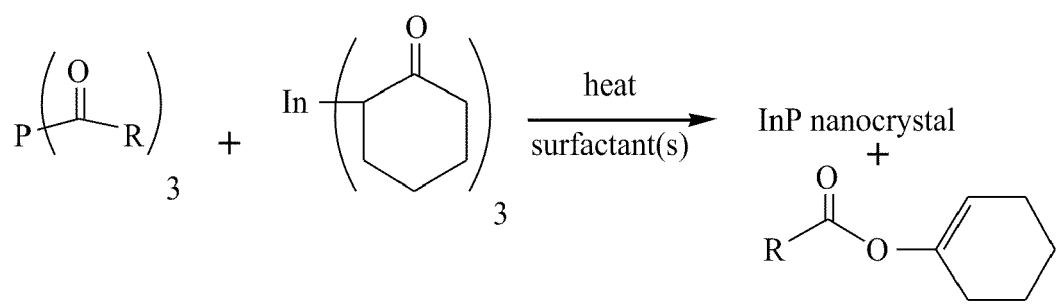
FIG. 2 Panel A schematically depicts the reaction of a triacylphosphine with tris-alpha-cyclohexanone indium (III) to produce InP nanocrystals and an ester co-product. Panel B illustrates a possible mechanism for the reaction of Panel A. Panel C outlines synthesis of a compound related to tris-alpha-cyclohexanone indium (III). Panel D outlines a suggested synthesis for tris-alpha-cyclohexanone indium (III). Panel E schematically depicts the reaction of a triacylphosphine with indium phenoxy to produce InP nanocrystals and an ester co-product. Panel F schematically depicts the reaction of a triacylphosphine with tris-cyclopentadienyl indium (III) to produce InP nanocrystals and a ketone co-product.
Figure 2B:
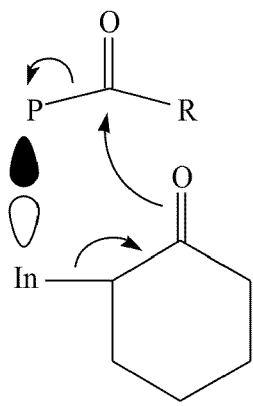
Figure 2C:
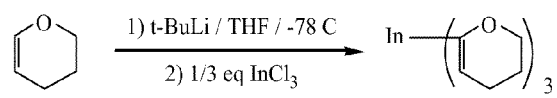
Figure 2D:
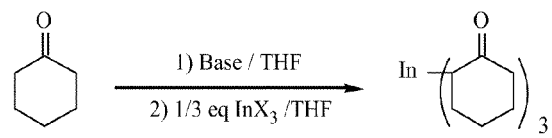
Figure 2E:
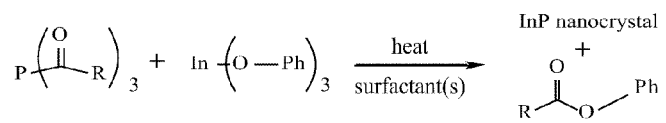
Figure 2F:
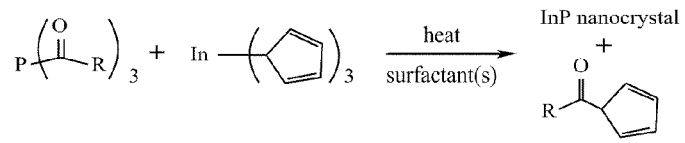
Figure 5A:
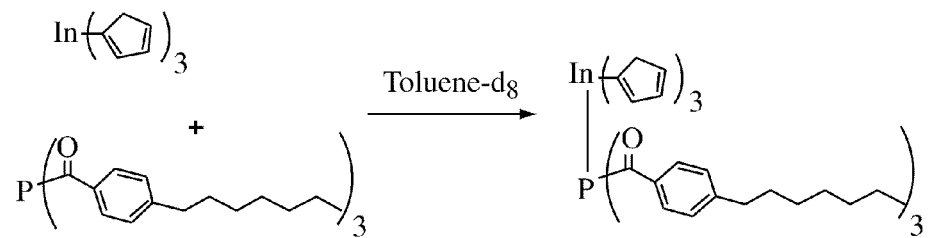
FIG. 5 Panels A and B schematically illustrate formation of an In—P complex. Panel C schematically illustrates synthesis of InP nanocrystals and a ketone co-product from the preformed precursor complex. Panel D presents the reaction temperature profile for the synthesis. Panel E presents results of mass spec analysis, showing a peak corresponding to the formula weight (fwt) 268.4 ketone co-product. Panel F shows a micrograph of the resulting InP nanocrystals. Panel G presents results of XRD analysis of the resulting InP nanocrystals.
Figure 5B:
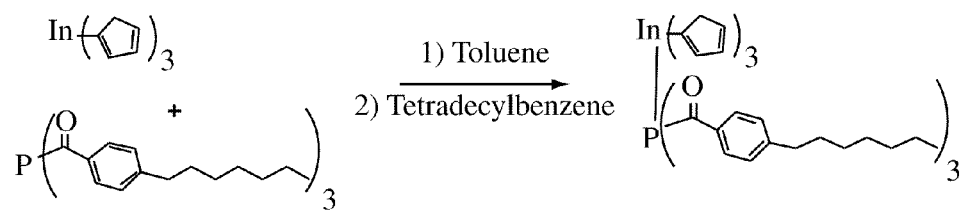
Figure 5C:
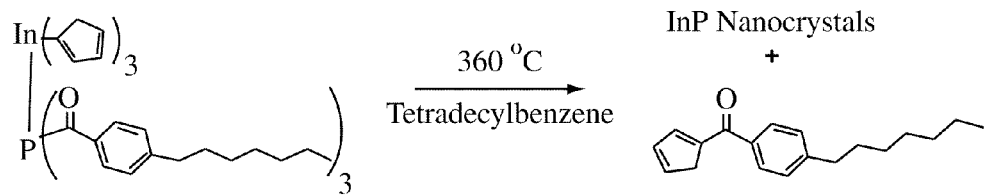
Figure 5D:
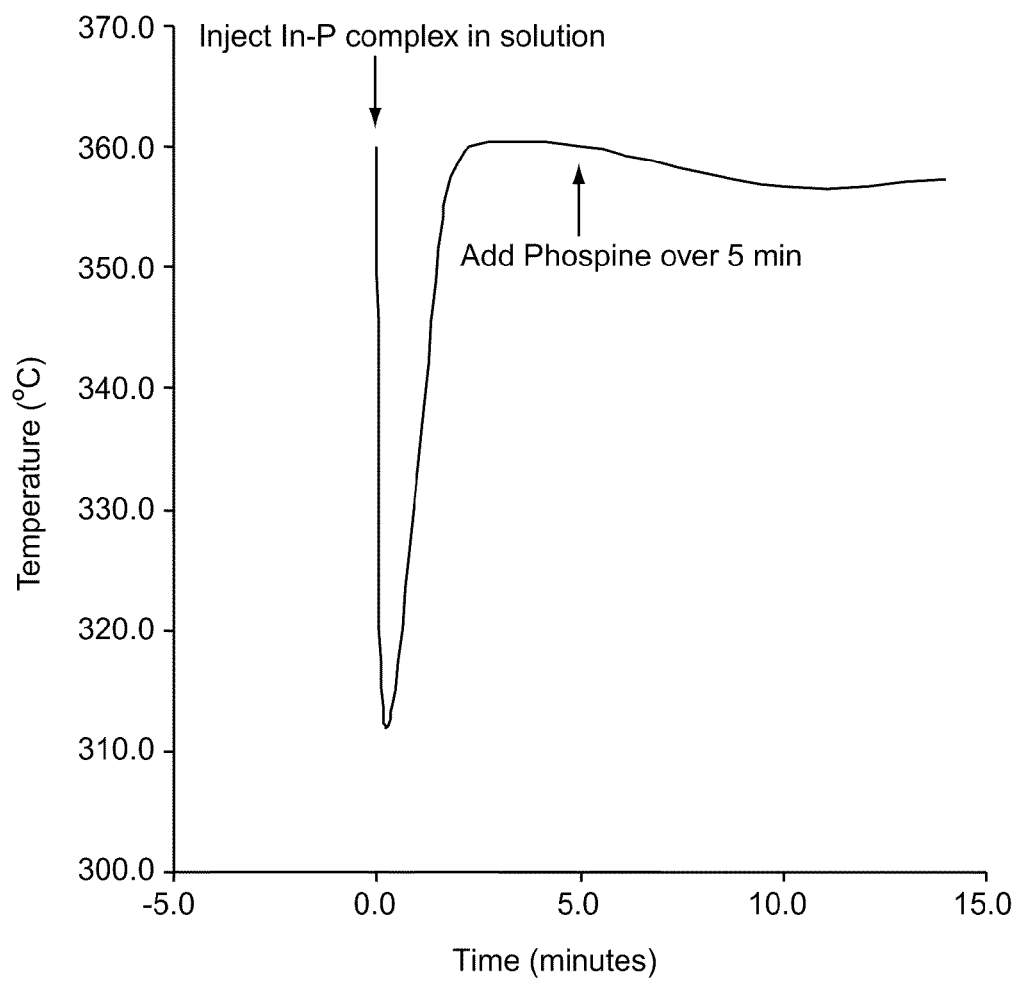
Figure 5E:
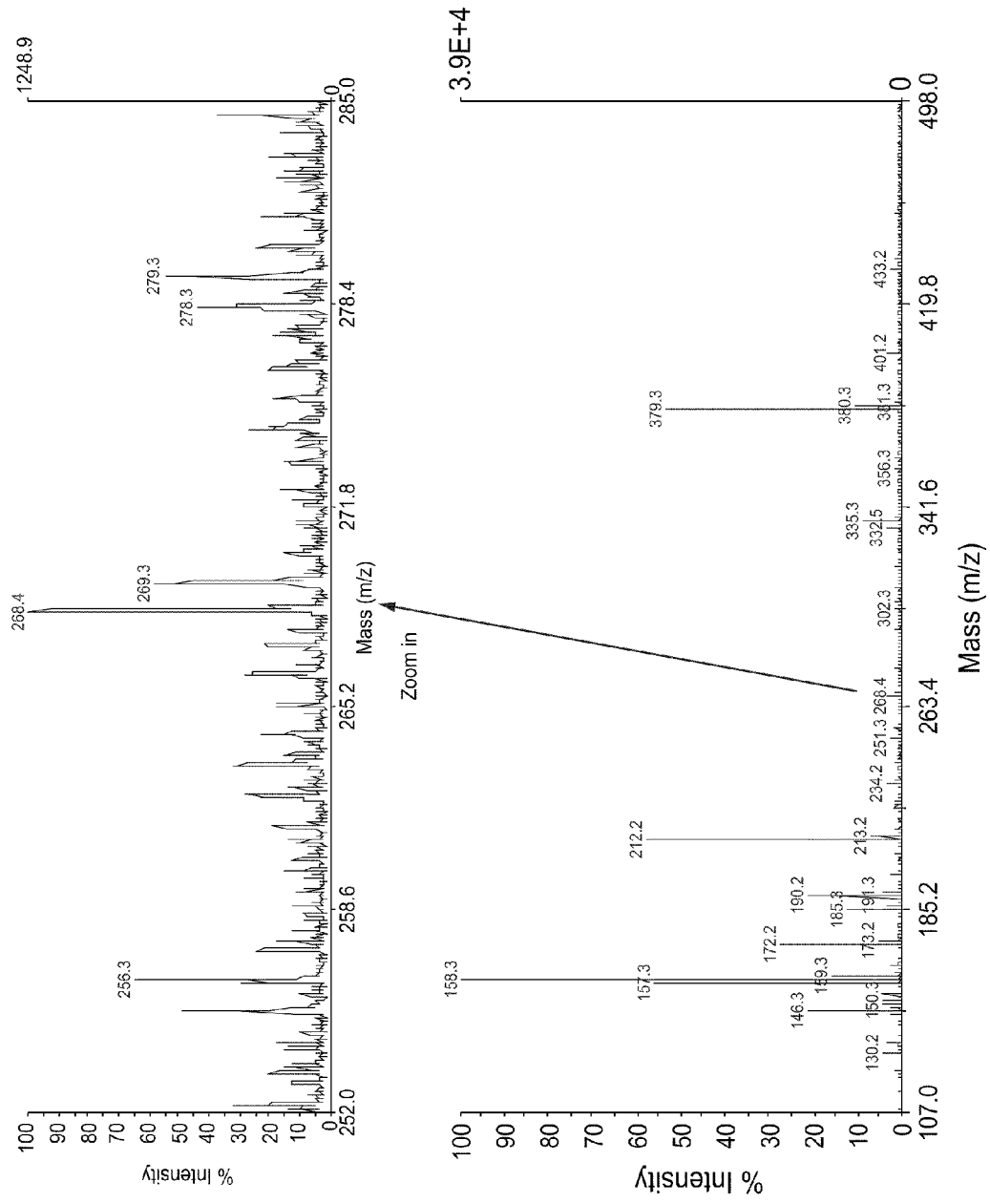
Figure 5F:
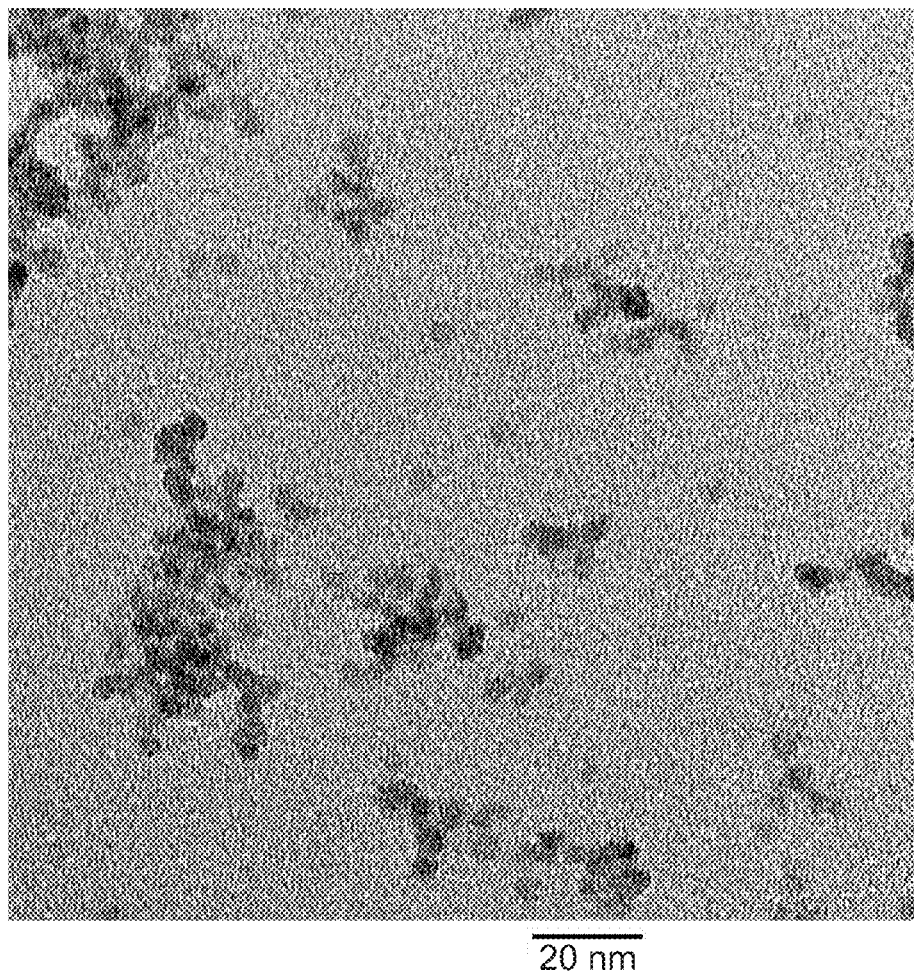
Figure 5G:
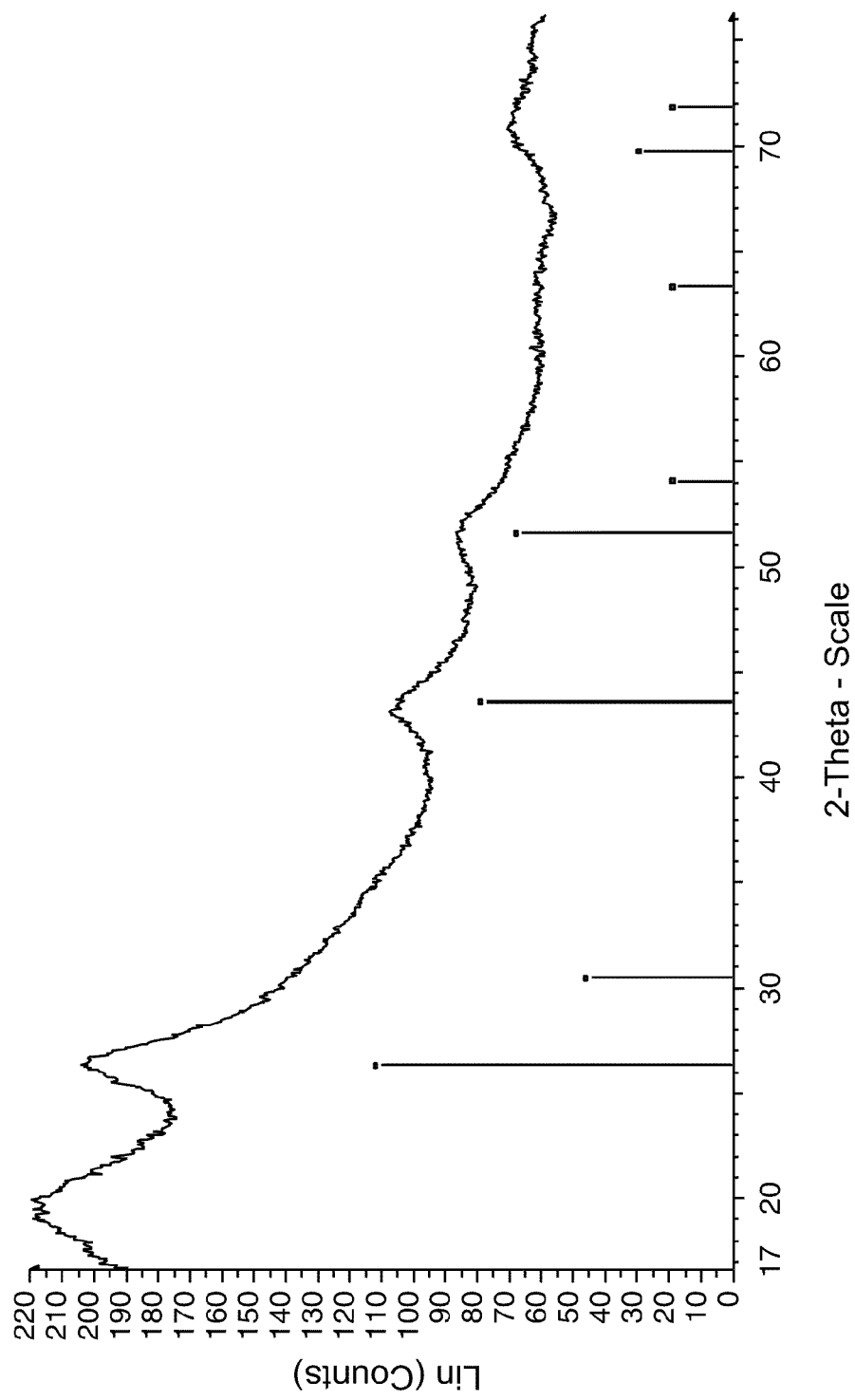
Figure 6A:
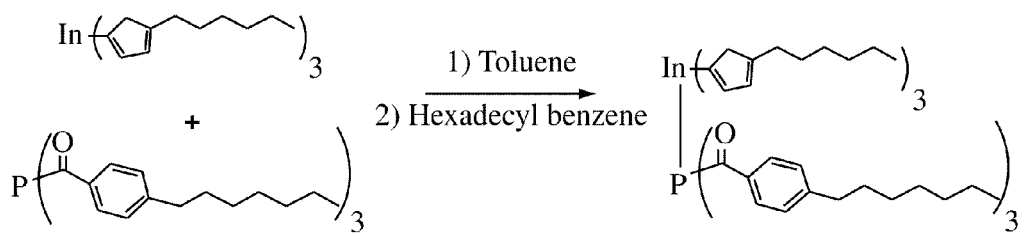
FIG. 6 Panel A schematically illustrates formation of an In—P complex. Panel B presents the reaction temperature profile for a nanocrystal synthesis reaction. The reaction pot contains 0.4 mmol of $PPh_3$, 0.4 mmol of stearic acid, and 7.0 mL of HDB (hexadecylbenzene). Panels C and D show micrographs of the resulting InP nanocrystals. Panel E presents results of XRD analysis of the resulting InP nanocrystals. Panel F shows a UV-visible absorption spectrum of the resulting InP nanocrystals.
Figure 6B:
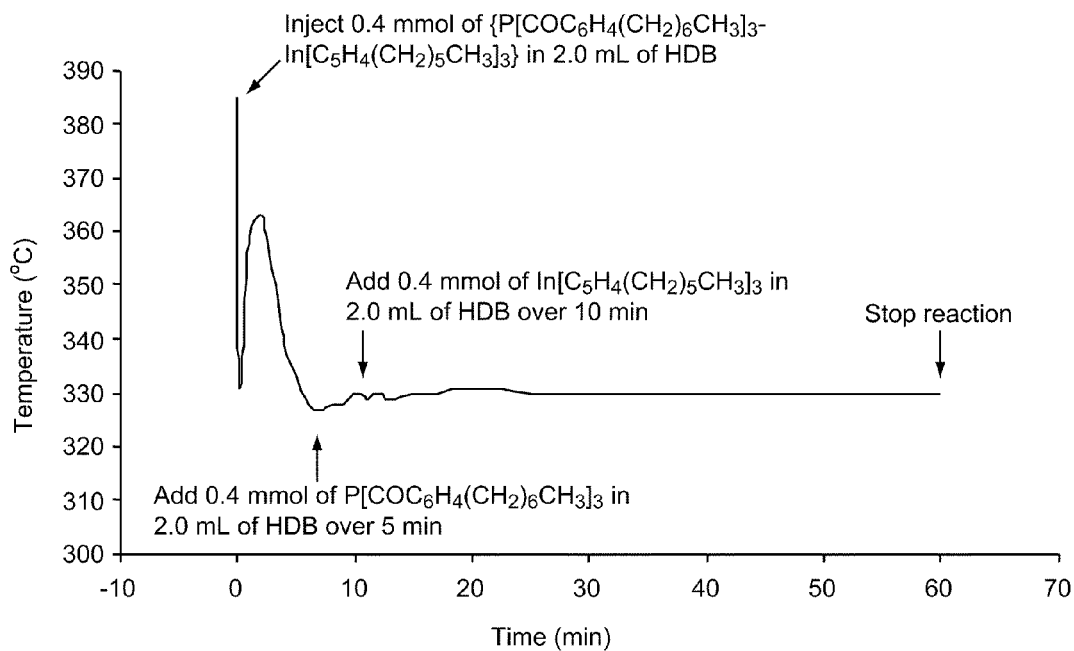
Figure 6C:
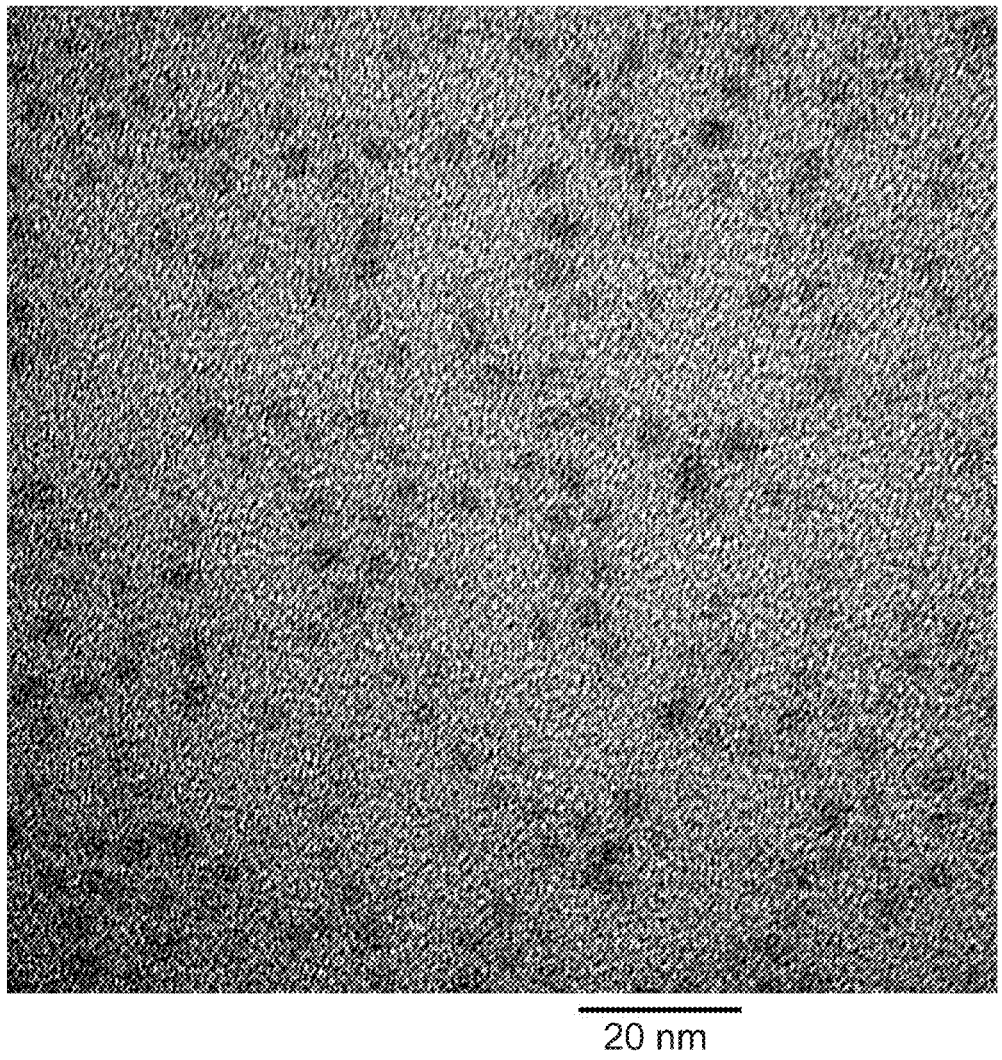
Figure 6D:
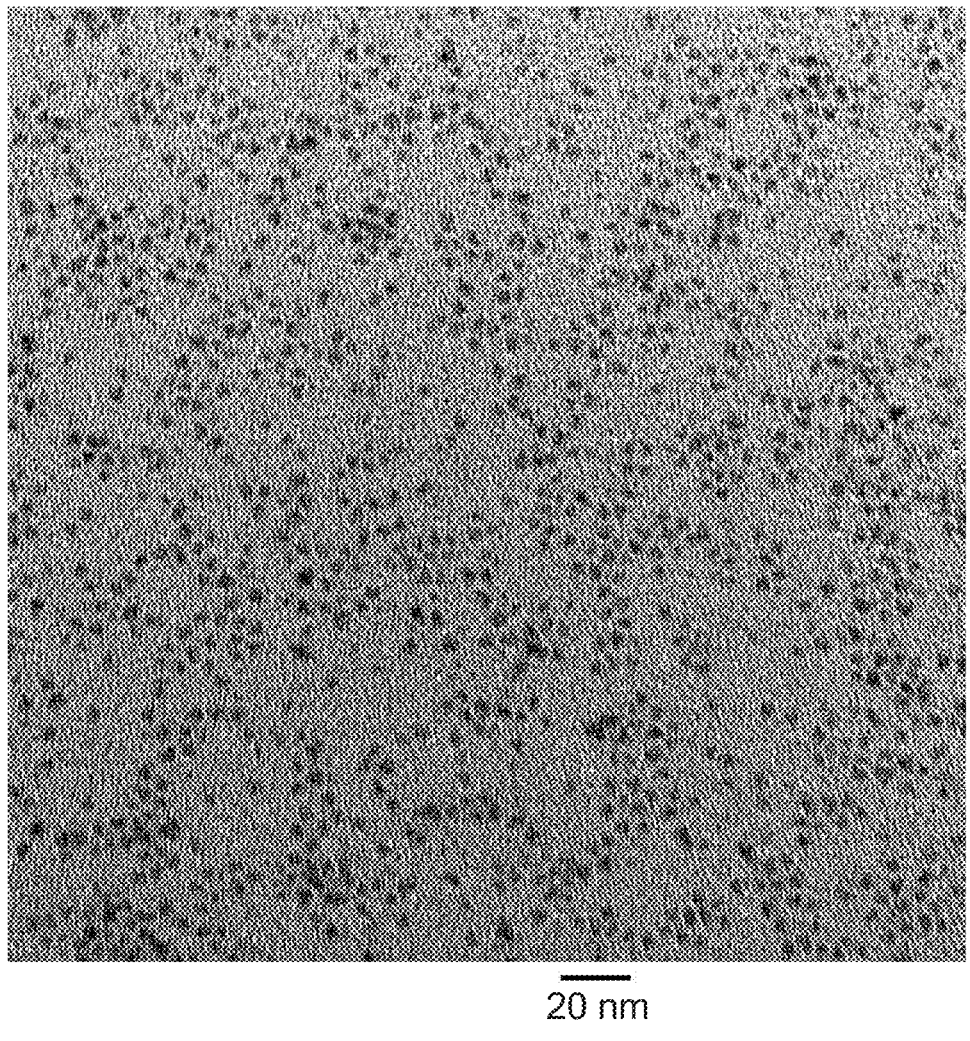
Figure 6E:
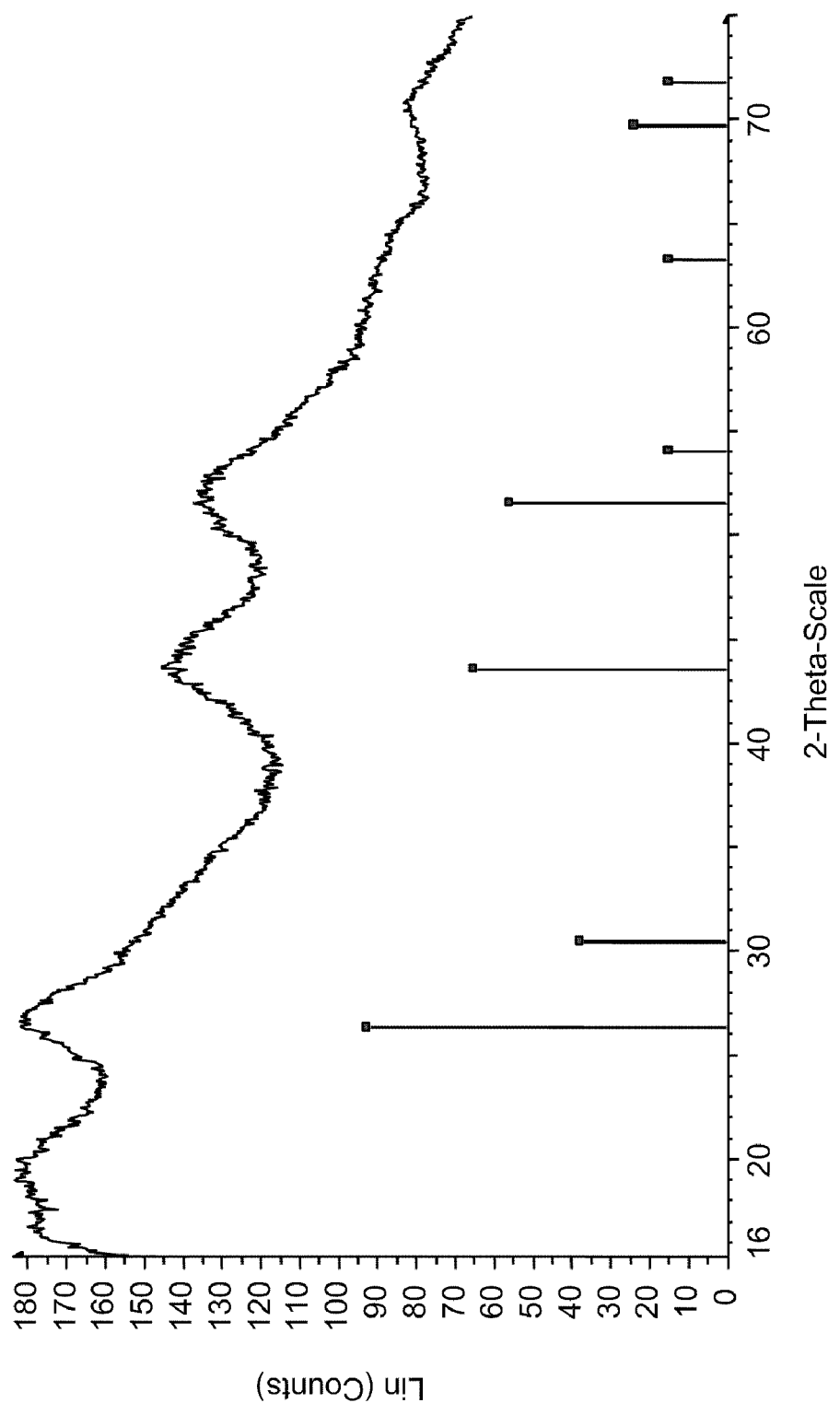
Figure 6F:
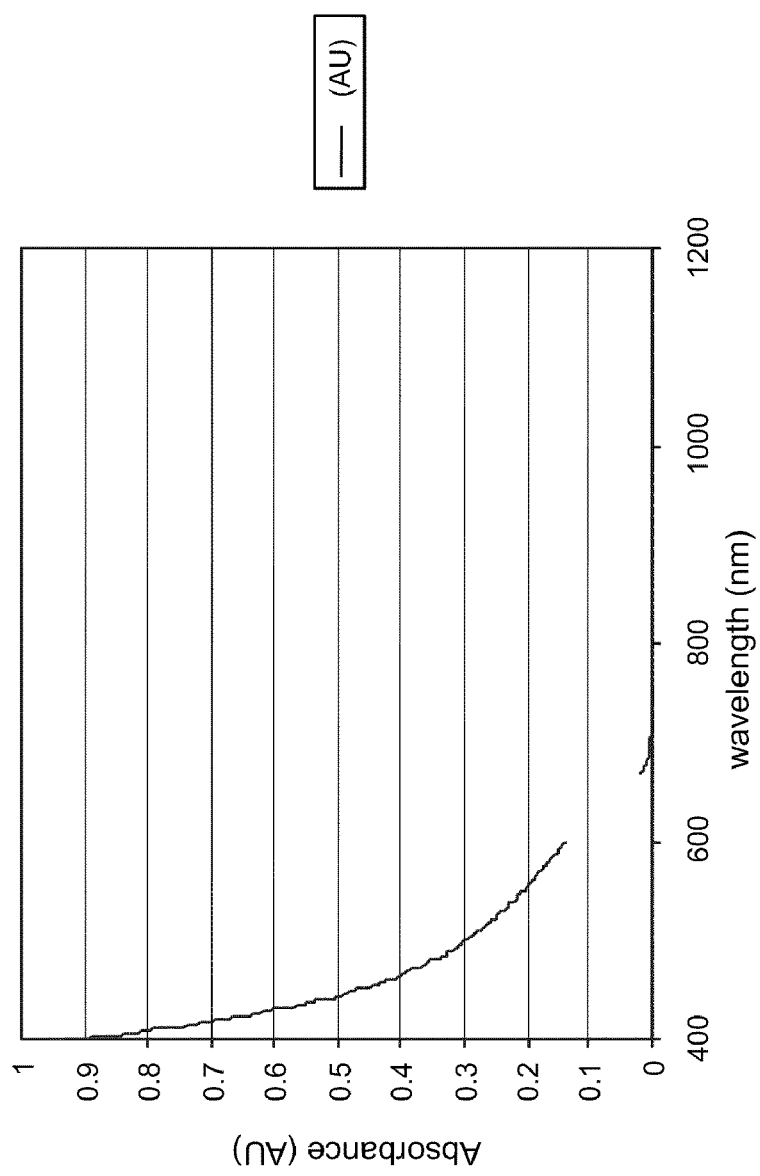
Figure 7B:
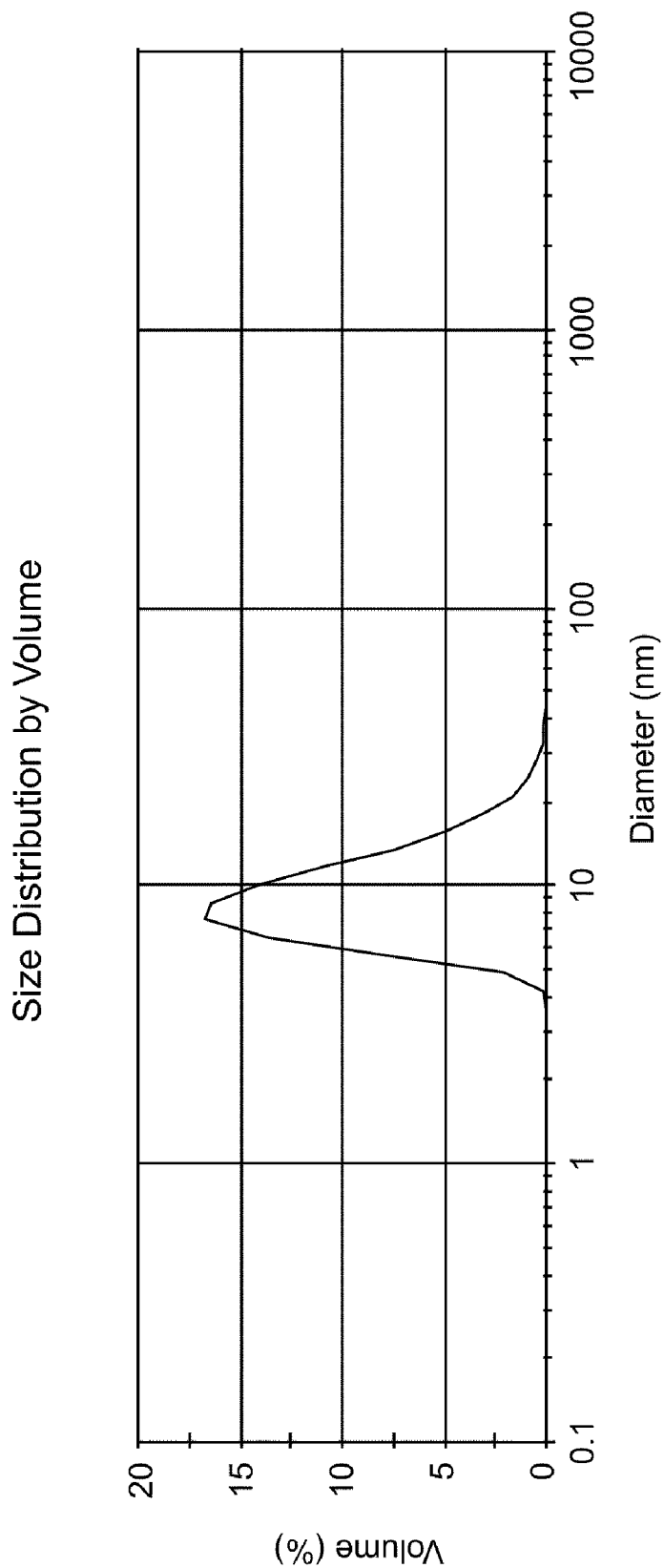
FIG. 7 Panel A presents the reaction temperature profile for a nanocrystal synthesis reaction. Panel B shows dynamic light scattering data indicating the size of the resulting nanostructures. Panel C shows a UV-visible absorption spectrum of the resulting InP nanocrystals. Panel D shows transmission electron micrographs of the resulting tetrahedral nanocrystals. Panel E presents results of XRD analysis of the resulting InP nanocrystals. Panel F presents the reaction temperature profile (temperature vs. time) for a nanocrystal synthesis reaction. Panel G shows a UV-visible absorption spectrum of the resulting InP nanocrystals. Panel H shows transmission electron micrographs of the resulting tetrahedral nanocrystals. Panel I presents results of XRD analysis of the resulting InP nanocrystals.
Figure 7C:
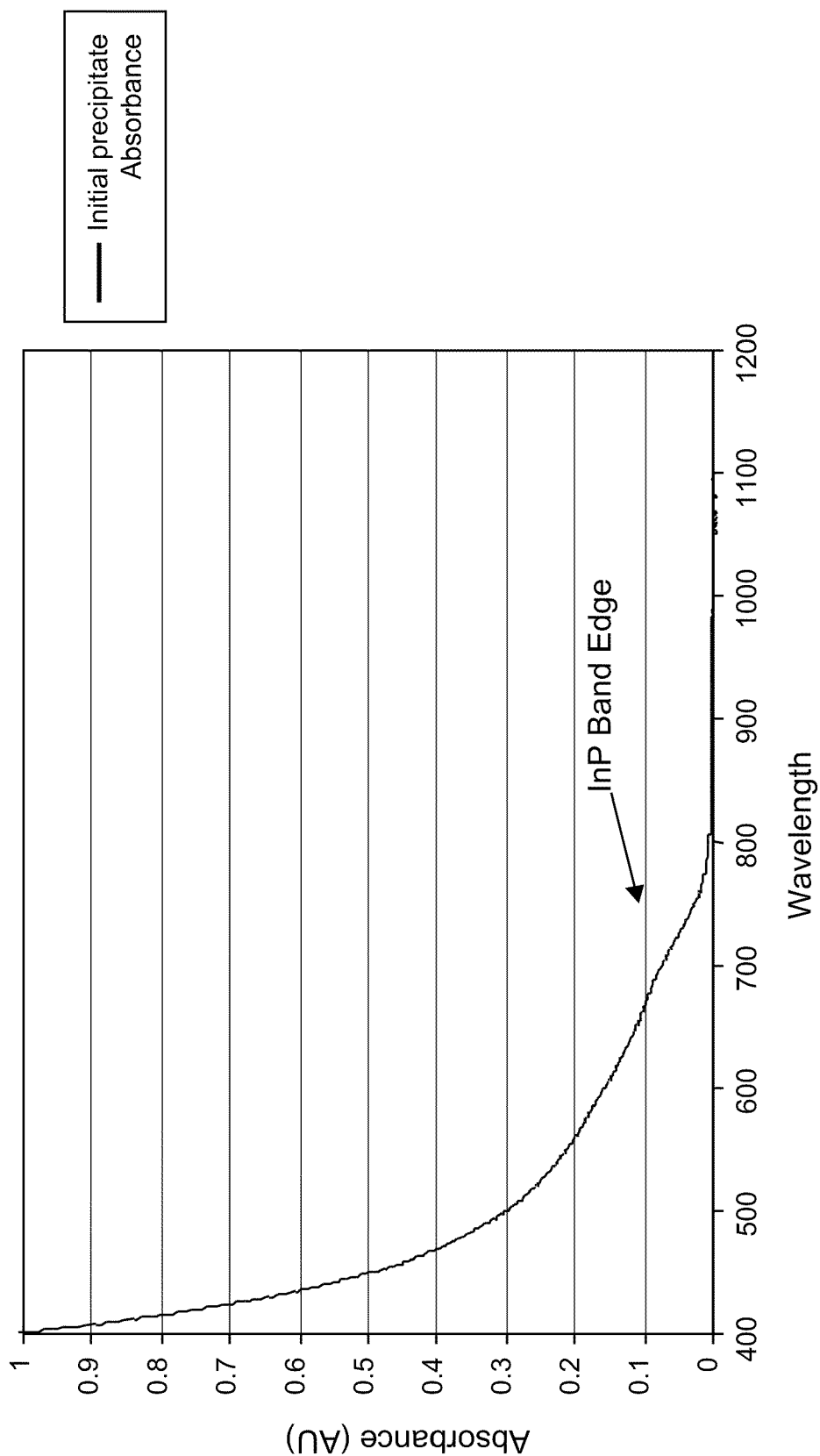
Figure 7D:
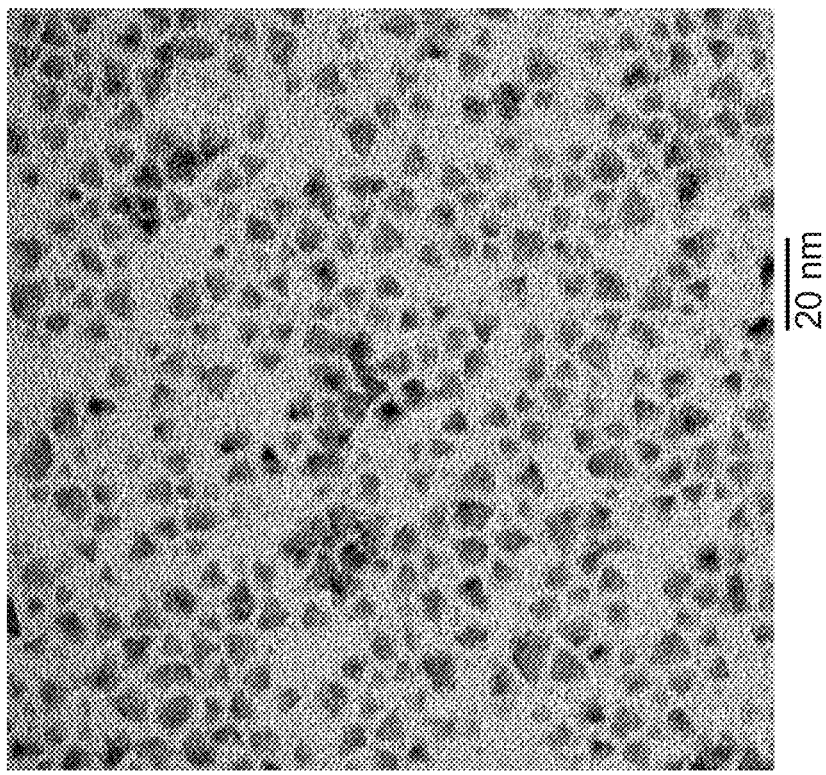
Figure 7D:
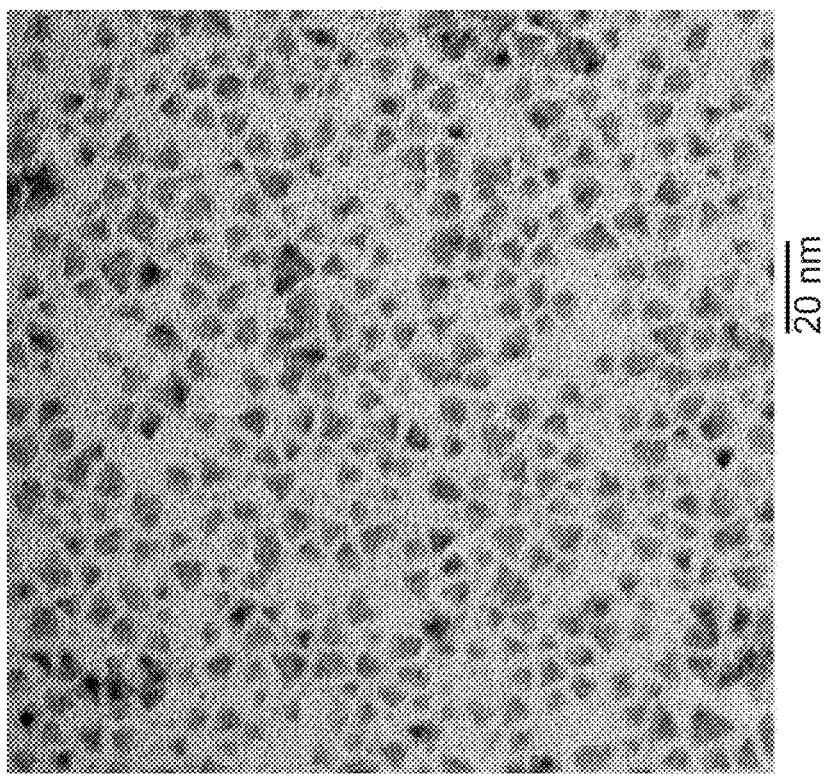
Figure 7E:
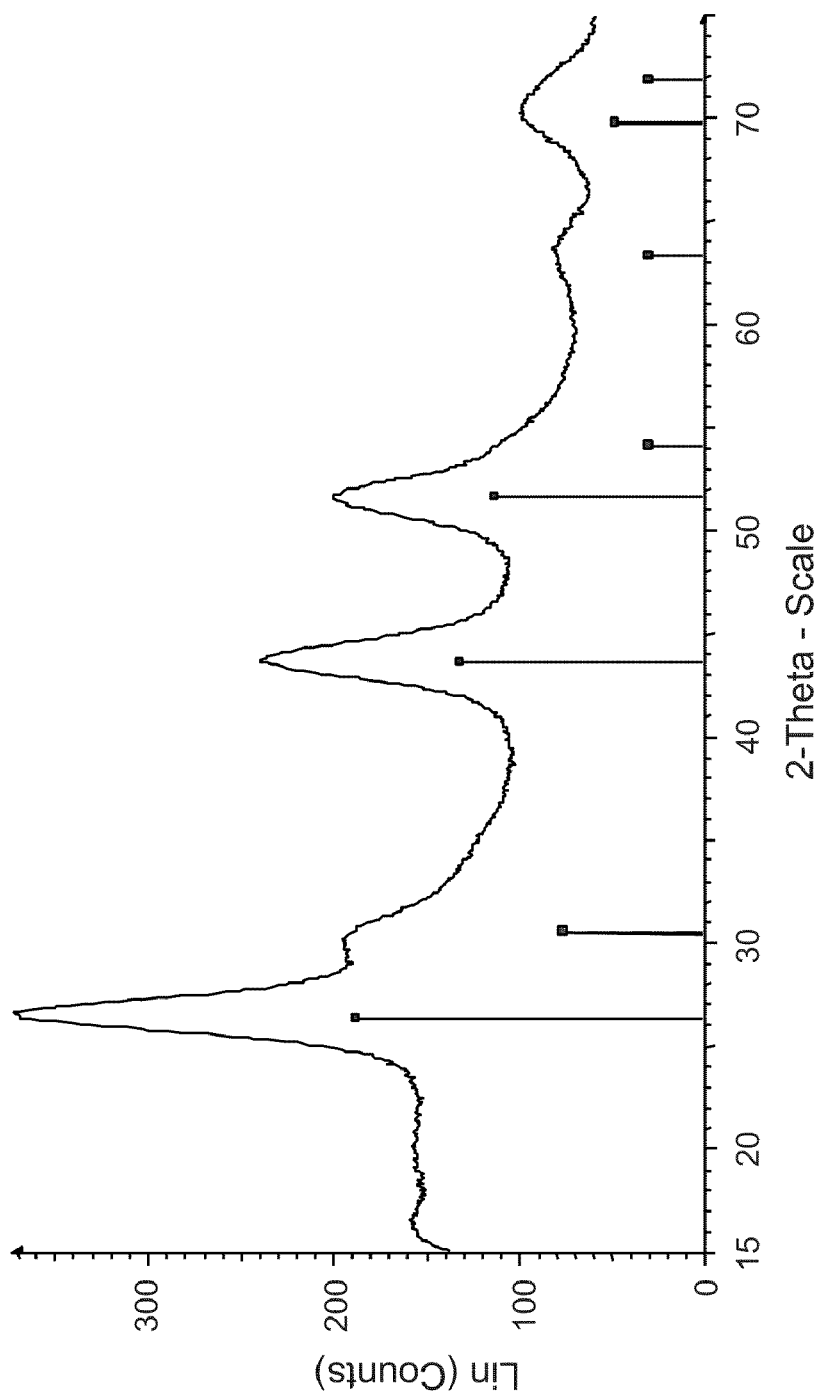
Figure 7F:
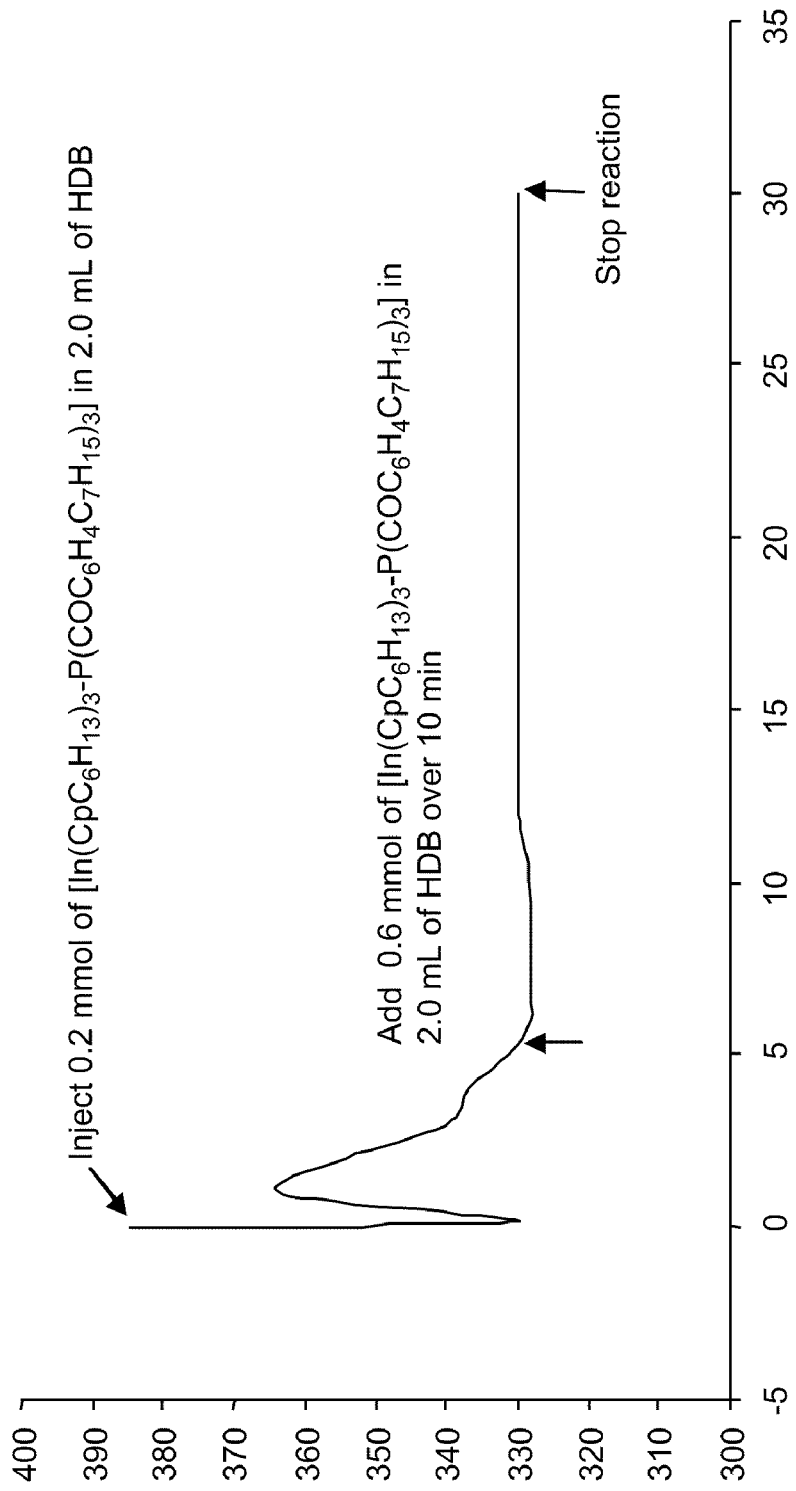
Figure 7G:
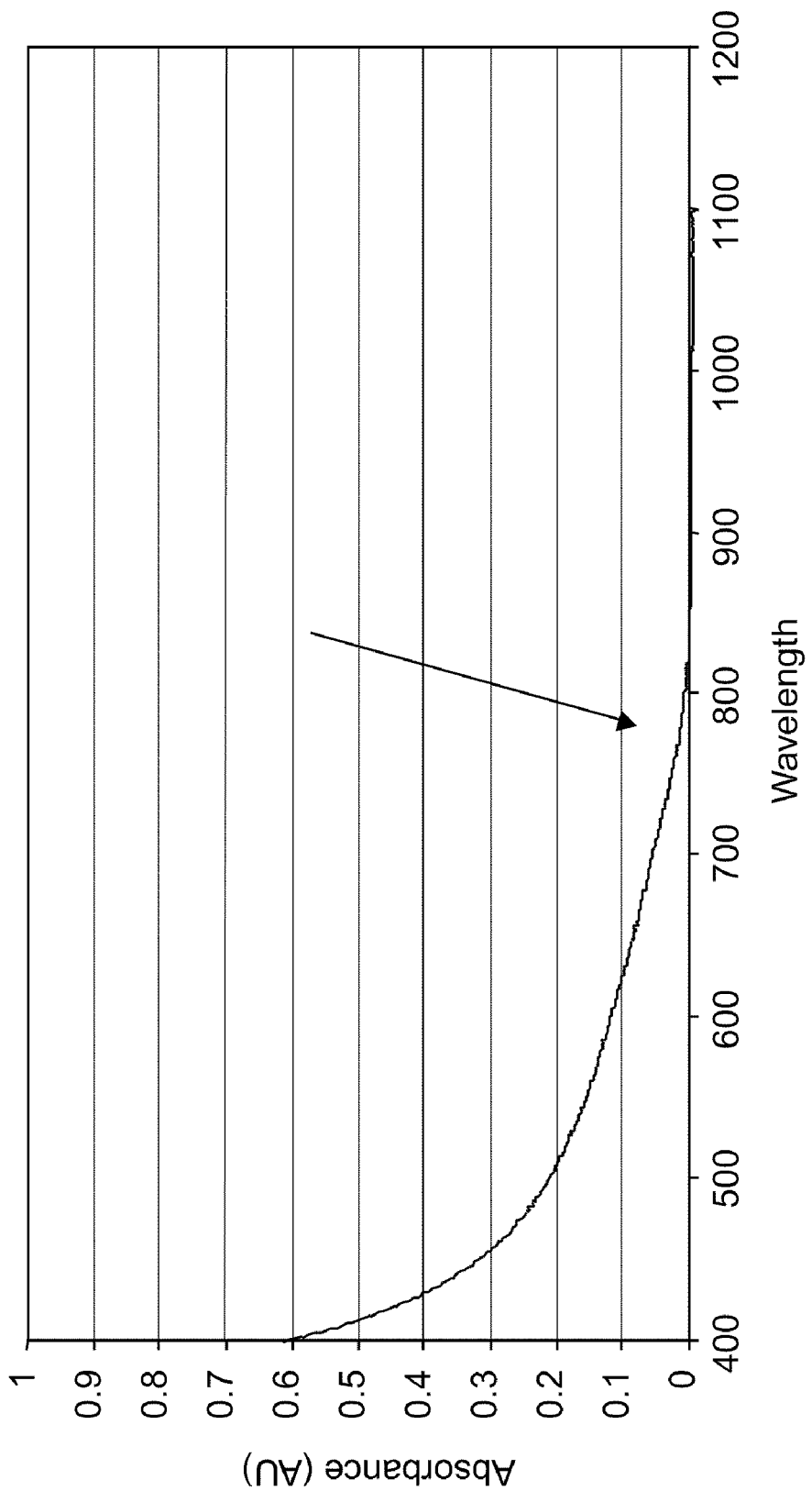
Figure 7H:
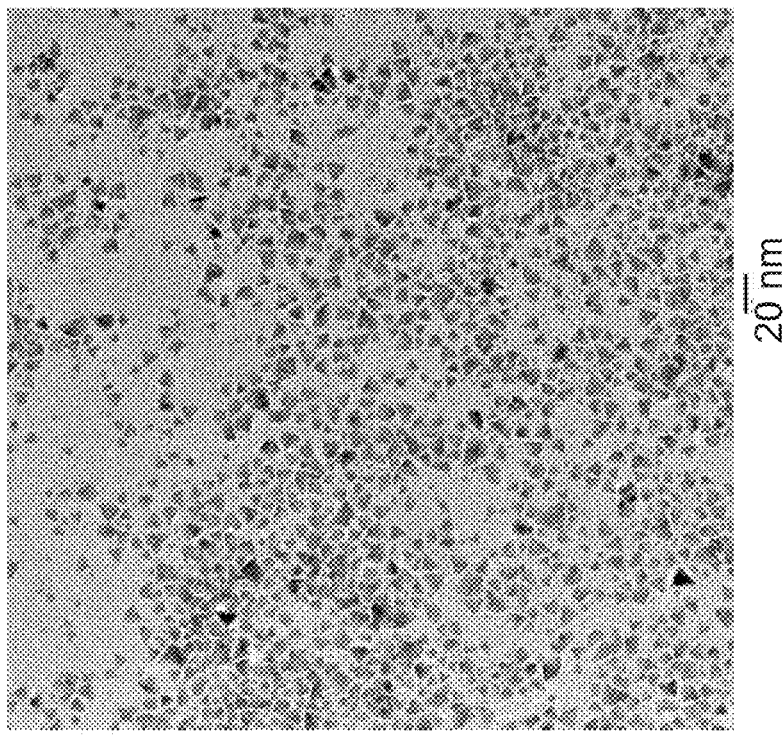
Figure 7H:
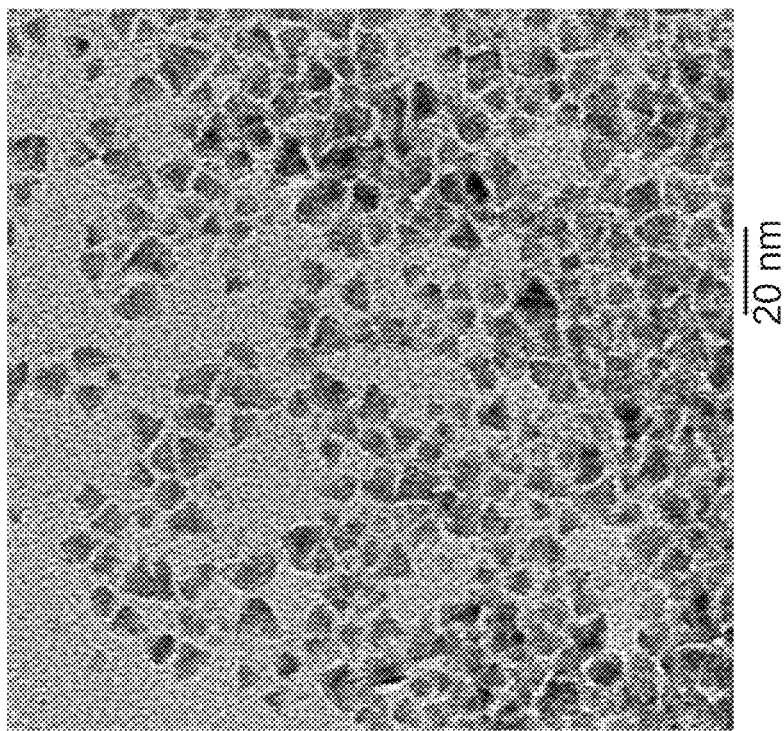
Figure 7I:
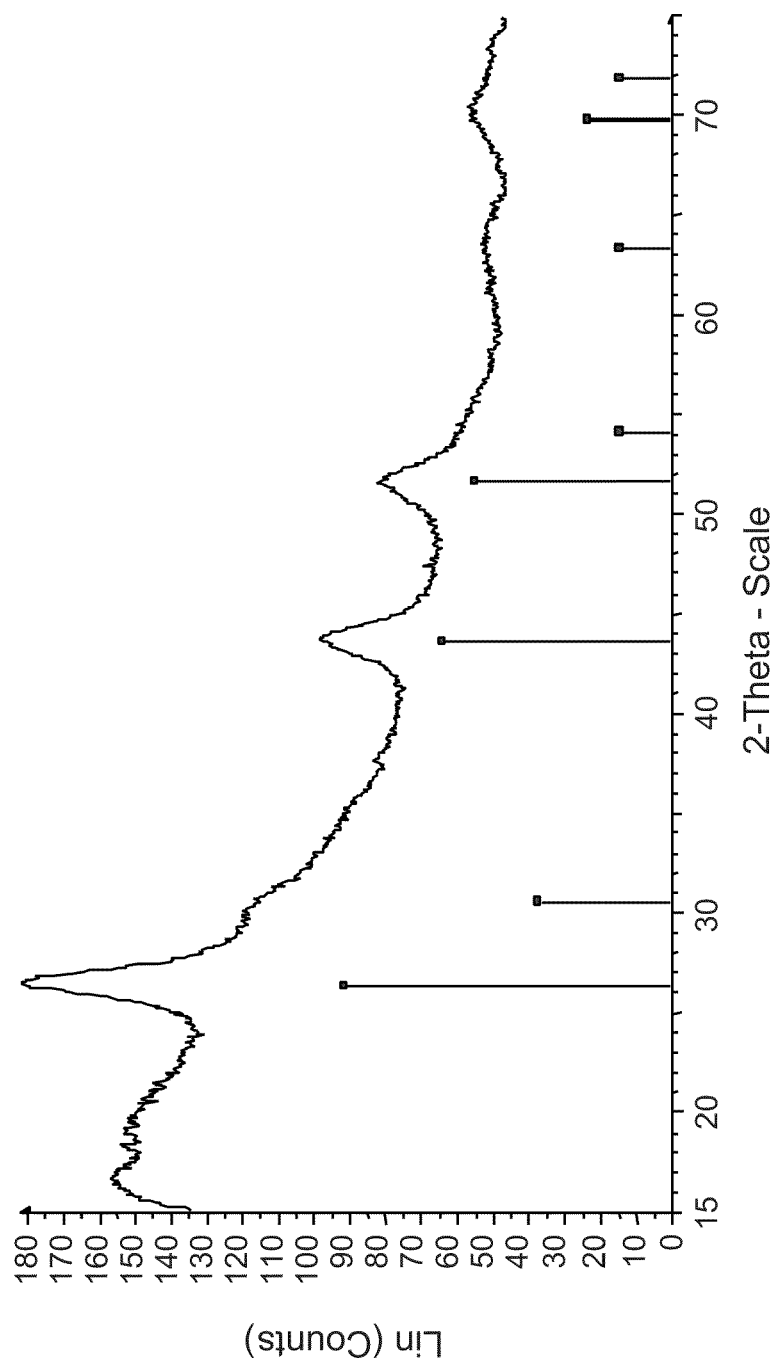

Although the scope of the present invention is not intended to be limited to any particular mechanism, FIG. 1 compares two possible mechanisms for reaction of a tribenzylphospine first precursor with an InCl₃ second precursor (sigma bond metathesis in Panel A and pseudo SN2 in Panel B). Panel C depicts an example tribenzylphospine substituted with an electron withdrawing group (EWG), e.g., F or CF₃; the presence of such an electron withdrawing substituent can, e.g., accelerate the reaction illustrated in Panel A.

In another related class of embodiments, the first precursor comprises a Group V atom substituted with three carboxamide groups. Thus, for example, the first precursor can be a tricarboxamide phosphine, e.g., N,N,N,N,N,N-hexaethylphosphine tricarboxamide. Without limitation to any particular mechanism, reaction of N,N,N,N,N,N-hexaethylphosphine tricarboxamide with an indium halide, indium phosphonate, indium carboxylate, or the like to form InP nanocrystals is schematically illustrated in FIG. 1 Panel D.

In another class of embodiments, the first precursor comprises a trialkyl substituted Group V atom comprising a substituted and/or branched alkyl group. For example, the first precursor can include a tri-t-butyl substituted Group V atom; e.g., the first precursor can be tri-t-butylphosphine.

It is worth noting that WO 03/054953 by Alivisatos et al. suggests the use of precursors including a tri-alkyl substituted Group V atom; however, only n-alkyl substituents are described. Precursors with branched and/or substituted alkyl substituents on the Group V atom can unexpectedly work considerably better in nanostructure synthesis reactions, since they can react more quickly and/or form more stable by-products than do tri-n-alkyl substituted Group V atoms (e.g., tri-n-alkyl phosphines or arsines). Similarly, precursors with aryl substituents on the Group V atom (e.g., tribenzylphosphine) can also react more quickly and/or form more stable by-products than do tri-n-alkyl substituted Group V atoms (e.g., tri-n-alkyl phosphines).

In certain embodiments, the first precursor is a Group V inorganic compound. For example, in one class of embodiments, the first precursor comprises a Group V atom substituted with three carboxylate moieties or with three phosphinate moieties. In one embodiment, the Group V atom is P such that the first precursor is a phosphite ester.

The first precursor can be used in combination with essentially any suitable second precursor, whether previously known in the art or described herein. The Group III atom can be any atom selected from Group III of the periodic table of the elements. In a preferred class of embodiments, the Group III atom is B, Al, Ga, In, or Tl.

In one class of embodiments, the second precursor is a Group III inorganic compound (e.g., a Group III halide, or a compound in which the Group III atom is directly bonded to at least one oxygen atom or other heteroatom, e.g., nitrogen).

In one class of embodiments, the second precursor is a Group III halide (sometimes also referred to as a Group III halide compound). Thus, in this class of embodiments, the second precursor is YZ₃, where Y is a Group III atom (e.g., B, Al, Ga, In, or Tl) and Z is a halogen atom (e.g., F, Cl, Br, I, or At).

In another class of embodiments, the second precursor comprises one or more phosphonate, phosphinate, carboxylate, sulfonate, and/or boronate moieties bonded to the Group III atom. For example, the second precursor can comprise a bi- or tri-substituted Group III atom (e.g., a tricarboxylate, bi- or tri-phosphonate, or triphosphinate substituted Group III atom). Thus, in one class of embodiments, the second precursor is Y(alkylcarboxylate)₃, Y(arylcarboxylate)₃, Y(alkylphosphonate)₃, Y(arylphosphonate)₃, Y(alkylphosphonate)₂, Y(arylphosphonate)₂, Y(bialkylphosphinate)₃, or Y(biarylphosphinate)₃, where Y is B, Al, Ga, In, or Tl. The alkyl or aryl group can be, e.g., substituted or unsubstituted. For example, the second precursor can be an indium phosphonate or indium carboxylate (e.g., indium triacetate or indium tristearate).

In yet another class of embodiments, the second precursor is a Group III metal oxide. For example, the second precursor can be indium oxide or gallium oxide. As another example, the second precursor can be a Group III alkoxy or Group III aryloxy (e.g., a Group III phenoxy, e.g., indium phenoxy). Reaction of indium phenoxy as the second precursor with a triacylphosphine first precursor to eliminate an ester co-product and form InP nanocrystals is depicted in FIG. 2 Panel E. Synthesis of Group III alkoxys, e.g., indium alkoxys, has been described. For example, general indium alkoxys have been described in Bradley et al. (1990) Polyhedron 9(5):719-726; Bradley et al. (1988) J. Chem. Soc. Chem. Comm. (18):

1258-1259; and Chatterje et al. (1976) Journal of the Indian Chemical Society 53(9):867, while alkoxyIndium with electron withdrawing groups is described in Miinea et al. (1999) Inorg. Chem. 38:4447.

In one class of embodiments, instead of being a Group III inorganic compound, the second precursor is a Group III organometallic compound. In some embodiments, the second precursor comprises a tri-substituted Group III atom in which the three substituents are independently any organic group or hydrogen. For example, the second precursor can be an alkyl metal or a trialkyl metal, e.g., trimethyl indium or triethyl indium. In one aspect, the second precursor comprises a Group III atom substituted with three unsaturated groups (e.g., any group including at least one double or triple bond or ring, including, but not limited to, alkenyl, alkynyl, acyl, and aryl groups). For example, the second precursor can be triallyl indium, trivinyl indium, tributadiene indium, trialkylethynyl indium, trialkylethenyl indium, tri-4-phenylethynyl indium, or trialkylphenylethynyl indium. In other embodiments, the second precursor comprises a Group III atom substituted with three cyclic ketone groups; for example, the second precursor can be tris-alpha-cyclohexanone indium (III). In yet other embodiments, the second precursor comprises a Group III atom substituted with three cyclopentadienyl or substituted cyclopentadienyl groups. For example, the second precursor can be an indium tris-Cp compound or an indium tris-(substituted Cp) compound, for example, tris-cyclopentadienyl indium(III) or tris(n-hexyl cyclopentadienyl) indium(III). Preparation of such tri-unsaturated Group III compounds is known in the art; see, e.g., Schiefer et. al. (2003) Inorg. Chem. 42:4970 for a description of preparation of Group III tris-(ethynyl)indium compounds.

Reaction of tris-alpha-cyclohexanone indium (III) as the second precursor with a triacylphosphine first precursor to form an ester and InP nanocrystals is illustrated in FIG. 2 Panel A. Without intending to be limited by any particular mechanism, the key step is the dative bond between indium and phosphorous, an interaction that forms a precursor to the nanocrystal. With this interaction, electron donation from phosphorous to indium will make the indium electron rich and should promote bond breaking of indium-carbon bonds to the ligands, especially if the anion formed as the result of the reaction is relatively stable. That anion should attack electrophiles, intra or intermolecularly, especially one held in immediate proximity, such as a carbonyl carbon. Therefore a possible elimination mechanism could be the one shown in FIG. 2 Panel B that results in the formation of an ester. Overall, it is formation of an enol by breakage of the indium-carbon bond followed by attack by oxygen on the electrophilic carbon of the acyl phosphine, as shown in Panel B. The enol is stabilized by two significant resonance forms with negative charge on carbon or on oxygen. Synthesis of molecules similar to tris-alpha-cyclohexanone indium (III) has been described, e.g., in Lehmann et al. Org. Lett. 5(14):2405, Boeckman et al. (1977) Tetrahedron Lett. 18:4187, and Boeckman et al. (1981) Tetrahedron 37:3997 (tris-(dihydropyranyl)In(III) synthesis) and is illustrated in FIG. 2 Panel C. Tris-alpha-cyclohexanone indium (III) can be synthesized through a similar process, as illustrated in Panel D, for example. See also Lehmann et al. (2003) Org. Lett. 5:2405 for synthesis of an organometallic In compound with cyclic hydrocarbon ligands containing oxygen (In(DHP)$_3$).

As another example, without intending to be limited by any particular mechanism, reaction of tris-cyclopentadienyl indium(III) (InCp$_3$) as the second precursor with a triacylphosphine first precursor, e.g., by elimination of a cyclopentadieneide anion, is illustrated in FIG. 2 Panel F. Alternatively or in addition, this reaction may occur through a Diels-Alder cycloaddition between the acyl group of the phosphine and the cyclopentadiene ring of the indium-containing second precursor, e.g., depending on reaction temperature and light (described for ruthenium compounds in Ji et al. (1992) Organometallics 11:1840-1855). The synthesis of InCp$_3$ and substituted Cp derivatives has been described, e.g., in Beachley et al. (2002) Organometallics 21:4632-4640 and Beachley et al. (1990) Organometallics 9:2488.

In general, without intending to be limited by any particular mechanism, unsaturated substituents on the P or other Group V element can result in cycloadditions, thus changing the bonding character between the Group III and Group V atoms. Group V precursors that contain unsaturated moieties bonded to the Group V atom can promote pi-backbonding from the late metal indium or other Group III atom to the Group V atom, thus strengthening the III-V interaction and weakening bonds to the moieties attached to the Group III and V atoms. This can result in enhanced cleavage of organometallic bonds to the indium or other Group III metal center.

In one class of embodiments, the first precursor comprises a trisubstituted Group V atom where the substituents are dienes, while the second precursor includes a trisubstituted Group III atom where the substituents are dienophiles. In a related class of embodiments, the first precursor comprises a trisubstituted Group V atom where the substituents are dienophiles while the second precursor includes a trisubstituted Group III atom where the substituents are dienes. The diene and dienophile substituents can, e.g., undergo Diels-Adler reactions. See, e.g., Yang and Chan (2000) J. Am. Chem. Soc. 122:402-403, which describes a Diels-Adler reaction involving indium(I) with elimination of Cp, and Ji et al. (1992) Organometallics 11:1840-1855, and examples herein.

As will be evident, the first and second precursors described herein can be used in any of a variety of combinations. To list only a few examples, the first precursor can include a triacyl substituted Group V atom while the second precursor includes a Group III atom substituted with three unsaturated groups; for example, the first precursor can be tribenzoylphosphine and the second precursor tris-cyclopentadienyl indium, the first precursor tri-heptylbenzoylphosphine and the second precursor tris-cyclopentadienyl indium, or the first precursor tri-heptylbenzoylphosphine and the second precursor tris-hexylcyclopentadienyl indium.

Another example precursor combination is illustrated in FIG. 1 Panel E. In this example, the first precursor comprises a Group V atom substituted with three carboxylate moieties, and the second precursor comprises a Group III atom substituted with three carboxylate moieties. (In similar examples, one or both precursors can instead include three phosphinate moieties.) The precursors can, for example, be reacted in the presence of a non-coordinating solvent (e.g., hexadecylbenzene), an oxygen scavenger (e.g., a pi-acid oxide acceptor such as triphenylphosphine), and/or a surfactant (e.g., an alkyl-substituted carboxylic, phosphonic, phosphinic, or sulfonic acid, or a combination thereof, which can promote thermodynamic equilibrium and/or associate with a surface of the resulting nanocrystals, e.g., stearic acid). Example reactions for synthesis of these first and second precursors is outlined in FIG. 1 Panels F and G, respectively. Without intending to be limited to any particular mechanism, it is thought that III and V precursors such as these inorganic esters can reversibly decompose into III-V nanocrystals and that such promotion of thermodynamic equilibrium can increase quality and facilitate shape control of the resulting nanocrystals.

The first and second precursors are typically reacted in the presence of at least one surfactant. For example, the precursors can be reacted in the presence of a first surfactant, a second surfactant, or a mixture of first and second surfactants.

The first surfactant is typically (but not necessarily) one that interacts relatively weakly with the surface of the nanostructures and/or the precursors. Suitable first surfactants include, but are not limited to, tri-n-alkyl phosphines (e.g., TOP and tri-n-butyl phosphine (TBP)), tri-n-alkyl phosphine oxides (e.g., TOPO), alkyl amines (e.g., monoalkyl amines and bialkyl amines, or trialkyl amines such as trioctylamine), and alkyl- and/or aryl-thiols. Suitable first surfactants also include unsaturated Group V derivatives; the first surfactant can comprise a Group V atom substituted with three unsaturated groups (e.g., alkenyl or alkynyl groups). Examples include trisalkylphenylethynylphosphines, e.g., tri(ethynylbenzene-hexyl)phosphine, tris(ethynylbenzene-pentyl)phosphine, and the other unsaturated phosphines noted herein. As just one specific example, a trialkoyl phosphine can be used as the Group III precursor and tri(ethynylbenzene-hexyl)phosphine as the first surfactant, since the trialkoyl phosphine will react at a lower temperature than the tri(ethynylbenzene-hexyl)phosphine will.

A suitable surfactant is typically a liquid at the temperature at which the nanostructures are grown (and at the nucleation temperature, if it is different than the growth temperature). Additionally, the surfactant should be stable at the growth temperature (and the nucleation temperature, if higher). Surfactants that can withstand higher temperatures, e.g., long chain tri-n-alkyl phosphines, are thus preferable in some embodiments. In one class of embodiments, the first surfactant is a C12-C30 tri-n-alkyl phosphine, e.g., tri-n-dodecyl phosphine or tri-n-hexadecyl phosphine. Synthesis of such long chain alkyl phosphines is described in, e.g., Franks et al. (1979) "The preparation and properties of tertiary phosphines and tertiary phosphine oxides with long alkyl chains" J. Chem. Soc., Perkin 1 3029-3033.

The second surfactant, as noted, can be used whether a first surfactant is used or not; when a combination of first and second surfactants is used, the second surfactant is typically (but not necessarily) one that adsorbs differently to different crystallographic faces of the nanostructure and/or that adsorbs differently than does the first surfactant. Suitable second surfactants include, but are not limited to, alkyl amines (e.g., mono-, bi-, and tri-alkyl amines; typically, the first surfactant is not also an alkyl amine) and phosphonic acids (e.g., a C2-30 alkylphosphonic acid), phosphinic acids (e.g., a C2-30 bialkylphosphinic acid), carboxylic acids (e.g., a C2-30 alkylcarboxylic acid), boronic acids, and sulfonic acids, as well as deprotonated forms or condensates thereof. It will be evident that not all possible combinations of surfactants are suitable for use; for example, mixing an amine surfactant with an acid surfactant can produce a salt (e.g., an insoluble salt), in which case the surfactants are typically not used in combination with each other.

The first and second precursors can optionally be reacted in the presence of at least one non-coordinating solvent (and, preferably, also in the presence of one or more surfactants, unless one of the precursors can also function as a surfactant). Preferred solvents include those with a boiling point greater than 100° C. Suitable non-coordinating solvents include long chain alkanes or alkenes, alkane substituted aryl derivatives, and the like. For example, hexadecane, octadecane, octadecene, phenyldodecane (also called dodecyl benzene), phenyltetradecane (also called tetradecylbenzene), or phenylhexadecane (also called hexadecylbenzene) can be used.

Thus, in one class of embodiments, the first and second precursors are reacted in the presence of a non-coordinating solvent, e.g., an alkane or an alkene, e.g., hexadecane, octadecane, octadecene, phenyldodecane, phenyltetradecane, or phenylhexadecane.

In one class of embodiments, the first and second precursors are reacted in the presence of the non-coordinating solvent and a first and/or second surfactant (e.g., any of those described herein). For example, the first and second precursors can be reacted in the presence of the non-coordinating solvent (e.g., phenylhexadecane) and a carboxylic acid (e.g., stearic acid), and optionally also in the presence of a sacrificial oxide acceptor (e.g., triphenylphosphine).

It is worth noting that, in certain embodiments, the same substance can serve as both a precursor and a surfactant. For example, a trialkoyl phosphine, a triaroyl phosphine, a trialkyl phosphine (e.g., TOP), or the like, can serve as both a Group III precursor and a surfactant in a nanostructure synthesis reaction. See, e.g., Example 7 herein.

Suitable reaction conditions (e.g., choice of precursors and surfactant(s), ratio of surfactants, ratio of precursors and surfactants, ratio of precursors to each other, concentration of precursors, and temperature) can be empirically determined as is known in the art to produce the desired size and/or shape nanostructures from the reaction.

As briefly described above for growth of Group II-VI semiconductor nanostructures, using a mixture of surfactants, varying the ratio of the surfactant(s) to the precursors, and/or varying the ratio of the precursors to each other permits the shape and/or size of the resulting nanostructures to be controlled.

Thus, in one class of embodiments, reacting the first and second precursors comprises reacting the first and second precursors in the presence of at least a first surfactant and a second surfactant, whereby the shape of the nanostructures produced is capable of being controlled by adjusting the ratio of the first and second surfactants. For example, the ratio of the first and second surfactants can be adjusted to produce substantially spherical nanocrystals, nanorods, branched nanostructures, and/or nanotetrapods. For example, in certain embodiments, increasing the ratio of the second surfactant to the first surfactant can result in growth of nanorods or nanotetrapods, primarily or exclusively, rather than spherical nanocrystals.

Additional surfactants can also be used to help control the shape of the resulting nanocrystals. Thus, in some embodiments, the first and second precursors are reacted in the presence of a first surfactant, a second surfactant, and a third surfactant (e.g., a mixture of TOPO, hexyl phosphonic acid, and tetradecyl phosphonic acid). Fourth, fifth, etc. surfactants are optionally also used.

In a related class of embodiments, reacting the first and second precursors comprises reacting the first and second precursors in the presence of a second surfactant, whereby the shape of the nanostructures produced is capable of being controlled by adjusting the ratio of the second surfactant and the first or second precursor. For example, the ratio of the second surfactant and the first or second precursor can be adjusted to produce substantially spherical nanocrystals, nanorods, branched nanostructures, and/or nanotetrapods.

In another related class of embodiments, the ratio of the first and second precursors is adjusted to control the shape of the nanostructures produced. As for the embodiments above, the ratio of the first and second precursors can be adjusted to produce, e.g., substantially spherical nanocrystals, nanorods, branched nanostructures, and/or nanotetrapods.

Similarly, the concentrations of the first and second precursors can be adjusted to influence the shape of the nanostructures produced; for example, by increasing or decreasing the amount of each precursor initially provided, by introducing additional fresh first and/or second precursor as the reaction progresses, or the like.

It is worth noting that choice of first and second precursors can also affect the shape of the nanostructures produced by influencing the kinetics of the reaction. For example, the various Group III halides that are optionally used as second precursors in certain embodiments react at different rates; e.g., $InBr_3$ or $InI_3$ can react more quickly than $InCl_3$ with TOP to form InP nanostructures. Similarly, example first precursors tri-t-butylphosphine and tri-benzylphosphine can react more quickly than TOP and can thus increase the reaction rate. As one example, reactivity of the precursors can be finely regulated by electron donating and/or withdrawing substituents on groups substituting the Group III and/or Group V atoms; for example, a combination of an electron donating substituent on the acyl group of a tri-acyl substituted Group V atom and an electron withdrawing substituent on the substituted Group III atom can be used to control reaction kinetics and desired crystal growth.

Alternatively or in addition, the temperature can be controlled to control the shape and/or size distribution of the resulting nanostructures. Thus, in one class of embodiments, reacting the first and second precursors to produce the nanostructures includes heating at least one surfactant (e.g., a first and a second surfactant) to a first temperature; contacting the first and second precursors and the heated surfactant, whereby the first and second precursors react to form nuclei capable of nucleating nanostructure growth; and maintaining the first and second precursors, the surfactant, and the nuclei at a second temperature. The second temperature permits growth of the nuclei to produce the nanostructures, whereby the first and second precursors react to grow the nanostructures from the nuclei. The first (nucleation) temperature is typically greater than the second temperature, e.g., by about 40-80° C., about 20-40° C., about 10-20° C., about 5-10° C., or about 0-5° C.; the first and second temperatures can, however, be equal, or the first temperature can be less than the second temperature (e.g., by about 40-80° C., about 20-40° C., about 10-20° C., about 5-10° C., or about 0-5° C.). Different first and second temperatures can be used, e.g., to control the nucleation phase and growth phase separately (for example, a nanotetrapod can be produced by reacting precursors at a lower temperature to produce the zinc blende central region of the nanotetrapod, then increasing the temperature to promote wurtzite growth and produce the arms of the nanotetrapod).

Nucleation and/or growth at high temperatures may be necessary for use of certain precursors and/or desirable for producing certain nanostructure shapes. For example, under certain conditions, higher temperatures favor nanorod and nanotetrapod growth over spherical nanocrystal growth. Thus, in some embodiments, the first temperature is at least 300° C., at least 330° C., at least 360° C., at least 380° C., at least 400° C., or at least 420° C. In some embodiments, the second temperature is at least 250° C., at least 275° C., at least 300° C., at least 320° C., at least 340° C., at least 360° C., at least 380° C., at least 400° C., or at least 420° C. As noted previously, long chain tri-n-alkyl phosphines, for example, are optionally used as first surfactants at these higher temperatures.

As will be described in greater detail below, yield of nanostructures from the reaction is optionally increased by removal of one or more by-products during the reaction. Thus, in some embodiments, the first and second precursors react to produce the nanostructures and a by-product that has a boiling point or sublimation temperature that is less than the second temperature. The methods include removing at least a portion of the by-product as a vapor.

As noted, the precursors can be added either simultaneously or sequentially to a reaction vessel in which nanostructure synthesis is performed. The first and second precursors can, e.g., be injected separately into the reaction vessel (containing, e.g., a surfactant, solvent, and/or the like). Alternatively, the first and second precursors can be pre-mixed, e.g., in a suitable solvent, and permitted to form a complex (e.g., a Group III-V complex, e.g., an In—P complex, in which the In is coordinated by P), then introduced into the reaction vessel. See, e.g., Examples 7-9 herein.

Thus, in one class of embodiments, reacting the first and second precursors to produce the nanostructures includes contacting the first and second precursors, which form a Group III-V complex, e.g., in which the Group III atom is coordinated by a Group V atom. The Group III-V complex is then reacted to produce the nanostructures. The complex is optionally isolated after it is formed, and can, e.g., be stored (e.g., frozen) and reacted at a later time (e.g., by heating).

In one aspect, multiple precursors are used, e.g., to assist in controlling growth of the nanostructures. For example, in one class of embodiments, one set of precursors is used for nucleation of the nanostructures while another set of precursors is used for growth. As just one example, $InCp_3$ or $In(hexylCp_3)$ and tris(4-alkylbenzoyl)phosphine precursors are used for nucleation at or above room temperature, while $InCp_3$ and tris(4-alkylethynylbenzene)phosphine precursors are used for growth at a higher temperature (e.g., greater than 300° C.). Thus, reacting the first and second precursors to produce the nanostructures optionally includes reacting the first and second precursors to produce nuclei, providing a third precursor comprising a Group III atom and a fourth precursor comprising a Group V atom, and reacting the third and fourth precursors to produce the nanostructures from the nuclei.

In one class of embodiments, the first and second precursors are reacted in the presence of a sacrificial oxide acceptor, e.g., a substrate that accepts oxygen, e.g., a pi-acid such as triphenylphosphine or a substituted triphenylphosphine. Without intending to be limited to any particular mechanism, oxide growth on the surface of growing III-V nanocrystals can inhibit nanocrystal growth, decrease crystal quality, and/or interfere with shape control of the nanocrystals. Including an oxide acceptor in the synthesis reaction, e.g., a sacrificial and reversible oxide acceptor, can improve nanocrystal size, quality, and/or shape by promoting oxide transfer from the nanocrystal surface (e.g., by removing phosphine oxide from the surface of InP nanocrystals). It is worth noting that, in certain embodiments, the same substance can serve as both a sacrificial oxide acceptor and as a surfactant and/or precursor. It is also worth noting that such oxide acceptors can optionally be included in essentially any nanostructure synthesis reaction, not only in reactions including the Group III and/or V precursors of the invention.

Nanostructures produced by the methods herein can be incorporated into a photovoltaic device, LED, or nanocomposite, or can be used in essentially any other application in which semiconductor nanostructures are desired. The nanostructures can be modified after they are produced. For example, a shell is optionally added to the nanostructures to produce core-shell nanostructures, or any surfactant(s) coating the nanostructures can be exchanged for other surfactants or surface ligands.

The nanostructures produced by the methods can be essentially any shape and/or size. For example, the resulting nanostructures can include nanocrystals, substantially spherical nanocrystals, nanorods, branched nanostructures, and/or nanotetrapods. Similarly, the nanostructures can comprise essentially any Group III-V semiconductor, including, but not limited to, InN, InP, InAs, InSb, GaN, GaP, GaAs, GaSb, AlN, AlP, AlAs, or AlSb. The Group III-V semiconductor optionally includes more than one Group III and/or Group V atom; for example, the nanostructures can comprise GaAsP or InGaAs. Thus, the methods optionally include providing a third precursor comprising a Group III or Group V atom and reacting it with the first and/or second precursors.

As noted, nanostructure nucleation and/or growth at high temperatures can be desirable for use of certain precursors and/or for producing certain nanostructure shapes. Thus, one general class of embodiments provides high temperature methods for production of Group III-V semiconductor nanostructures. In the methods, a first precursor and a second precursor are provided. The first and second precursors are reacted at a first temperature of at least 300° C. to produce the nanostructures. The first precursor comprises a trisubstituted Group V atom, where the three substituents on the Group V atom are independently any alkyl group or hydrogen. The second precursor comprises a Group III atom.

The Group V atom can be any atom selected from Group V of the periodic table of the elements. In a preferred class of embodiments, the Group V atom is N, P, As, Sb, or Bi.

The first precursor can include an $H_3$ substituted Group V atom, an $H_2$alkyl substituted Group V atom, or an Halkyl$_2$ substituted Group V atom. In a preferred class of embodiments, the first precursor comprises a trialkyl substituted Group V atom. The alkyl group can be, e.g., substituted or unsubstituted and/or branched or unbranched (linear). For example, the first precursor can comprise a trimethyl substituted Group V atom, a triethyl substituted Group V atom, or a tri-t-butyl substituted Group V atom. Specific examples of first precursors include, but are not limited to, trimethylphosphine, triethylphosphine, and tri-t-butylphosphine.

The first precursor can be used in combination with essentially any suitable second precursor, whether previously known in the art or described herein. All of the features noted for the second precursor above apply to this embodiment as well. Thus, the Group III atom can be any atom selected from Group III of the periodic table of the elements. In a preferred class of embodiments, the Group III atom is B, Al, Ga, In, or Tl. The second precursor can be a Group III inorganic compound (e.g., a Group III halide, a compound comprising one or more phosphonate, phosphinate, and/or carboxylate moieties bonded to the Group III atom, a Group III metal oxide, or a Group III alkoxy or aryloxy). In other embodiments, the second precursor is a group III organometallic compound (e.g., an alkyl metal or a trialkyl metal, or a Group III atom substituted with three unsaturated groups, e.g., triallyl indium, trivinyl indium, tributadiene indium, trialkylethynyl indium, trialkylethenyl indium, tri-4-phenylethynyl indium, or trialkylphenylethynyl indium, a Group III atom substituted with three cyclic ketone groups, or a Group III atom substituted with three cyclopentadienyl or substituted cyclopentadienyl groups, e.g., an indium tris-Cp compound or an indium tris-(substituted Cp) compound, e.g., tris-cyclopentadienyl indium(III) or tris(n-hexyl cyclopentadienyl) indium(III)).

Essentially all of the features noted above apply to this embodiment as well, as relevant; e.g., for types and composition of nanostructures produced, removal of by-product to increase nanostructure yield, use of first and/or second surfactants, and controlling nanostructure shape by adjusting the ratio of the first and second surfactants, the ratio of the second surfactant and the first or second precursor, and/or the ratio of the first and second precursors. It is worth noting that the molar ratio of the first precursor to the second precursor can be varied; for example, the first precursor can be provided at a molar ratio of at least 1:1, at least 2:1, at least 4:1, at least 8:1, or at least 12:1 with respect to the second precursor.

The first temperature can be, e.g., the nucleation and/or growth temperature. The first temperature is optionally at least 330° C., at least 360° C., at least 380° C., at least 400° C., or at least 420° C., e.g., as required for the particular precursor(s) used or to control nanostructure shape or size.

Nanostructures (e.g., nanocrystals, substantially spherical nanocrystals, nanorods, branched nanostructures, or nanotetrapods) produced by any of the methods herein form another feature of the invention.

Compositions

Compositions related to the methods are another feature of the invention. Thus, one general class of embodiments provides a composition including a first precursor and a second precursor. The first precursor comprises a trisubstituted Group V atom. The trisubstituted Group V atom is other than a) a trialkyl substituted Group V atom comprising an unbranched and unsubstituted alkyl group, b) an $H_3$ substituted Group V atom, c) an $H_2$alkyl substituted Group V atom comprising an unbranched and unsubstituted alkyl group, d) an Halkyl$_2$ substituted Group V atom comprising an unbranched and unsubstituted alkyl group, or e) a tris(trialkylsilyl) substituted Group V atom. In certain embodiments, first precursors of the invention optionally exclude any trialkyl substituted, $H_2$alkyl substituted, or Halkyl$_2$ substituted Group V atom. The second precursor comprises a Group III atom.

The Group V atom can be any atom selected from Group V of the periodic table of the elements. In a preferred class of embodiments, the Group V atom is N, P, As, Sb, or Bi.

The three substituents on the Group V atom in the first precursor can be identical or distinct. The three substituents can be independently any organic group or hydrogen, for example. In one class of embodiments, the first precursor is a Group V organometallic compound.

In one aspect, the first precursor comprises a Group V atom substituted with three unsaturated groups (e.g., any group including at least one double or triple bond or ring, including, but not limited to, alkenyl, alkynyl, acyl, and aryl groups). For example, the first precursor can be triallylphosphine, trivinylphosphine, tributadienylphosphine, trialkylethynylphosphine, trialkylethenylphosphine, tri(4-phenylethynyl)phosphine, or trialkylphenylethynylphosphine. As another example, the first precursor can include a Group V atom substituted with three furyl or furfuryl groups; e.g., the first precursor can be tri-2-furylphosphine or tri-2-furfurylphosphine.

In one class of embodiments, the first precursor comprises a triacyl substituted Group V atom. The acyl group can be, e.g., unsubstituted or substituted. For example, the first precursor can be a triacylphosphine or a triacylarsine, e.g., tribenzoylphosphine, trialkylbenzoylphosphine, trihexylbenzoylphosphine, trialkoylphosphine, or trihexoylphosphine. The substituent optionally comprises an electron donating group or an electron withdrawing group.

In a related class of embodiments, the first precursor comprises a triaryl substituted Group V atom. The aryl group can be, e.g., unsubstituted or substituted. The substituent optionally comprises an electron donating group or an electron withdrawing group. In one class of example embodiments, the first precursor comprises a tribenzyl substituted Group V atom; for example, the first precursor can be tribenzylphosphine or tribenzylarsine.

In another related class of embodiments, the first precursor comprises a Group V atom substituted with three carboxamide groups. Thus, for example, the first precursor can be a tricarboxamide phosphine, e.g., N,N,N,N,N,N-hexaethylphosphine tricarboxamide.

In another class of embodiments, the first precursor comprises a trialkyl substituted Group V atom comprising a substituted and/or branched alkyl group. For example, the first precursor can include a tri-t-butyl substituted Group V atom; e.g., the first precursor can be tri-t-butylphosphine.

In certain embodiments, the first precursor is a Group V inorganic compound. For example, in one class of embodiments, the first precursor comprises a Group V atom substituted with three carboxylate moieties or with three phosphinate moieties. In one embodiment, the Group V atom is P such that the first precursor is a phosphite ester.

The first precursor can be present with essentially any suitable second precursor, whether previously known in the art or described herein (see, e.g., the examples above). The Group III atom can be any atom selected from Group III of the periodic table of the elements. In a preferred class of embodiments, the Group III atom is B, Al, Ga, In, or Tl.

In one class of embodiments, the second precursor is a Group III inorganic compound (e.g., a Group III halide, or a compound in which the Group III atom is directly bonded to at least one oxygen atom or other heteroatom, e.g., nitrogen).

In one class of embodiments, the second precursor is a Group III halide. Thus, in this class of embodiments, the second precursor is $YZ_3$, where Y is a Group III atom (e.g., B, Al, Ga, In, or Tl) and Z is a halogen atom (e.g., F, Cl, Br, I, or At).

In another class of embodiments, the second precursor comprises one or more phosphonate, phosphinate, carboxylate, sulfonate, and/or boronate moieties bonded to the Group III atom. For example, the second precursor can comprise a bi- or tri-substituted Group III atom (e.g., a tricarboxylate, bi- or tri-phosphonate, or triphosphinate substituted Group III atom). Thus, in one class of embodiments, the second precursor is $Y(alkylcarboxylate)_3$, $Y(arylcarboxylate)_3$, $Y(alkylphosphonate)_3$, $Y(arylphosphonate)_3$, $Y(alkylphosphonate)_2$, $Y(arylphosphonate)_2$, $Y(bialkylphosphinate)_3$, or $Y(biarylphosphinate)_3$, where Y is B, Al, Ga, In, or Tl. The alkyl or aryl group can be, e.g., substituted or unsubstituted. For example, the second precursor can be an indium phosphonate or indium carboxylate (e.g., indium triacetate or indium tristearate).

In yet another class of embodiments, the second precursor is a Group III metal oxide. For example, the second precursor can be indium oxide or gallium oxide. As another example, the second precursor can be a Group III alkoxy or Group III aryloxy (e.g., a Group III phenoxy, e.g., indium phenoxy).

In one class of embodiments, instead of being a Group III inorganic compound, the second precursor is a Group III organometallic compound. In some embodiments, the second precursor comprises a tri-substituted Group III atom in which the three substituents are independently any organic group or hydrogen. For example, the second precursor can be an alkyl metal or a trialkyl metal, e.g., trimethyl indium or triethyl indium. In one aspect, the second precursor comprises a Group III atom substituted with three unsaturated groups (e.g., any group including at least one double or triple bond or ring, including, but not limited to, alkenyl, alkynyl, acyl, and aryl groups). For example, the second precursor can be triallyl indium, trivinyl indium, tributadiene indium, trialkylethynyl indium, trialkylethenyl indium, tri-4-phenylethynyl indium, or trialkylphenylethynyl indium. In other embodiments, the second precursor comprises a Group III atom substituted with three cyclic ketone groups; for example, the second precursor can be tris-alpha-cyclohexanone indium (III). In yet other embodiments, the second precursor comprises a Group III atom substituted with three cyclopentadienyl or substituted cyclopentadienyl groups. For example, the second precursor can be an indium tris-Cp compound or an indium tris-(substituted Cp) compound, e.g., tris-cyclopentadienyl indium (III) or tris(n-hexyl cyclopentadienyl) indium(III).

In one class of embodiments, the first precursor comprises a trisubstituted Group V atom where the substituents are dienes, while the second precursor includes a trisubstituted Group III atom where the substituents are dienophiles. In a related class of embodiments, the first precursor comprises a trisubstituted Group V atom where the substituents are dienophiles while the second precursor includes a trisubstituted Group III atom where the substituents are dienes.

The composition optionally also includes at least one surfactant, e.g., a first surfactant, a second surfactant, or a mixture of first and second surfactants. Suitable first surfactants include, but are not limited to, tri-n-alkyl phosphines (e.g., TOP and tri-n-butyl phosphine (TBP)), tri-n-alkyl phosphine oxides (e.g., TOPO), alkyl amines (e.g., monoalkyl amines and bialkyl amines, or trialkyl amines such as trioctylamine), and alkyl- and/or aryl-thiols. In one class of embodiments, the first surfactant is a C12-C30 tri-n-alkyl phosphine, e.g., tri-n-dodecyl phosphine or tri-n-hexadecyl phosphine. As noted above, suitable first surfactants also include unsaturated Group V derivatives; the first surfactant can comprise a Group V atom substituted with three unsaturated groups (e.g., alkenyl or alkynyl groups). Examples include trisalkylphenylethynylphosphines, e.g., tri(ethynylbenzene-hexyl)phosphine, tris(ethynylbenzene-pentyl)phosphine, and the other unsaturated phosphines noted herein. Suitable second surfactants include, but are not limited to, alkyl amines (e.g., monoalkyl amines and bialkyl amines; typically, the first surfactant is not also an alkyl amine) and phosphonic acids (e.g., a C2-30 alkylphosphonic acid), phosphinic acids (e.g., a C2-30 bialkylphosphinic acid), carboxylic acids (e.g., a C2-30 alkylcarboxylic acid), boronic acids, and sulfonic acids, as well as deprotonated forms or condensates thereof.

Similarly, the composition optionally includes a non-coordinating solvent. Preferred solvents include those with a boiling point greater than 100° C. Suitable non-coordinating solvents include long chain alkanes or alkenes, alkane substituted aryl derivatives, and the like (including, for example, hexadecane, octadecane, octadecene, phenyldodecane, phenyltetradecane, and phenylhexadecane). Thus, in one class of embodiments, the non-coordinating solvent comprises an alkane or an alkene. The non-coordinating solvent can be, e.g., hexadecane, octadecane, octadecene, phenyldodecane, phenyltetradecane, or phenylhexadecane. The composition optionally also includes a first and/or second surfactant, e.g., such as those described herein, e.g., a carboxylic acid second surfactant. In one example embodiment, the non-coordinating solvent is phenylhexadecane and the carboxylic acid is stearic acid. Alternatively or in addition, the composition can include a sacrificial oxide acceptor, e.g., a pi-acid such as triphenylphosphine or a substituted triphenylphosphine.

The composition is optionally maintained at a preselected temperature, for example, to facilitate nanostructure nucleation, growth, annealing, or the like. Thus, in one class of embodiments, the temperature of the compositions is at least 250° C., at least 275° C., at least 300° C., at least 320° C., at least 340° C., at least 360° C., at least 380° C., at least 400° C., or at least 420° C.

The composition optionally includes one or more nuclei and/or nanostructures produced by reacting the precursors. Thus, in one class of embodiments, the composition includes one or more nanostructures comprising the Group III atom and the Group V atom.

Essentially all of the features noted above, e.g., for type and composition of nanostructures produced, inclusion of a third precursor, and/or the like, apply to this embodiment as well, as relevant.

A related general class of embodiments provides a composition that includes a first precursor and a second precursor, where the temperature of the composition is at least 300° C. (e.g., at least 330° C., at least 360° C., at least 380° C., at least 400° C., or at least 420° C.). The first precursor comprises a trisubstituted Group V atom, where the three substituents on the Group V atom are independently any alkyl group or hydrogen. The second precursor comprises a Group III atom.

The Group V atom can be any atom selected from Group V of the periodic table of the elements. In a preferred class of embodiments, the Group V atom is N, P, As, Sb, or Bi.

The first precursor can include an $H_3$ substituted Group V atom, an $H_2$alkyl substituted Group V atom, or an Halkyl$_2$ substituted Group V atom. In a preferred class of embodiments, the first precursor comprises a trialkyl substituted Group V atom. The alkyl group can be, e.g., substituted or unsubstituted and/or branched or unbranched (linear). For example, the first precursor can comprise a trimethyl substituted Group V atom, a triethyl substituted Group V atom, or a tri-t-butyl substituted Group V atom. Specific examples of first precursors include, but are not limited to, trimethylphosphine, triethylphosphine, and tri-t-butylphosphine.

The first precursor can be used in combination with essentially any suitable second precursor, whether previously known in the art or described herein. All of the features noted for the second precursor above apply to this embodiment as well. Thus, the Group III atom can be any atom selected from Group III of the periodic table of the elements. In a preferred class of embodiments, the Group III atom is B, Al, Ga, In, or Tl. The second precursor can be a Group III inorganic compound (e.g., a Group III halide, a compound comprising one or more phosphonate, phosphinate, and/or carboxylate moieties bonded to the Group III atom, a Group III metal oxide, or a Group III alkoxy or aryloxy). In other embodiments, the second precursor is a group III organometallic compound (e.g., an alkyl metal or a trialkyl metal, a Group III atom substituted with three unsaturated groups (e.g., triallyl indium, trivinyl indium, tributadiene indium, trialkylethynyl indium, trialkylethenyl indium, tri-4-phenylethynyl indium, or trialkylphenylethynyl indium, a Group III atom substituted with three cyclic ketone groups, or a Group III atom substituted with three cyclopentadienyl or substituted cyclopentadienyl groups, e.g., an indium tris-Cp compound or an indium tris-(substituted Cp) compound, e.g., tris-cyclopentadienyl indium(III) or tris(n-hexyl cyclopentadienyl) indium(III)).

The composition optionally includes one or more nuclei and/or nanostructures produced by reacting the precursors. Thus, in one class of embodiments, the composition includes one or more nanostructures comprising the Group III atom and the Group V atom.

Essentially all of the features noted above apply to this embodiment as well, as relevant; e.g., for types and composition of nanostructures produced and inclusion of surfactants. It is worth noting that, in one class of embodiments, the first surfactant is a tri-n-alkyl phosphine, for example, TOP, TBP, or a C12-C30 tri-n-alkyl phosphine (e.g., tri-n-dodecyl phosphine or tri-n-hexadecyl phosphine). It is also worth noting that the molar ratio of the first precursor to the second precursor can be varied; for example, the first precursor can be present at a molar ratio of at least 1:1, at least 2:1, at least 4:1, at least 8:1, or at least 12:1 with respect to the second precursor.

Group III Precursors

In one aspect, the invention relates to novel Group III precursors (e.g., Group III oxides, alkoxys, and aryloxys, and precursors including a Group III atom substituted with three unsaturated groups). Methods using such precursors in production of Group III-V semiconductor nanostructures are provided. Related methods for synthesizing and using certain Group III precursors are described. Compositions related to the methods are also provided.

Methods

Thus, one general class of embodiments provides methods for production of Group III-V semiconductor nanostructures. In the methods, a first precursor and a second precursor are provided, and the first and second precursors are reacted to produce the nanostructures. The first precursor comprises a Group V atom. The second precursor is either a Group III inorganic compound other than a Group III halide (e.g., $InCl_3$) or a Group III acetate (e.g., $InAc_3$), or a Group III organometallic compound other than a trialkyl substituted Group III atom comprising an unbranched and unsubstituted alkyl group. In certain embodiments, second precursors of the invention optionally exclude any trialkyl substituted Group III atom.

The Group III atom can be any atom selected from Group III of the periodic table of the elements. In a preferred class of embodiments, the second precursor comprises B, Al, Ga, In, or Tl as the Group III atom.

In one aspect, the second precursor is a Group III inorganic compound (e.g., a compound in which the Group III atom is directly bonded to at least one oxygen atom or other heteroatom, e.g., nitrogen).

In one class of embodiments, the second precursor is a Group III inorganic compound comprising one or more phosphonate, phosphinate, carboxylate, sulfonate, and/or boronate moieties bonded to a Group III atom. For example, the second precursor can comprise a bi- or tri-substituted Group III atom (e.g., a tricarboxylate, bi- or tri-phosphonate, or triphosphinate substituted Group III atom). Thus, in one class of embodiments, the Group III inorganic compound is Y(alkylcarboxylate)$_3$, Y(arylcarboxylate)$_3$, Y(alkylphosphonate)$_3$, Y(arylphosphonate)$_3$, Y(alkylphosphonate)$_2$, Y(arylphosphonate)$_2$, Y(bialkylphosphinate)$_3$, or Y(biarylphosphinate)$_3$, where Y is B, Al, Ga, In, or Tl. The alkyl or aryl group can be, e.g., substituted or unsubstituted. For example, the second precursor can be an indium phosphonate or indium carboxylate other than indium triacetate (e.g., indium tristearate).

In another class of embodiments, the Group III inorganic compound is a Group III metal oxide. For example, the Group III inorganic compound can be indium oxide or gallium oxide. As another example, the Group III inorganic compound can be a Group III alkoxy or Group III aryloxy (e.g., a Group III phenoxy, e.g., indium phenoxy).

In another aspect, instead of being a Group III inorganic compound, the second precursor is a Group III organometallic compound. In one aspect, the second precursor comprises a Group III atom substituted with three unsaturated groups (e.g., any group including at least one double or triple bond or ring, including, but not limited to, alkenyl, alkynyl, acyl, and aryl groups). For example, the second precursor can be triallyl indium, trivinyl indium, tributadiene indium, trialkylethynyl indium, trialkylethenyl indium, tri-4-phenylethynyl indium, or trialkylphenylethynyl indium. In one class of embodiments, the second precursor comprises a Group III atom substituted with three cyclic ketone groups; for example, the second precursor can be tris-alpha-cyclohexanone indium (III). In other embodiments, the second precursor comprises a Group III atom substituted with three cyclopentadienyl or substituted cyclopentadienyl groups. For example, the second precursor can be an indium tris-Cp compound or an indium tris-(substituted Cp) compound, for example, tris-cyclopentadienyl indium(III) or tris(n-hexyl cyclopentadienyl) indium (III).

In another class of embodiments in which the second precursor is a Group III organometallic compound, the second precursor comprises a trialkyl substituted Group III atom, e.g., a trialkyl substituted Group III atom comprising a substituted and/or branched alkyl group.

The second precursor can be used in combination with essentially any suitable first precursor, whether previously known in the art or described herein. The Group V atom can be any atom selected from Group V of the periodic table of the elements. In a preferred class of embodiments, the Group V atom is N, P, As, Sb, or Bi.

The first precursor optionally comprises a trisubstituted Group V atom, e.g., where the Group V atom is N, P, As, Sb, or B. The three substituents on the Group V atom in the first precursor can be identical or distinct. In one class of embodiments, the first precursor is a Group V organometallic compound. The three substituents can be independently any organic group or hydrogen, for example.

All of the features noted for the first precursor in the embodiments above apply to this embodiment as well. For example, in one class of embodiments, the first precursor comprises a Group V atom substituted with three unsaturated groups (e.g., the first precursor can be triallylphosphine, trivinylphosphine, tributadienylphosphine, trialkylethynylphosphine, trialkylethenylphosphine, tri(4-phenylethynyl)phosphine, or trialkylphenylethynylphosphine). For example, the first precursor can comprise a triacyl substituted Group V atom. The acyl group can be, e.g., unsubstituted or substituted. For example, the first precursor can be a triacylphosphine or a triacylarsine, e.g., tribenzoylphosphine, trialkylbenzoylphosphine, trihexylbenzoylphosphine, trialkoylphosphine, or trihexoylphosphine. As another example, the first precursor can comprise a Group V atom substituted with three carboxamide groups (e.g., a tricarboxamide phosphine, e.g., N,N,N,N,N,N-hexaethylphosphine tricarboxamide), three furyl groups (e.g., tri-2-furylphosphine), or three furfuryl groups (e.g., tri-2-furfurylphosphine).

In a related class of embodiments, the first precursor comprises a triaryl substituted Group V atom. The aryl group can be, e.g., unsubstituted or substituted. The substituent optionally comprises an electron donating group or an electron withdrawing group. In one class of example embodiments, the first precursor comprises a tribenzyl substituted Group V atom; for example, the first precursor can be tribenzylphosphine or tribenzylarsine.

In another related class of embodiments, the first precursor comprises a trialkyl substituted Group V atom. The alkyl group can be, e.g., substituted or unsubstituted and/or branched or unbranched (linear). For example, the first precursor can include a trimethyl substituted Group V atom, a triethyl substituted Group V atom, or a tri-t-butyl substituted Group V atom; e.g., the first precursor can be trimethylphosphine, triethylphosphine, or tri-t-butylphosphine.

In other embodiments, the first precursor comprises an $H_3$ substituted Group V atom, an $Halkyl_2$ substituted Group V atom, an $Halkyl_2$ substituted Group V atom comprising a substituted and/or branched alkyl group, an $H_2alkyl$ substituted Group V atom, an $H_2alkyl$ substituted Group V atom comprising a substituted and/or branched alkyl group, or a tris(trialkylsilyl) substituted Group V atom (e.g., a tris(trialkylsilyl)arsine or a tris(trialkylsilyl)phosphine, e.g., tris(trimethylsilyl)arsine or tris(trimethylsilyl)phosphine).

In certain embodiments, the first precursor is a Group V inorganic compound. For example, in one class of embodiments, the first precursor comprises a Group V atom substituted with three carboxylate moieties or with three phosphinate moieties. In one embodiment, the Group V atom is P such that the first precursor is a phosphite ester.

In one class of embodiments, the first precursor comprises a trisubstituted Group V atom where the substituents are dienes, while the second precursor includes a trisubstituted Group III atom where the substituents are dienophiles. In a related class of embodiments, the first precursor comprises a trisubstituted Group V atom where the substituents are dienophiles while the second precursor includes a trisubstituted Group III atom where the substituents are dienes.

Essentially all of the features noted above apply to this embodiment as well, as relevant; e.g., for types and composition of nanostructures produced, removal of by-product to increase nanostructure yield, use of first and/or second surfactants, non-coordinating solvents, and/or sacrificial oxide acceptors, pre-formation of a Group III-V complex, temperature, and controlling nanostructure shape by adjusting the ratio of the first and second surfactants, the ratio of the second surfactant and the first or second precursor, and/or the ratio of the first and second precursors.

Another general class of embodiments provides methods of producing a Group III inorganic compound. In the methods, a first reactant and a second reactant are provided and reacted to produce the Group III inorganic compound. The first reactant is a Group III halide, e.g., $YZ_3$, where Y is B, Al, Ga, In, or Tl and Z is F, Cl, Br, I, or At.

In a preferred class of embodiments, the second reactant is an acid, e.g., phosphonic acid, a phosphinic acid, a carboxylic acid (e.g., stearic acid), a sulfonic acid, or a boronic acid. In certain embodiments, the acid is other than acetic acid. The resulting Group III inorganic compound thus, in certain embodiments, comprises one or more phosphonate, phosphinate, and/or carboxylate moieties bonded to the Group III atom. Examples of such compounds include, but are not limited to, $Y(alkylcarboxylate)_3$, $Y(arylcarboxylate)_3$, $Y(alkylphosphonate)_3$, $Y(arylphosphonate)_3$, $Y(alkylphosphonate)_2$, $Y(arylphosphonate)_2$, $Y(bialkylphosphinate)_3$, and $Y(biarylphosphinate)_3$, where Y is B, Al, Ga, In, or Tl. For example, the Group III inorganic compound can be indium phosphonate or indium carboxylate (e.g., indium tristearate). In other embodiments, the second reactant is an alcohol or an alkyl amine.

The second reactant is typically provided at a molar ratio of about 3:1 with respect to the first reactant (e.g., about 2.8-3.2, about 2.9-3.1, or about 2.95-3.05). In other embodiments, the second reactant is provided at a molar ratio of more than 3:1 with respect to the first reactant.

A related general class of embodiments also provides methods of producing a Group III inorganic compound. In the methods, a first reactant and a second reactant are provided and reacted to produce the Group III inorganic compound. The first reactant includes a trialkyl substituted Group III atom (e.g., B, Al, Ga, In, or Tl). The second reactant is an acid, e.g., a phosphonic acid, a phosphinic acid, a carboxylic acid (e.g., stearic acid), a sulfonic acid, or a boronic acid. The resulting Group III inorganic compound thus, in certain embodiments, comprises one or more phosphonate, phosphinate, and/or carboxylate moieties bonded to the Group III atom. Examples of such compounds include, but are not limited to, Y(alkylcarboxylate)$_3$, Y(arylcarboxylate)$_3$, Y(alkylphosphonate)$_3$, Y(arylphosphonate)$_3$, Y(alkylphosphonate)$_2$, Y(arylphosphonate)$_2$, Y(bialkylphosphinate)$_3$, and Y(biarylphosphinate)$_3$, where Y is B, Al, Ga, In, or Tl. For example, the Group III inorganic compound can be indium phosphonate or indium carboxylate (e.g., indium tristearate).

The second reactant is typically provided at a molar ratio of about 3:1 with respect to the first reactant (e.g., about 2.8-3.2, about 2.9-3.1, or about 2.95-3.05). In other embodiments, the second reactant is provided at a molar ratio of more than 3:1 with respect to the first reactant.

As one specific example, reaction of trimethyl indium with three equivalents of stearic acid yields indium tristearate and methane (which is easily removed as a vapor).

Both general classes of methods optionally include using the resulting Group III inorganic compound as a precursor in a nanostructure synthesis reaction. Thus, in one class of embodiments, the methods include providing a first precursor comprising a Group V atom and reacting the Group III inorganic compound and the first precursor to produce Group III-V semiconductor nanostructures. The Group III inorganic compound is optionally substantially isolated from any unreacted first reactant and/or second reactant prior to its reaction with the first precursor.

A group III inorganic compound produced by the methods is a feature of the invention. Similarly, as noted, nanostructures (e.g., nanocrystals, substantially spherical nanocrystals, nanorods, branched nanostructures, or nanotetrapods) produced by any of the methods herein form another feature of the invention.

Use of such Group III inorganic compounds as precursors can be advantageous. For example, use of these precursors can assist in shape control of the resulting nanostructures. These precursors begin with the shape-controlling surfactant already bound to the metal which will comprise the surface of the nanocrystal. As another example, reaction of the Group III inorganic compounds may form less reactive co-products. For example, reaction of a tribenzylphosphine first precursor with a Group III halide second precursor produces a very reactive benzyl halide co-product, whereas reaction of the tribenzylphosphine first precursor with a Group III phosphonate or carboxylate compound can produce a less reactive co-product (e.g., a phosphonic or carboxylic ester, respectively).

Compositions

Compositions related to the methods are another feature of the invention. Thus, one general class of embodiments provides a composition including a first precursor comprising a Group V atom and a second precursor. The second precursor is either a Group III inorganic compound other than a Group III halide (e.g., InCl$_3$) or a Group III acetate (e.g., InAc$_3$), or a Group III organometallic compound other than a trialkyl substituted Group III atom comprising an unbranched and unsubstituted alkyl group. In certain embodiments, second precursors of the invention optionally exclude any trialkyl substituted Group III atom.

The Group III atom can be any atom selected from Group III of the periodic table of the elements. In a preferred class of embodiments, the second precursor comprises B, Al, Ga, In, or Tl as the Group III atom.

In one aspect, the second precursor is a Group III inorganic compound (e.g., a compound in which the Group III atom is directly bonded to at least one oxygen atom or other heteroatom, e.g., nitrogen).

In one class of embodiments, the second precursor is a Group III inorganic compound comprising one or more phosphonate, phosphinate, carboxylate, sulfonate, and/or boronate moieties bonded to a Group III atom. For example, the second precursor can comprise a bi- or tri-substituted Group III atom (e.g., a tricarboxylate, bi- or tri-phosphonate, or triphosphinate substituted Group III atom). Thus, in one class of embodiments, the Group III inorganic compound is Y(alkylcarboxylate)$_3$, Y(arylcarboxylate)$_3$, Y(alkylphosphonate)$_3$, Y(arylphosphonate)$_3$, Y(alkylphosphonate)$_2$, Y(arylphosphonate)$_2$, Y(bialkylphosphinate)$_3$, or Y(biarylphosphinate)$_3$, where Y is B, Al, Ga, In, or Tl. The alkyl or aryl group can be, e.g., substituted or unsubstituted. For example, the second precursor can be an indium phosphonate or indium carboxylate other than indium triacetate (e.g., indium tristearate).

In another class of embodiments, the Group III inorganic compound is a Group III metal oxide. For example, the Group III inorganic compound can be indium oxide or gallium oxide. As another example, the Group III inorganic compound can be a Group III alkoxy or Group III aryloxy (e.g., a Group III phenoxy, e.g., indium phenoxy).

In another aspect, instead of being a Group III inorganic compound, the second precursor is a Group III organometallic compound. For example, in one aspect, the second precursor comprises a Group III atom substituted with three unsaturated groups (e.g., any group including at least one double or triple bond or ring, including, but not limited to, alkenyl, alkynyl, acyl, and aryl groups). For example, the second precursor can be triallyl indium, trivinyl indium, tributadiene indium, trialkylethynyl indium, trialkylethenyl indium, tri-4-phenylethynyl indium, or trialkylphenylethynyl indium. For example, in one class of embodiments, the second precursor comprises a Group III atom substituted with three cyclic ketone groups; for example, the second precursor can be tris-alpha-cyclohexanone indium (III). In other embodiments, the second precursor comprises a Group III atom substituted with three cyclopentadienyl or substituted cyclopentadienyl groups. For example, the second precursor can be an indium tris-Cp compound or an indium tris-(substituted Cp) compound, for example, tris-cyclopentadienyl indium (III) or tris(n-hexyl cyclopentadienyl) indium(III).

In another class of embodiments in which the second precursor is a Group III organometallic compound, the second precursor comprises a trialkyl substituted Group III atom, e.g., a trialkyl substituted Group III atom comprising a substituted and/or branched alkyl group.

The second precursor can be present with essentially any suitable first precursor, whether previously known in the art or described herein. The Group V atom can be any atom selected from Group V of the periodic table of the elements. In a preferred class of embodiments, the Group V atom is N, P, As, Sb, or Bi.

The first precursor optionally comprises a trisubstituted Group V atom, e.g., where the Group V atom is N, P, As, Sb, or B. The three substituents on the Group V atom in the first precursor can be identical or distinct. In one class of embodiments, the first precursor is a Group V organometallic compound. The three substituents can be independently any organic group or hydrogen, for example.

All of the features noted for the first precursor in the embodiments above apply to this embodiment as well. For example, the first precursor can include a Group V atom substituted with three unsaturated groups (e.g., the first precursor can be triallylphosphine, trivinylphosphine, tributadienylphosphine, trialkylethynylphosphine, trialkylethenylphosphine, tri(4-phenylethynyl)phosphine, or trialkylphenylethynylphosphine). For example, the first precursor can comprise a triacyl substituted Group V atom. The acyl group can be, e.g., unsubstituted or substituted. For example, the first precursor can be a triacylphosphine or a triacylarsine, e.g., tribenzoylphosphine, trialkylbenzoylphosphine, trihexylbenzoylphosphine, trialkoylphosphine, or trihexoylphosphine. As another example, the first precursor can comprise a Group V atom substituted with three carboxamide groups (e.g., a tricarboxamide phosphine, e.g., N,N,N,N,N,N-hexaethylphosphine tricarboxamide), three furyl groups (e.g., tri-2-furylphosphine), or three furfuryl groups (e.g., tri-2-furfurylphosphine).

In a related class of embodiments, the first precursor comprises a triaryl substituted Group V atom. The aryl group can be, e.g., unsubstituted or substituted. The substituent optionally comprises an electron donating group or an electron withdrawing group. In one class of example embodiments, the first precursor comprises a tribenzyl substituted Group V atom; for example, the first precursor can be tribenzylphosphine or tribenzylarsine.

In another related class of embodiments, the first precursor comprises a trialkyl substituted Group V atom. The alkyl group can be, e.g., substituted or unsubstituted and/or branched or unbranched (linear). For example, the first precursor can include a trimethyl substituted Group V atom, a triethyl substituted Group V atom, or a tri-t-butyl substituted Group V atom; e.g., the first precursor can be trimethylphosphine, triethylphosphine, or tri-t-butylphosphine.

In other embodiments, the first precursor comprises an $H_3$ substituted Group V atom, an $Halkyl_2$ substituted Group V atom, an $Halkyl_2$ substituted Group V atom comprising a substituted and/or branched alkyl group, an $H_2alkyl$ substituted Group V atom, an $H_2alkyl$ substituted Group V atom comprising a substituted and/or branched alkyl group, or a tris(trialkylsilyl) substituted Group V atom (e.g., a tris(trialkylsilyl)arsine or a tris(trialkylsilyl)phosphine, e.g., tris(t-rimethylsilyl)arsine or tris(trimethylsilyl)phosphine).

In certain embodiments, the first precursor is a Group V inorganic compound. For example, in one class of embodiments, the first precursor comprises a Group V atom substituted with three carboxylate moieties or with three phosphinate moieties. In one embodiment, the Group V atom is P such that the first precursor is a phosphite ester.

In one class of embodiments, the first precursor comprises a trisubstituted Group V atom where the substituents are dienes, while the second precursor includes a trisubstituted Group III atom where the substituents are dienophiles. In a related class of embodiments, the first precursor comprises a trisubstituted Group V atom where the substituents are dienophiles while the second precursor includes a trisubstituted Group III atom where the substituents are dienes.

The composition optionally also includes at least one surfactant, e.g., a first surfactant, a second surfactant, or a mixture of first and second surfactants. Suitable first surfactants include, but are not limited to, tri-n-alkyl phosphines (e.g., TOP and tri-n-butyl phosphine (TBP)), tri-n-alkyl phosphine oxides (e.g., TOPO), alkyl amines (e.g., monoalkyl amines and bialkyl amines, or trialkyl amines such as trioctylamine), and alkyl- and/or aryl-thiols. In one class of embodiments, the first surfactant is a C12-C30 tri-n-alkyl phosphine, e.g., tri-n-dodecyl phosphine or tri-n-hexadecyl phosphine. Suitable first surfactants also include unsaturated Group V derivatives; the first surfactant can comprise a Group V atom substituted with three unsaturated groups (e.g., alkenyl or alkynyl groups). Examples include trisalkylphenylethynylphosphines, e.g., tri(ethynylbenzene-hexyl)phosphine, tris(ethynylbenzene-pentyl)phosphine, and the other unsaturated phosphines noted herein. Suitable second surfactants include, but are not limited to, alkyl amines (e.g., monoalkyl amines and bialkyl amines; typically, the first surfactant is not also an alkyl amine) and phosphonic acids (e.g., a $C_{2-30}$ alkylphosphonic acid), phosphinic acids (e.g., a $C_{2-30}$ bialkylphosphinic acid), carboxylic acids (e.g., a $C_{2-30}$ alkylcarboxylic acid), boronic acids, and sulfonic acids, as well as deprotonated forms or condensates thereof.

Similarly, the composition optionally includes a non-coordinating solvent. Preferred solvents include those with a boiling point greater than 100° C. Suitable non-coordinating solvents include long chain alkanes or alkenes, alkane substituted aryl derivatives, and the like (including, for example, hexadecane, octadecane, octadecene, phenyldodecane, phenyltetradecane, and phenylhexadecane). Thus, in one class of embodiments, the non-coordinating solvent comprises an alkane or an alkene. The non-coordinating solvent can be, e.g., hexadecane, octadecane, octadecene, phenyldodecane, phenyltetradecane, or phenylhexadecane. The composition optionally also includes a first and/or second surfactant, e.g., such as those described herein, e.g., a carboxylic acid second surfactant. In one example embodiment, the non-coordinating solvent is phenylhexadecane and the carboxylic acid is stearic acid. Alternatively or in addition, the composition optionally includes a sacrificial oxide acceptor, e.g., a pi-acid such as triphenylphosphine.

The composition is optionally maintained at a preselected temperature, for example, to facilitate nanostructure nucleation, growth, annealing, or the like. Thus, in one class of embodiments, the temperature of the compositions is at least 250° C., at least 275° C., at least 300° C., at least 320° C., at least 340° C., at least 360° C., at least 380° C., at least 400° C., or at least 420° C.

The composition optionally includes one or more nuclei and/or nanostructures produced by reacting the precursors. Thus, in one class of embodiments, the composition includes one or more nanostructures comprising the Group V atom and a Group III atom from the Group III inorganic or organometallic compound.

Essentially all of the features noted above, e.g., for type and composition of nanostructures, inclusion of a third precursor, and/or the like, apply to this embodiment as well, as relevant.

Another general class of embodiments provides a composition that can be used, for example, for producing a Group III inorganic compound. The composition includes a first reactant and a second reactant. In one class of embodiments, the first reactant is a Group III halide, e.g., $YZ_3$, where Y is B, Al, Ga, In, or Tl and Z is F, Cl, Br, I, or At. In a related class of embodiments, the first reactant comprises a trialkyl substituted Group III atom (e.g., the first reactant can be a trialkyl indium, e.g., trimethyl indium). The second reactant is a phosphonic acid, a phosphinic acid, a carboxylic acid (e.g., stearic acid), a sulfonic acid, a boronic acid, or an alcohol. In certain embodiments, the acid is optionally an acid other than acetic acid.

The second reactant is typically present at a molar ratio of about 3:1 with respect to the first reactant (e.g., about 2.8-3.2, about 2.9-3.1, or about 2.95-3.05). In other embodiments, the second reactant is provided at a molar ratio of more than 3:1 with respect to the first reactant.

The composition optionally includes a Group III inorganic compound produced by a reaction of the first and second reactants. Thus, in one class of embodiments, the resulting Group III inorganic compound comprises one or more phosphonate, phosphinate, and/or carboxylate moieties bonded to the Group III atom. Examples of such compounds include, but are not limited to, Y(alkylcarboxylate)$_3$, Y(arylcarboxylate)$_3$, Y(alkylphosphonate)$_3$, Y(arylphosphonate)$_3$, Y(alkylphosphonate)$_2$, Y(arylphosphonate)$_2$, Y(bialkylphosphinate)$_3$, and Y(biarylphosphinate)$_3$. For example, the Group III inorganic compound can be indium phosphonate or indium carboxylate (e.g., indium tristearate).

Essentially all of the features noted above apply to this embodiment as well, as relevant.

Nanostructure Growth at High Temperature

As noted previously, nucleation and/or growth at high temperatures may be necessary for use of certain precursors and/or desirable for producing certain nanostructure shapes. Thus, one general class of embodiments provides high-temperature methods for production of Group III-V semiconductor nanostructures. In the methods, one or more surfactants and/or non-coordinating solvents, a first precursor comprising a Group V atom, and a second precursor comprising a Group III atom are provided. The one or more surfactants and/or non-coordinating solvents are heated to a first temperature. The first and second precursors and the one or more heated surfactants and/or non-coordinating solvents are contacted, and the first and second precursors react to form nuclei capable of nucleating nanostructure growth. The first and second precursors, the one or more surfactants and/or non-coordinating solvents, and the nuclei are maintained at a second temperature which permits growth of the nuclei to produce the nanostructures; the first and second precursors react to grow the nanostructures from the nuclei. The first temperature is at least 360° C. and/or the second temperature is at least 300° C.

For example, the first temperature can be at least 380° C., at least 400° C., or at least 420° C. Similarly, the second temperature can be at least 330° C., at least 360° C., at least 380° C., at least 400° C., or at least 420° C. The first temperature can be greater than (or less than) the second temperature, e.g., by about 40-80° C., about 20-40° C., about 10-20° C., about 5-10° C., or about 0-5° C., or the first and second temperatures can be equal.

As noted, suitable surfactants are typically liquid at the temperature at which the nanostructures are nucleated and/or grown. Thus, in a preferred class of embodiments, each of the one or more surfactants has a boiling point that is greater than the first and second temperatures. Similar considerations apply for any non-coordinating solvent(s).

Essentially all of the features noted above apply to this embodiment as well, as relevant; e.g., for types and composition of nanostructures produced, removal of by-product to increase nanostructure yield, Group III and V atoms, first and second precursors, use of first and/or second surfactants, and controlling nanostructure shape by adjusting the ratio of the first and second surfactants, the ratio of the second surfactant and the first or second precursor, and/or the ratio of the first and second precursors. It is worth noting that, in one class of embodiments, the first surfactant is a tri-n-alkyl phosphine or a tri-n-alkyl phosphine oxide, for example, a C12-C30 tri-n-alkyl phosphine (e.g., tri-n-dodecyl phosphine or tri-n-hexadecyl phosphine).

Nanostructures (e.g., nanocrystals, substantially spherical nanocrystals, nanorods, branched nanostructures, or nanotetrapods) produced by any of the methods herein form another feature of the invention.

Compositions related to the methods are also provided. Thus, one general class of embodiments provides a composition comprising one or more surfactants, a first precursor comprising a Group V atom, and a second precursor comprising a Group III atom. The temperature of the composition is at least 360° C. (e.g., at least 380° C., at least 400° C., or at least 420° C.). Each of the one or more surfactants preferably has a boiling point that is greater than the temperature of the composition.

The composition optionally includes one or more nuclei and/or nanostructures produced by reacting the precursors. Thus, in one class of embodiments, the composition includes one or more nanostructures comprising the Group III atom and the Group V atom.

Essentially all of the features noted above apply to this embodiment as well, as relevant; e.g., for types and composition of nanostructures produced, Group III and V atoms, first and second precursors, and inclusion of first and/or second surfactants. It is worth noting that, in one class of embodiments, the first surfactant is a tri-n-alkyl phosphine or a tri-n-alkyl phosphine oxide, for example, a C12-C30 tri-n-alkyl phosphine (e.g., tri-n-dodecyl phosphine or tri-n-hexadecyl phosphine).

Co-Products

Stable Co-Products

Reacting precursors to produce nanostructures typically produces both the desired nanostructures and at least one co-product. Selecting precursors such that the co-product is relatively stable can be advantageous (e.g., can assist in preventing undesirable side reactions). In one aspect, the invention provides methods of synthesizing nanostructures that result in production of the nanostructures and a relatively stable co-product.

Thus, one general class of embodiments provides methods for production of Group III-V semiconductor nanostructures. In the methods, a first precursor comprising a Group V atom and a second precursor comprising a Group III atom are provided and reacted to produce the nanostructures and at least one co-product. In one class of embodiments, the co-product is an ester, a ketone, or an ether.

Reaction of a variety of combinations of first and second precursors results in formation of an ether, ketone, or ester. For example, when the first precursor comprises a trialkyl substituted Group V atom and the second precursor comprises a tricarboxylate substituted Group III atom, the co-product can be an ester. As another example, the first precursor can comprise a triacyl substituted Group V atom, the second precursor a Group III atom substituted with three cyclic ketone groups (e.g., tris-alpha-cyclohexanone indium (III)), and the co-product an ester (see, e.g., FIG. 2 Panel A). As yet another example, the first precursor can comprise a triacyl substituted Group V atom, the second precursor a Group III alkoxy or aryloxy, and the co-product an ester (see, e.g., FIG. 2 Panel E). As yet another example, the first precursor can comprise a triacyl substituted Group V atom, the second precursor a tris-Cp or tris-(substituted Cp) Group III atom (e.g., an indium tris-Cp or tris-(substituted Cp) compound, e.g., tris-cyclopentadienyl indium(III) or tris(n-hexyl cyclopentadienyl) indium(III)), and the co-product a ketone (see, e.g., FIG. 2 Panel F). As yet another example, the first precursor can comprise triphenylphosphine or a tri-alkylphosphine, the second precursor tri-alkoxyindium, and the co-product an ether. See also Examples 7 and 8 herein.

The methods optionally include substantially purifying the nanostructures away from the co-product (e.g., prior to their use or incorporation into an optoelectronic device, a nanocomposite, or the like). For example, an ester, ketone, or ether co-product can be evaporated using a vacuum and/or heat.

Essentially all of the features noted above apply to this embodiment as well, as relevant; e.g., for types and composition of nanostructures produced, first and second precursors, and/or the like.

Nanostructures (e.g., nanocrystals, substantially spherical nanocrystals, nanorods, branched nanostructures, or nanotetrapods) produced by the methods form another feature of the invention.

Another general class of embodiments provides compositions related to the methods. The composition comprises a first precursor comprising a Group V atom, a second precursor comprising a Group III atom, a nanostructure comprising the Group III atom and the Group V atom, and a co-product. In one class of embodiments, the co-product is an ester, a ketone, or an ether. The nanostructure and the co-product were produced by reaction of the precursors.

Essentially all of the features noted above apply to this embodiment as well, as relevant; e.g., for types and composition of nanostructures produced, first and second precursors, co-products, and/or the like.

By-Product Removal

In one aspect, the invention provides methods for production of nanostructures that can, e.g., increase yield of nanostructures from nanostructure synthesis reactions through removal of a vapor by-product. In the methods, one or more precursors are provided and reacted at a reaction temperature (e.g., a nanostructure growth temperature) to produce the nanostructures and at least one by-product. The by-product has a boiling point or sublimation temperature that is less than the reaction temperature. At least a portion of the by-product is removed as a vapor. Removal of the by-product pushes the reaction equilibrium toward making more nanostructures.

The nanostructures can be of essentially any type and/or composition. For example, the nanostructures can be semiconductor nanostructures, e.g., Group II-VI semiconductor nanostructures, Group III-V semiconductor nanostructures, Group IV semiconductor nanostructures, metal nanostructures, or metal oxide nanostructures.

In one class of embodiments, the one or more precursors comprise a first precursor comprising a group VI atom and a second precursor comprising a group II atom. The resulting nanostructures can comprise essentially any Group II-group VI semiconductor, including, but not limited to, ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, and BaTe.

In other embodiments, the one or more precursors comprise a group IV atom or a metal atom. The resulting nanostructures can comprise essentially any Group IV semiconductor, metal, or metal oxide, including, but not limited to, Ge, Si, PbS, PbSe, PbTe, Au, Ag, Co, Fe, Ni, Cu, Zn, Pd, Pt, $BaTiO_3$, $SrTiO_3$, $CaTiO_3$, $KNbO_3$, $PbTiO_3$, $LiTiO_3$, $LiTaO_3$, or $LiNbO_3$, or an alloy or mixture thereof.

In one class of embodiments, the one or more precursors include a first precursor comprising a group V atom and a second precursor comprising a group III atom. The resulting nanostructures can comprise essentially any Group III-V semiconductor, including, but not limited to, InN, InP, InAs, InSb, GaN, GaP, GaAs, GaSb, AlN, AlP, AlAs, and AlSb.

A number of precursors and reaction temperatures can be selected such that the by-product formed has a boiling point or sublimation temperature less than the reaction temperature. For example, in one class of embodiments, at least two precursors are reacted to form Group III-V semiconductor nanostructures. The first precursor comprises a trialkyl or triaryl substituted Group V atom, the second precursor is a Group III halide, and the by-product is thus an alkyl or aryl halide. Preferably, the Group V atom is N, P, As, Sb, or Bi, and the Group III halide comprises B, Al, Ga, In, or Tl and F, Cl, Br, I, or At. Example by-products include, but are not limited to, chlorooctane, bromooctane, benzylbromide, benzyliodide, or benzylchloride.

FIG. 3 Panels A and B illustrate an example reaction in which the first precursor is TOP, the second precursor is $InCl_3$, and the by-product is chlorooctane. Removal of chlorooctane, which has a boiling point of 183° C., as a vapor results in formation of more InP nanostructures (e.g., nanocrystals).

Essentially all of the features noted above apply to this embodiment as well, as relevant; e.g., for types and composition of nanostructures produced, inclusion of surfactant(s), precursors, and the like.

Nanostructures (e.g., nanocrystals, substantially spherical nanocrystals, nanorods, branched nanostructures, or nanotetrapods) produced by the methods form another feature of the invention.

Another general class of embodiments provides compositions related to the methods. The composition comprises one or more precursors, nanostructures, and at least one by-product. The by-product has a boiling point or sublimation temperature that is less than a temperature of the composition (e.g., a nanostructure growth temperature). A portion of the by-product will therefore be a vapor.

Essentially all of the features noted above apply to this embodiment as well, as relevant; e.g., for types and composition of nanostructures produced, inclusion of surfactant(s), precursors, by-products, and the like.

Surfactants

As noted above, one or more surfactants are typically used in a nanostructure synthesis reaction, to assist in controlling shape and/or size of the resulting nanostructures, to maintain solubility and prevent aggregation of the nanostructures, and/or the like. A number of suitable surfactants are described herein and known in the art and can be used singly or in various combinations. Examples include, but are not limited to, tri-n-alkyl phosphines (e.g., TOP and tri-n-butyl phosphine (TBP)), tri-n-alkyl phosphine oxides (e.g., TOPO), alkyl amines (e.g., monoalkyl amines and bialkyl amines, or trialkyl amines such as trioctylamine), alkyl-thiols, aryl-thiols, unsaturated Group V derivatives (e.g., trisalkylphenylethynylphosphines, e.g., tri(ethynylbenzene-hexyl)phosphine and tris(ethynylbenzene-pentyl)phosphine), phosphonic acids (e.g., a $C_{2-30}$ alkylphosphonic acid), phosphinic acids (e.g., a $C_{2-30}$ bialkylphosphinic acid), carboxylic acids (e.g., a C2-30 alkylcarboxylic acid), boronic acids, and sulfonic acids. As noted, in certain embodiments, the same substance can serve as both a precursor and a surfactant.

A suitable surfactant (or combination of surfactants) for use with a given set of precursors can be determined by experimentation as is known in the art. Factors affecting choice of surfactant(s) can include, for example, reaction temperature, choice of precursors, and desired size and shape of the nanostructures to be produced. For example, if the nanostructures are to be nucleated and/or grown at high temperature, the surfactant(s) must be stable at that temperature. As another example, the relative nucleophilicity of the precursor(s) and surfactant(s) can affect the choice of surfactant; for example, tri-n-alkyl phosphines are typically not used as surfactants in combination with unsaturated phosphine second (Group III) precursors. As a specific example, for reaction of a $Cp_3In$ first precursor with a tribenzoylphosphine second precursor to form InP nanostructures, tri-n-alkyl phosphine surfactants can knock the tribenzoylphosphine off of the $Cp_3In$ coordination site, favoring the formation of Indium metal instead of InP, and are thus less desirable for use as surfactants with these precursors. As another example, if the surfactant is capable of reacting with the first precursor, it is typically used in combination with a second precursor that reacts at a lower temperature. As just one specific example, a trialkoyl phosphine can be used as the Group III precursor and tri(ethynylbenzene-hexyl)phosphine as the first surfactant, since the trialkoyl phosphine will react at a lower temperature than the tri(ethynylbenzene-hexyl)phosphine will.

Methods and compositions including surfactants of the invention (e.g., tri-unsaturated Group V derivatives) form a feature of the invention. Thus, one general class of embodiments provides methods for production of nanostructures. In the methods, a surfactant comprising a Group V atom substituted with three unsaturated groups and one or more precursors are provided. The one or more precursors are reacted in the presence of the surfactant to produce the nanostructures. In one class of embodiments, the nanostructures are Group III-V semiconductor nanostructures; in this class of embodiments, the one or more precursors can, e.g., include a first precursor comprising a Group V atom and a second precursor comprising a Group III atom.

The three unsaturated groups on the Group V atom in the surfactant optionally comprise alkenyl or alkynyl groups. Thus, for example, the surfactant can be a trisalkylphenyl-ethynylphosphine, e.g., trisalkylphenylethynylphosphine or tri(ethynylbenzene-hexyl)phosphine.

Compositions related to the methods are also a feature of the invention. One general class of embodiments provides a composition including a surfactant comprising a Group V atom substituted with three unsaturated groups and one or more precursors. The composition optionally also includes one or more nanostructures, e.g., Group III-V semiconductor nanostructures. The one or more precursors can, e.g., include a first precursor comprising a Group V atom and a second precursor comprising a Group III atom.

As for the embodiments above, the three unsaturated groups on the Group V atom in the surfactant optionally comprise alkenyl or alkynyl groups. Thus, for example, the surfactant can be a trisalkylphenylethynylphosphine, e.g., trisalkylphenylethynylphosphine or tri(ethynylbenzene-hexyl)phosphine.

Nanostructures

As noted, nanostructures (including, but not limited to, nanocrystals, substantially spherical nanocrystals, nanorods, branched nanostructures, or nanotetrapods) produced by any of the methods herein form another feature of the invention, as do devices, e.g., photovoltaic devices, including such nanostructures. Since the methods do not require the use of a non-semiconducting metal catalyst to initiate nanostructure growth, the resulting nanostructures are typically free of non-semiconducting (e.g., metallic) regions. Such absence of metallic regions in the nanostructures is desirable in many applications, e.g., when the nanostructures are to avoid charge recombination.

Thus, one general class of embodiments provides a nanostructure comprising a Group III-V semiconductor. The nanostructure is substantially free of metallic noble, Group Ib, Group IIb, Group Mb, and transition metal elements (e.g., such metallic elements are undetectable by a technique such as XRD). The nanostructure is optionally substantially free of any metallic metal element (e.g., free of metallic indium as compared to semiconducting indium phosphide).

In one class of embodiments, the nanostructure is a branched nanostructure or a nanostructure having an aspect ratio greater than about 1.2, and the nanostructure has a wurtzite crystal structure or a zinc blende-wurtzite mixed crystal structure. For example, in one class of embodiments, the nanostructure is a nanotetrapod; nanotetrapods typically have a zinc blende-wurtzite mixed crystal structure, with a zinc blende crystal structure in their central region and a wurtzite crystal structure in their arms. In another class of embodiments, the nanostructure is a nanorod having an aspect ratio greater than about 1.2, greater than about 1.5, greater than about 2, greater than about 3, or greater than about 5. Nanorods typically have a wurtzite crystal structure.

The Group III-V semiconductor typically comprises a first atom selected from the group consisting of N, P, As, Sb, and Bi and a second atom selected from the group consisting of B, Al, Ga, In, and Tl (see, e.g., the example materials listed above, e.g., InP and InAs).

Use of the novel precursors and/or surfactants of the invention can also produce nanostructures (of any size and/or shape, including, e.g., tetrahedral and substantially spherical nanocrystals as well as nanorods and branched nanostructures) that are substantially free of Si (since Si-containing precursors need not be used), substantially free of phosphonic acid, phosphinic acid, and/or carboxylic acid, and/or substantially free of tri-n-alkyl phosphines (e.g., TOP) and tri-n-alkyl phosphine oxides (e.g., TOPO) (since other surfactants can be used). Use of certain precursors described herein can, e.g., result in nanostructures having a sulfonic acid, or a boronic acid, or a deprotonated form or a condensate thereof, associated with a surface of the nanostructures. Similarly, use of certain precursors and/or surfactants described herein can, e.g., result in nanostructures having a carboxylic acid or a deprotonated form or a condensate thereof, and/or a surfactant comprising a Group V atom substituted with three unsaturated groups, associated with a surface of the nano structures.

Use of the methods and compositions of the invention can, e.g., decrease or prevent premature termination of nanostructure growth, resulting in larger nanostructures than were previously obtainable. Thus, for example, one general class of embodiments provides a nanostructure comprising a Group III-V semiconductor, the nanostructure being a tetrahedral nanostructure. In one class of embodiments, the nanostructure has an edge at least 10 nm in length (e.g., at least 12 nm, at least 15 nm, or at least 20 nm). All six edges are optionally at least 10 nm in length. The nanostructure can be, e.g., a nanocrystal, and can have a zinc blende crystal structure.

Essentially all of the features noted above apply to this embodiment as well, as relevant; e.g., for composition of the nanostructure. For example, the Group III-V semiconductor can include a first atom selected from the group consisting of N, P, As, Sb, and Bi and a second atom selected from the group consisting of B, Al, Ga, In, and Tl (e.g., InP and InAs). As for the embodiments described above, the nanostructure is optionally substantially free of metallic elements, Si, phosphonic acid, phosphinic acid, carboxylic acid, tri-n-alkyl phosphines and/or tri-n-alkyl phosphine oxides. Similarly, the nanostructure can have a carboxylic acid or a deprotonated form or a condensate thereof, and/or a surfactant comprising a Group V atom substituted with three unsaturated groups, associated with a surface of the nanostructure. The invention also includes a population of such nanostructures.

A device including a plurality of such nanostructures is also a feature of the invention, for example, a photovoltaic or other opto-electronic device. Packing of the tetrahedral nanostructures in such a device can, e.g., provide a favorable path for movement of electrons and/or holes through adjacent nanostructures disposed between opposing electrodes. Photovoltaic devices incorporating nanostructures are described, e.g., in U.S. patent application Ser. No. 10/778,009 entitled "Nanostructure and nanocomposite based compositions and photovoltaic devices" by Scher et al.

Compositions including nanostructures and one or more Group III precursor, Group V precursor, and/or surfactant of the invention are also a feature of the invention. Thus, one general class of embodiments provides a composition that includes one or more nanostructures (e.g., Group III-V semiconductor nanostructures) having a surfactant associated (covalently or non-covalently) with a surface thereof. The surfactant comprises a Group V atom substituted with three unsaturated groups, e.g., alkenyl or alkynyl groups. Essentially all of the features noted above apply to this embodiment as well, as relevant; e.g., for types and composition of nanostructures, types of surfactant, and the like. For example, the surfactant can be a trisalkylphenylethynylphosphine, e.g., trisalkylphenylethynylphosphine or tri(ethynylbenzene-hexyl)phosphine.

Another general class of embodiments provides a composition that includes one or more Group III-V semiconductor nanostructures and a first precursor of the invention. For example, the first precursor can comprise a Group V atom substituted with three unsaturated groups, a triacyl substituted Group V atom, a Group V atom substituted with three carboxamide groups, a triaryl substituted Group V atom, or a Group V atom substituted with three carboxylate moieties or with three phosphinate moieties, for example, any such precursors described herein. For example, the first precursor can be triallylphosphine, trivinylphosphine, tributadienylphosphine, trialkylethynylphosphine, trialkylethenylphosphine, tri(4-phenylethynyl)phosphine, trialkylphenylethynylphosphine, a triacylphosphine, tribenzoylphosphine, trialkylbenzoylphosphine, trihexylbenzoylphosphine, trialkoylphosphine, trihexoylphosphine, a tricarboxamide phosphine, N,N,N,N,N,N-hexaethylphosphine tricarboxamide, tribenzylphosphine, or tribenzylarsine. As another example, the first precursor can include a Group V atom substituted with three furyl or furfuryl groups; e.g., the first precursor can be tri-2-furylphosphine or tri-2-furfurylphosphine. As yet another example, the first precursor can be a phosphite ester. The composition optionally includes a second precursor, a first surfactant, a second surfactant, and/or a non-coordinating solvent. Essentially all of the features noted above apply to this embodiment as well, as relevant; e.g., for types and composition of nanostructures, second precursors, first and second surfactants, solvents, sacrificial oxide acceptors, and the like.

Yet another general class of embodiments provides a composition that includes one or more Group III-V semiconductor nanostructures and a second precursor of the invention. For example, the second precursor can comprise a Group III atom which is directly bonded to at least one oxygen atom; one or more phosphonate, phosphinate, and/or carboxylate moieties other than an acetate moiety bonded to a Group III atom; a group III metal oxide; a Group III alkoxy or aryloxy; or a Group III atom substituted with three unsaturated groups. Thus, the second precursor can be, e.g., indium phosphonate, indium carboxylate, indium tristearate, indium oxide, gallium oxide, indium phenoxy, triallyl indium, trivinyl indium, tributadiene indium, trialkylethynyl indium, trialkylethenyl indium, tri-4-phenylethynyl indium, trialkylphenylethynyl indium, tris-alpha-cyclohexanone indium (III), an indium tris-Cp compound, an indium tris-(substituted Cp) compound, tris-cyclopentadienyl indium(III) or tris(n-hexyl cyclopentadienyl) indium(III). The composition optionally includes a first precursor, a first surfactant, a second surfactant, and/or a non-coordinating solvent. Essentially all of the features noted above apply to this embodiment as well, as relevant; e.g., for types and composition of nanostructures, first precursors, first and second surfactants, solvents, sacrificial oxide acceptors, and the like.

EXAMPLES

The following sets forth a series of experiments that demonstrate growth of nanostructures at high temperature, synthesis and/or use of novel Group III and Group V precursors, use of an oxygen scavenger, and removal of a vapor byproduct, for example. It is understood that the examples and embodiments described herein are for illustrative purposes only and that various modifications or changes in light thereof will be suggested to persons skilled in the art and are to be included within the spirit and purview of this application and scope of the appended claims. Accordingly, the following examples are offered to illustrate, but not to limit, the claimed invention.

Example 1

Nanostructure Growth at High Temperature

A stock solution of $InCl_3$:THDP (stock 1) is made by heating 26.3% $InCl_3$ by weight in tri-n-hexadecyl phosphine (THDP) to 260° C. under argon for 2 hours. The stock solution is then cooled. 0.9 g of the stock solution is added to 8 g of THDP in a 3-neck flask. The mixture is heated to between 360° and 400° C. Upon reaching that temperature, a 50% by weight room temperature solution of $TMS_3P$ (tris(trimethylsilyl)phosphine) in TOP (stock 2) is injected into the mixture. The resulting InP nanocrystals are grown at between 350° and 400° C. for between 1 and 5 minutes. The reaction is then cooled to room temperature, and the nanocrystals are optionally washed or otherwise processed as desired.

Example 2

Nanostructure Synthesis Using Novel Group III and Group V Precursors

In a 3-neck flask, 4.0 g of TOP is heated to 250° C. (flask 1). In a separate schlenk flask, the following are combined: 240 mg $InCp_3$ (tris-cyclopentadienyl indium(III)), 268 mg tribenzoylphosphine, and 2.0 g TOP. This solution is stirred and vortexed, then injected into the TOP (flask 1) at between 250-200° C. The InP nanocrystals are grown at between 200 and 210° C. for 1 second to 5 minutes. The reaction is then cooled to room temperature, and the nanocrystals are optionally washed or otherwise processed as desired.

In a similar example, an acyl phosphine Group III precursor (e.g., tribenzoylphosphine) is reacted with a Group V precursor including In substituted with three unsaturated groups (e.g., $InCp_3$) in the presence of a non-coordinating solvent (e.g., dodecyl benzene) and a surfactant that is an unsaturated P derivative (e.g., tris(ethynylbenzene-pentyl) phosphine or tris(ethynylbenzene-hexyl)phosphine, which binds more weakly to the nanocrystal surface and reacts at a higher temperature than does the acyl phosphine precursor) to form InP nanocrystals. In another similar example, an acyl phosphine Group III precursor is reacted with a Group V precursor including In substituted with three unsaturated groups (e.g., $InCp_3$ or In-hexyl$Cp_3$) in the presence of a non-coordinating solvent, and the acyl phosphine Group III precursor also serves as a surfactant (see, e.g., Example 7 below). Use of the non-coordinating solvent instead of a tri-n-alkyl phosphine such as TOP can be advantageous, since TOP can coordinate indium more strongly than some unsaturated (e.g., acyl) phosphines and can thus inhibit InP growth, driving the reaction to formation of indium metal instead.

Example 3

By-Product Removal $InBr_3$ and TOP are combined in a 3 neck flask at a molar ratio of 12:1 P:In. The flask is heated to 360° C., which is near the refluxing temp of TOP. (In this example, the maximum reaction temperature, which is greater than 360° C., is determined by the refluxing of TOP.) After color change begins (indicating InP nanocrystal nucleation and growth), a syringe is used to remove vapor from the 3-neck flask. This vapor contains both TOP and bromooctane (the reaction by-product). By removing the bromooctane, the reaction to form nanocrystals increases to a faster rate than without removal of the vapor from the flask, resulting in an increased yield of nanocrystals in a given amount of time than without removal of the vapor.

Example 4

Synthesis of Tris-Cyclopentadienyl Indium

Synthesis of tris-cyclopentadienyl indium ($InCp_3$) is illustrated in FIG. 4 Panel A and described below. The synthesis is adapted from Beachley et al. (2002) Organometallics 21:4632.

General Methods

All manipulations were carried out with strict exclusion of air and moisture by using Schlenk technique under an inert atmosphere of argon. A MBraun glove box was used for storage and handling of $InCl_3$ and LiCp. THF and toluene were dried over activated 4 A Molecular Sieves and de-gassed by three freeze-pump-thaw cycles. THF-$d_8$ was dried over $CaH_2$ and after distillation was de-gassed with three freeze-pump-thaw cycles. NMR spectra were recorded with a Bruker FT NMR spectrometer at 400 MHz ($^1H$) or 100.6 MHz ($^{13}C$). Indium (III) chloride, ultra dry grade, was purchased from Alfa Aesar and used as received. LiCp was synthesized in house.

Procedure

In the glove box, indium (III) chloride (fwt 221.18, 3.25 g, 14.7 mmol) was transferred to a 250 mL Schlenk flask, and into a separate 250 mL Schlenk flask was transferred LiCp (fwt 72.03, 3.28 g, 45.5 mmol). About 60 mL of THF was added to the $InCl_3$ that formed a slowly dissolving slurry and 100 mL was added to the LiCp which formed a yellow-clear solution. Then the LiCp solution was added intermittently to the $InCl_3$ solution by cannula over 30 minutes with stirring. During the addition the reaction solution turned from yellow to yellow-orange. One hour after the addition was complete, the volatiles were removed by vacuum transfer to about 20 mtorr which rendered the product as an orange paste. Then 60 mL of toluene was added, and, after mixing thoroughly to insure the chunks of paste were broken up, the supernatant was transferred by filter tip cannula to a separate Schlenk flask. Again the volatiles were removed by vacuum transfer to a pressure of <20 mtorr. When the solvent was removed the product became a yellow microcrystalline powder (fwt 310.1, 3.67 g, 11.8 mmol, 80.6% yield). The product was stored in the glove box freezer at −35° C.

Analysis $^1H$ NMR (THF-$d_8$): δ 5.80 (s, $C_5H_5$). $^{13}C$ {$^1H$} NMR (THF-$d_8$): δ 109.0 (s, $C_5H_5$).

Example 5

Synthesis of Tris-Hexylcyclopentadienyl Indium from Dicyclopentadiene

Synthesis of tris-hexylcyclopentadienyl indium (fwt 562.58) from dicyclopentadiene via cyclopentadiene (fwt 66.10, d=0.797) and $C_5H_5(CH_2)_5CH_3$ (fwt 150.26) is illustrated in FIG. 4 Panel B and described below.

General Methods

All manipulations were carried out with strict exclusion of air and moisture by using Schlenk technique under an atmosphere of argon. An MBraun glove box was used for storage and handling of $InCl_3$ (fwt 221.18) and the product. Hexyl iodide was distilled before use and stored in a storage flask in the dark under argon over small pieces of copper metal. Indium (III) chloride, ultra dry 99.999%, was purchased from Alfa Aesar. Dicyclopentadiene was purchased from Aldrich. The $InCl_3$ was opened and stored in the glove box. THF and toluene were dried over activated 4 A Molecular Sieves and de-gassed by three freeze-pump-thaw cycles. NMR chemical shift data were recorded with a Bruker FT NMR at 400 MHz for $^1H$, 100 MHz for $^{13}C$ {$^1H$} and 162 MHz for $^{31}P$ {$^1H$} and are listed in ppm.

Cracking of Dicyclopentadiene

Dicyclopentadiene was monomerized by cracking and distillation under inert atmosphere at atmospheric pressure. The cyclopentadiene ($CH_6$) was distilled into a receiver cooled in a dry ice/ethanol bath. The vapor temperature was maintained between 40 and 60° C. during this distillation.

Synthesis of $C_5H_5(CH_2)_5CH_3$

To a 1 L, 1-neck Schlenk flask with a 250 mL addition funnel was added THF (400 mL) and $C_5H_6$ (20.0 mL, 25.1 g, 0.380 mol). The reaction solution was cooled in a dry ice/ethanol bath. Next, n-BuLi (106 mL of 2.5 M, 0.265 moles) was transferred to the addition funnel and added dropwise over 30 minutes. About 5 minutes after the addition was complete the dry ice/ethanol bath was removed and the reaction solution gradually warmed to room temperature. The turbidity of the reaction solution increased and became opaque upon warming to room temperature. Then the reaction flask was gently heated on a thermostat controlled bath at 30° C. for 30 minutes. Next the reaction solution was cooled in a dry ice/ethanol bath, and hexyl iodide (39.2 mL, 56.3 g, 0.265 moles) was dissolved in THF (50 mL) and added over 30 minutes to the reaction solution. About 10 minutes after the addition was complete, the dry ice/ethanol bath was removed and the solution warmed to room temperature. It was stirred at room temperature overnight. The reaction solution was poured into 200 mL of saturated $NH_4Cl$ and stirred for about 20 minutes. Then the reaction solution was washed into a reparatory funnel with 200 mL of hexane, and after phase separation the organic phase was washed with water 5×100 mL. The organic phase was then washed with brine 2×100 mL and dried over $Na_2SO_4$. The solvent was removed from the product by distillation at atmospheric pressure under argon using a pot temperature (i.e. oil bath temperature) of about 90° C. and a vapor temperature between 58 to 64° C. After removal of the solvent the product was distilled trap-to-trap with a liquid nitrogen cooled receiver at reduced pressure. The product was isolated as a clear colorless oil. The yield is about 50% or 19.2 g. The product was stored in the −35° C. freezer in the glove box.

Synthesis of In[C$_5$H$_4$(CH$_2$)$_5$CH$_3$]$_3$

The reaction was set up in a 250 mL, 1-neck Schlenk flask with a 100 mL addition funnel. On the Schlenk line THF (100 mL) and C$_5$H$_5$(CH$_2$)$_5$CH$_3$ (6.22 g, 41.4 mmol) were added. The reaction solution was cooled in a dry ice/ethanol bath and n-BuLi was added (16.5 mL, 2.5 M, 41.3 mmol) over 15 minutes. Then, 10 minutes after the addition was complete, the bath was removed and the reaction solution gradually warmed to room temperature. Into another 500 mL Schlenk flask InCl$_3$ (3.05 g, 13.8 mmol) was added in the glove box and on the Schlenk line the InCl$_3$ was diluted with THF (60 mL). The resulting solution was a slurry. About 30 minutes after reaching room temperature the Li anion solution was added to the InCl$_3$/THF slurry over about 5 minutes and stirred at room temperature for about 30 minutes. Next, the volatiles were removed by vacuum transfer. When the vacuum reached <50 mtorr the residue was extracted with hexane 3×40 ml, and transferred by filter tip cannula. The filter paper used was Whatman 5 with particle retention of >2.5 nm although Fisherbrand filter paper with particle retention of 1-5 nm has also been used. The organic filtrate was combined and the product isolated by removal of the volatiles by vacuum transfer. The product is a clear orange oil (3.72 g, 3.31 mmoles, 24.0% yield) and was stored in the glove box freezer at −35° C.

Analysis of C$_5$H$_5$(CH$_2$)$_5$CH$_3$ $^1$H NMR (toluene-d$_8$, δ): 0.90 (t, 3H, CH$_3$), 1.34 (m, 6H, (CH$_2$)$_3$), 1.55 (m, 2H, CH$_2$), 2.39 (m, 2H, CH$_2$), 2.88, 2.95 (m, 2H, ring CH$_2$), 6.01, 6.15, 6.25, 4.43 (m, 3H, ring CH). IR (cm$^{-1}$, diamond): 3066 w br, (CH diene), 2960 s, 2928 s, 2854 m (CH aliphatic). MALDI TOF MS (m/z): 151.3 (M+H).

Analysis of In[C$_5$H$_4$(CH$_2$)$_5$CH$_3$]$_3$ $^1$H NMR (toluene-d$_8$): δ 0.90 (s, 3H, CH$_3$), 1.30 (m, 6H, (CH$_2$)$_3$), 1.70 (m, 2H, CH$_2$), 2.60 (m, 2H, CH$_2$), 5.60, 6.10 (m, 2H, ring CH). $^{13}$C {$^1$H} NMR (toluene-d$_8$, δ): 14.3, 23.2, 30.0, 30.4, 32.2, 32.3 (s, (CH2)5CH3), 101.0, 112.4, 137.4 (s br, CH). IR (cm$^{-1}$, diamond): 3062 w br (CH Cp), 2960 s, 2928 s, 2854 m (CH aliphatic).

Example 6

Synthesis of P[COC$_6$H$_4$(CH$_2$)$_6$CH$_3$]$_3$

Synthesis of P[COC$_6$H$_4$(CH$_2$)$_6$CH$_3$]$_3$ (fwt 640.87) from Cl(CO)C$_6$H$_4$(CH$_2$)$_6$CH$_3$ (fwt 238.75, d=0.978) is illustrated in FIG. 4 Panel C and described below. The synthesis is adapted from Plazek and Tyka (1959) Roczniki Chem. 33:549. It is worth noting that As precursors can be made (and used in nanostructure synthesis reactions) analogously to the P precursor described herein.

General Methods

All manipulations were carried out with strict exclusion of air and moisture by using Schlenk technique under an atmosphere of dry nitrogen. Pyridine, THF, toluene and toluene-d$_8$ were dried over activated 4A Molecular Sieves and de-gassed by three freeze-pump-thaw cycles. Phosphine gas was purchased from Matheson Trigas and used without further purification. The acid chloride, Cl(CO)C$_6$H$_4$(CH$_2$)$_6$CH$_3$, was distilled before use (bp=100° C. at 0.1 torr) and stored in a Schlenk storage flask under argon. Water (used in the work up) was degassed with bubbling nitrogen for >30 minutes. NMR chemical shift data were recorded with a Bruker FT NMR at 400 MHz for $^1$H, 100 MHz for $^{13}$C {$^1$H} and 162 MHz for $^{31}$P {$^1$H} and are listed in ppm.

Synthesis of P[COC$_6$H$_4$(CH$_2$)$_6$CH$_3$]$_3$

This reaction was performed in a 1 L storage flask that has a Teflon stopper to seal the flask and Schlenk line connection attachment above the valve. The 1 L storage flask was connected to the Schlenk line and phosphine tank regulator using a 'Y' fitting on the vacuum tubing. After evacuation and back flush cycles, Cl(CO)C$_6$H$_4$(CH$_2$)$_6$CH$_3$ (12.0 mL, 11.98 g, 50.1 mmol) was added to the storage flask followed by pyridine (40.6 mL, 39.7 g, 501 mmol). The solution was frozen with liquid nitrogen and evacuated to <50 mtorr. After maintaining vacuum for about 1 minute, the valve to the storage flask was closed and the hoses back flushed with argon. The reaction flask was removed from the liquid nitrogen and warmed to room temperature (valve still closed) behind a blast shield. When the solution had warmed to room temperature, the hoses were evacuated to <50 mtorr and the valve on the Schlenk line was closed. Next, the valve to the storage flask was opened and about 0.7 atmosphere of phosphine gas was released into the system using the phosphine tank regulator. The valve on the storage flask was then closed. The phosphine gas remaining in the hoses was decomposed by release into a bleach bath. The reaction flask was stirred at room temperature for three days.

The storage flask and 1 L Schlenk flask (with new septa) were attached to the Schlenk line using a 'Y' fitting on the vacuum tubing. The hoses and Schlenk flask were evacuated to a vacuum of <50 mtorr and the valve to the Schlenk line was closed. Next, (behind a blast shield) the Schlenk flask was cooled in liquid nitrogen and the valve to the storage/reaction flask was opened. The excess phosphine gas was condensed in the Schlenk flask. The valve to the storage flask was closed. The Schlenk flask was removed from the liquid nitrogen and the flask warmed to room temperature behind a blast shield. When the Schlenk flask had warmed to room temperature, the phosphine gas was decomposed by release into a bleach bath. The storage flask (containing the reaction solution) was re-connected to the Schlenk line and the volatiles removed by vacuum transfer to <200 mtorr. The residue was extracted with toluene (2×20 mL and 1×10 mL) and the filtrate was transferred by filter tip cannula to a 250 mL Schlenk flask. The filtrate was washed with degassed water (3×20 mL) and the volatiles removed by vacuum transfer to produce the crude product as a viscous, clear orange oil. A high vacuum was applied at <40 mtorr while the flask containing the product was gently heated in a bath to 30° C. for >12 h. The product is a waxy orange solid (8.62 g, 13.5 mmoles, 80.5% yield). It is worth noting that the product reacts quickly with oxygen but slowly with water and water is used to wash the product at the end of the work-up. Therefore, immediately after the majority of the volatiles are removed by vacuum transfer in the work-up a high vacuum of <40 mtorr is to be applied to the product. Although the solution is viscous, traces of water are removed that would react with the product and cause decomposition.

Analysis of P[COC$_6$H$_4$(CH$_2$)$_6$CH$_3$]$_3$ $^1$H NMR (toluene-d$_8$, δ): 0.90 (t, 3H, CH$_3$), 1.19, 1.28 (m, 8H, CH$_2$), 1.38 (m, 2H, CH$_2$), 2.35 (m, 2H, CH$_2$), 6.93, 8.01 (d, 4H, CH). $^{13}$C {$^1$H} NMR (toluene-d$_8$, δ): 14.3, 23.1, 29.6, 19.7, 31.2, 32.2, 36.3 (s, (CH$_2$)$_6$CH$_3$), 139.0, 130.8, 129.3 (d, Ph), 128.9 (s, Ph), 204.9 (d, C=O). $^{31}$P {$^1$H} NMR (toluene-d$_8$, δ): 53 (s, phosphine). IR (cm$^{-1}$, diamond): 1643 s, 1606 s (C=O), 3030 w (CH aromatic), 2956 sh, 2928 s, 2854 m (CH aliphatic). MALDI TOF MS (m/z): 641.5 (M+H).

Example 7

Synthesis of a Cyclopentadienyl Indium-Acyl Phosphine Complex and Preparation of Indium Phosphide Nanocrystals General Methods All manipulations were carried out with strict exclusion of air and moisture by using Schlenk technique under an inert atmosphere of argon. Also, reagents were stored in a glove box until use. An M Braun glove box was used for storage and handling of $In(C_5H_5)_3$ and $P[COC_6H_4(CH_2)_6CH_3]_3$. Toluene was dried over activated 4 Angstrom Molecular Sieves and de-gassed by three freeze-pump-thaw cycles. Tetradecylbenzene was distilled with vapor temperature of 150 to 160° C. and pressure of <70 mtorr. $P[COC_6H_4(CH_2)_6CH_3]_3$ is an orange waxy solid and was stored in the glove box freezer at −35° C. NMR chemical shift data are listed in ppm and were recorded with a Bruker FT NMR at 400 MHz for $^1H$ 100 MHz for $^{13}C$ $\{^1H\}$ and 162 MHz for $^{31}P$ $\{^1H\}$.

Spectroscopic Evidence for Indium-Phosphine Complex Formation

Equal molar amounts $In(C_5H_5)_3$ and $P[COC_6H_4(CH_2)_6CH_3]_3$ (0.037 mmol) were combined in an NMR tube and dissolved in toluene-$d_8$ in the glove box. Analysis by $^{31}P$ $\{^1H\}$ NMR for $P[COC_6H_4(CH_2)_6CH_3]_3$ was 53.0 ppm while for the 'In—P' complex was 70.8 ppm under the same conditions. Formation of the In—P complex is schematically illustrated in FIG. 5 Panel A.

Synthesis of a Preformed Indium-Phosphide Precursor in Tetradecylbenzene

To a 50 mL Schlenk flask in the glove box was added $In(C_5H_5)_3$ (fwt 310.1, 0.249 g, 0.80 mmol) and $P[COC_6H_4(CH_2)_6CH_3]_3$ (fwt 640.87, 0.517 g, 0.80 mmol). In the glove box toluene (4.0 mL) was added and the mixture stirred for a few minutes at room temperature. To the resulting red solution tetradecylbenzene (2.0 mL) was added. Then on the Schlenk line toluene was removed by vacuum transfer while the solution was gently heated at 30° C. until the pressure reached <50 mtorr for about 5 minutes duration. Preformation of the precursor complex is schematically illustrated in FIG. 5 Panel B.

Synthesis of Indium-Phosphide from the Preformed Precursor

Synthesis of InP nanocrystals from the preformed precursor is schematically illustrated in FIG. 5 Panel C. To a 25-mL, 3-neck round bottom flask equipped with an air reflux condenser was added tetradecylbenzene (7.0 mL) inside the glovebox. Then, on the vacuum line, the mixture was heated to 360° C. with the temperature control set to 380° C. to maintain a constant reflux. The reaction was initiated by rapid injection of the solution of $In(C_5H_5)_3$ and $P[COC_6H_4(CH_2)_6CH_3]_3$ in tetradecylbenzene. This instantly turned the reaction solution opaque black. About 5 minutes later, an orange solution of $P[COC_6H_4(CH_2)_6CH_3]_3$ (0.518 g, 0.80 mmol) in tetradecylbenzene (3.0 mL) was added by syringe over about 5 min. FIG. 5 Panel D shows the reaction temperature profile. About 4 minutes later the reaction was stopped by removal of the heat from the reaction flask. When the solution temperature had dropped to about 60° C., toluene (2.0 mL) was added. Then the reaction solution was transferred into the glove box for purification. Also a small amount of solid material was collected from the air reflux condenser for analysis by mass spec (FIG. 5 Panel E). The ketone with fwt 268.4 (shown at the bottom right of FIG. 5 Panel C) was detected, suggesting simple elimination of ligands from the preformed In—P precursor in route to forming the nanocrystal.

Indium Phosphide Nanocrystal Purification

To one quarter of the reaction solution was added isopropanol (4.0 mL) and methanol (1.0 mL). The solution was mixed with a vortex mixer and divided into two vials. To each portion was added methanol (1.0 mL), and the solutions were mixed again with the vortex mixer and separated by centrifugation into two phases. The bottom phase consisted of thick black oil. The supernatant was decanted and the black oil purified further. To the oil was added isopropanol (4.0 mL), the solutions were mixed with a vortex mixer, and solids were separated by centrifugation. Decantation produced a black oily solid that was purified further. Again, to the precipitate was added methanol (2.0 mL), the solution was mixed with a vortex mixer and the solids separated by centrifugation. After decantation a black solid was obtained that was analyzed by TEM (FIG. 5 Panel F) and XRD (FIG. 5 Panel G. TEM samples were prepared by dissolving part of the black solid precipitate in a dilute solution of toluene and evaporating it onto an amorphous carbon (<10 nm thick) coated copper mesh TEM grid. They were then measured on a FEI Tecnai 12 TEM with a Twin objective lens at 120 kV. For Powder X-ray diffraction (XRD), samples were dried to a powder on a quartz plate and run in a Bruker-AXS Discover D8 diffractometer with a general area detector diffraction system (GADDS). The x-ray source was Cu Kα radiation with a wavelength of 1.540598 Å. Theoretical lines were calculated using standard unit cell dimensions.

Example 8

Synthesis of Indium Phosphide Nanocrystals from Tris-Hexylcyclopentadienyl Indium and $P[COC_6H_4(CH_2)_6CH_3]_3$ General Methods All manipulations were carried out with strict exclusion of air and moisture by using Schlenk technique under an inert atmosphere of argon. Also, reagents were stored in a glove box until use. An M Braun glove box was used for storage and handling of $In[C_5H_4(CH_2)_5CH_3]_3$ and $P[COC_6H_4(CH_2)_6CH_3]_3$. Toluene was dried over activated 4 Angstrom Molecular Sieves and de-gassed by three freeze-pump-thaw cycles. Hexadecylbenzene was distilled with a vapor temperature between 130 and 140° C. and pressure of <20 mtorr. Triphenylphosphine was degassed briefly in the glove box antechamber. Stearic acid was dried and degassed in a desiccator containing $P_2O_5$ under static vacuum for more than 12 hours. $In[C_5H_4(CH_2)_5CH_3]_3$ is an orange oil and $P[COC_6H_4(CH_2)_6CH_3]_3$ is an orange waxy solid. Both were stored in the glove box freezer at −35° C. NMR chemical shift data are listed in ppm and were recorded with a Bruker FT NMR at 400 MHz for $^1H$ 100 MHz for $^{13}C$ $\{^1H\}$ and 162 MHz for $^{31}P$ $\{^1H\}$.

Synthesis of a Preformed Indium-Phosphide Precursor Complex in Hexadecylbenzene

A Schlenk flask was charged with $In[C_5H_4(CH_2)_5CH_3]_3$ (fwt 562.58, 0.2248 g, 0.40 mmol) and $P[COC_6H_4(CH_2)_6CH_3]_3$ (fwt 640.87, 0.2565 g, 0.40 mmol) inside the glove box. Toluene (4.0 mL) was added and the mixture stirred at room temperature for a few minutes while a red homogeneous solution formed. Hexadecylbenzene (2.0 mL) was added and the solution stirred at room temperature for 30 min. Then the toluene was removed by vacuum transfer while the solution was gently heated at 30° C. until the pressure reached <50 mtorr for a duration of about 5 minutes. Formation of the In—P precursor complex is schematically illustrated in FIG. 6 Panel A. Additionally, two Schlenk flasks were also used to prepare two other solutions. In the glove box, one of the Schlenk flasks was charged with $P[COC_6H_4(CH_2)_6CH_3]_3$ (0.2574 g, 0.4 mmol) followed by toluene (4.0 mL) and after mixing briefly hexadecylbenzene (2.0 mL). To the other Schlenk flask was added $In[C_5H_4(CH_2)_5CH_3]_3$ (0.2264 g, 0.4 mmol) followed by toluene (4.0 mL) and after mixing hexadecylbenzene (2.0 mL). Then the toluene was removed from both solutions by vacuum transfer. The solutions were heated at 30° C. until the pressure reached <50 mtorr for about 5 minutes duration.

Synthesis of Indium Phosphide Nanocrystals

To a 25-mL, 3-neck round bottom flask equipped with an air reflux condenser was added triphenylphosphine (0.1044 g, 0.40 mmol), stearic acid (0.1135 g, 0.40 mmol) and hexadecylbenzene (7.0 mL) inside the glove box. (Without limitation to any particular mechanism, the triphenylphosphine can act as a sacrificial oxide acceptor during the nanocrystal synthesis reaction, and the stearic acid can act as a surfactant and/or can attack and remove any $COC_6H_4(CH_2)_6CH_3$ substituents remaining on the surface of the growing nanocrystal.) On the Schlenk line the reaction solution was heated to 385° C. under Argon. Then the reaction was initiated by addition of the complex of $In[C_5H_4(CH_2)_5CH_3]_3$ and $P[COC_6H_4(CH_2)_6CH_3]_3$ in hexadecylbenzene. Upon addition the reaction solution instantly turned opaque black. Then immediately following that addition the temperature control was reset to 330° C. About 5 min later an orange solution of $P[COC_6H_4(CH_2)_6CH_3]_3$ in hexadecylbenzene was added by a syringe pump over a period of 5 min. About 10 min after the initial injection, the addition of $P[COC_6H_4(CH_2)_6CH_3]_3$ was complete and the addition of $In[C_5H_4(CH_2)_5CH_3]_3$ in hexadecylbenzene was started. That addition occurred over a period of about 10 minutes. Next, heating at 330° C. was continued for 40 minutes longer before the heat source on the reaction flask was removed to stop the reaction. The total reaction time was about 60 min. The reaction profile is shown in FIG. 6 Panel B. As the temperature of the reaction solution reached 60° C., toluene (2.0 mL) was added and the reaction solution was taken into the glove box for purification.

Indium Phosphide Nanocrystal Purification

The reaction solution was divided into four equal portions and separated by centrifugation. The top phase was retained for further purification and the precipitate was discarded. One of these four portions was purified by addition of isopropanol (3.0 mL) and methanol (1.0 mL) and the solution mixed with a vortex mixer and separated by centrifugation. After decantation the black bottom phase was dissolved in isopropanol (2.0 mL) and methanol (2.0) mL. Next, the solution was mixed with a vortex mixer and separated by centrifugation leaving a black bottom phase that was purified further after decantation. Methanol (4.0 mL) was added and the solution was mixed with a vortex mixer and separated by centrifugation. After decantation the bottom phase was added to isopropanol (4.0 mL) and the solution mixed with a vortex mixer and separated by centrifugation leaving a solid bottom phase. After decantation the bottom phase was added to toluene (0.5 mL) and isopropanol (4.0 mL) and the solution was mixed with a vortex mixer and separated by centrifugation. After decantation the solid bottom phase was added to toluene (0.5 mL) and methanol (4.0 mL) and the solution was mixed with a vortex mixer and separated by centrifugation. After decantation the solid bottom phase was added to toluene (0.5 mL) and methanol (4.0 mL) and the solution was mixed with a vortex mixer and separated by centrifugation. After decantation the black solid material was analyzed by TEM (FIG. 6 Panels C and D), XRD (FIG. 6 Panel E) and UV-Vis spectroscopy (FIG. 6 Panel F). TEM and XRD were performed basically as described in Example 7.

Example 9

Size and Shape Control of InP Nanocrystal Synthesis

Except as indicated, nanocrystals were produced basically as described in Example 8. Indium phosphide nanocrystals were synthesized from tris-hexylcyclopentadienyl indium (also indicated as $In[C_5H_4(CH_2)_5CH_3]_3$ or $In(CpC_6H_{13})_3$) and $P[COC_6H_4(CH_2)_6CH_3]_3$ (also indicated as $P(COPhC_7H_{15})_3$) as illustrated in the reaction profile shown in FIG. 7 Panel A. 0.4 mmol of $[In(CpC_6H_{13})_3$—$P(COC_6H_4C_7H_{15})_3]$ in 2.0 mL hexadecylbenzene (HDB) was injected into a mixture containing 0.4 mmol triphenylphosphine ($PPh_3$), 0.4 mmol stearic acid, and 7.0 ml HDB. About five minutes later, 0.4 mmol of $[In(CpC_6H_{13})_3$—$P(COC_6H_4C_7H_{15})_3]$ in 2.0 mL HDB was added over 10 minutes.

Dynamic light scattering data showing the size of the resulting InP zinc blende tetrahedral nanostructures are shown in FIG. 7 Panel B. The UV-visible absorption spectrum of the nanocrystals is shown in FIG. 7 Panel C; the InP band edge is indicated by an arrow. Transmission electron micrographs of the tetrahedral nanocrystals are shown in FIG. 7 Panel D. XRD analysis (FIG. 7 Panel E) shows a clean indium phosphide zinc blende pattern (theoretical lines are indicated by squares).

Adjusting precursor complex concentrations in the precursor addition sequence can produce larger tetrahedra, e.g., as follows. Indium phosphide nanocrystals were synthesized as illustrated in the reaction profile shown in FIG. 7 Panel F. 0.2 mmol of $[In(CpC_6H_{13})_3$—$P(COC_6H_4C_7H_{15})_3]$ in 2.0 mL hexadecylbenzene (HDB) was injected into a mixture containing 0.4 mmol triphenylphosphine ($PPh_3$), 0.4 mmol stearic acid, and 7.0 ml HDB. About five minutes later, 0.6 mmol of $[In(CpC_6H_{13})_3$—$P(COC_6H_4C_7H_{15})_3]$ in 2.0 mL HDB was added over 10 minutes. The UV-visible absorption spectrum of the resulting nanocrystals is shown in FIG. 7 Panel G. The spectrum shows more absorption near 800 nm, indicating larger size InP nanocrystals (arrow). TEM (FIG. 7 Panel H) confirms the increased size of the InP tetrahedra. Theoretical and experimental InP zinc blend XRD patterns are shown in FIG. 7 Panel I.

Example 10

Figure 8C:
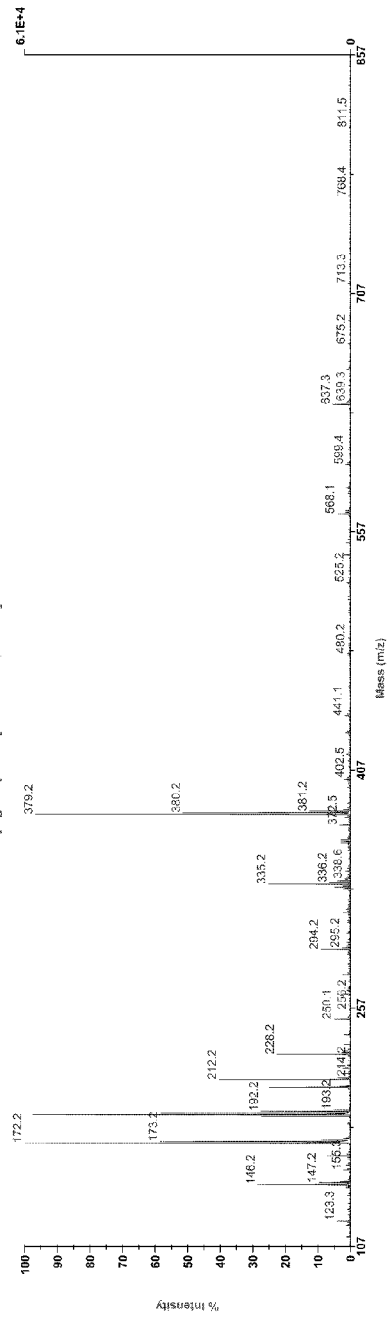
FIG. 8 Panels A and B schematically depict triphenylphosphine acting as an oxide acceptor in a nanostructure synthesis reaction. Panel C presents a MALDI TOF mass spec background scan showing matrix peaks. Panels D and E presents results of mass spec analysis of reaction mixtures, indicating the presence of triphenylphosphine oxide.
Figure 8D:
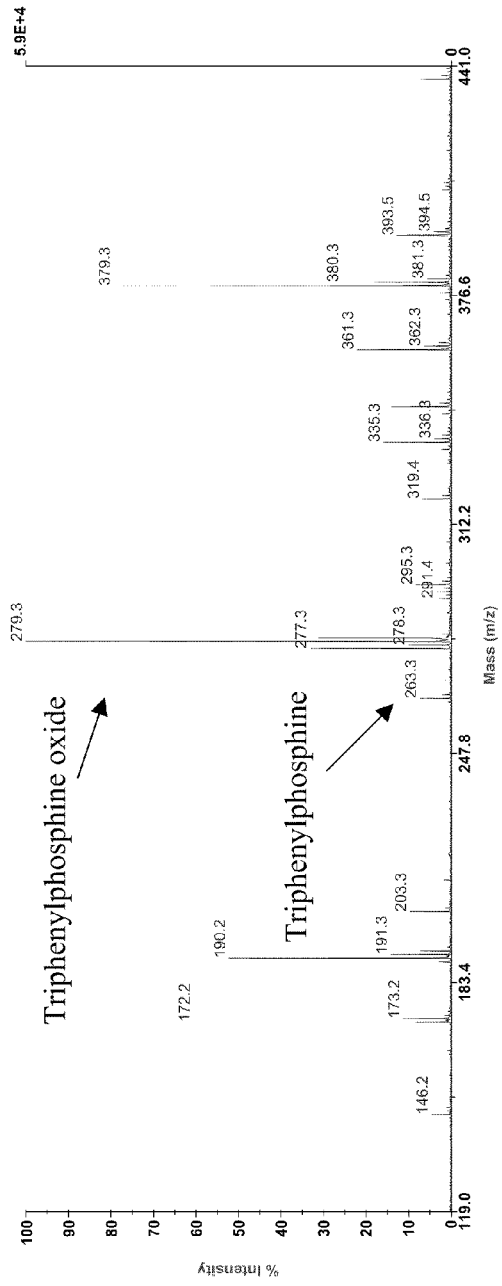
Figure 8E:
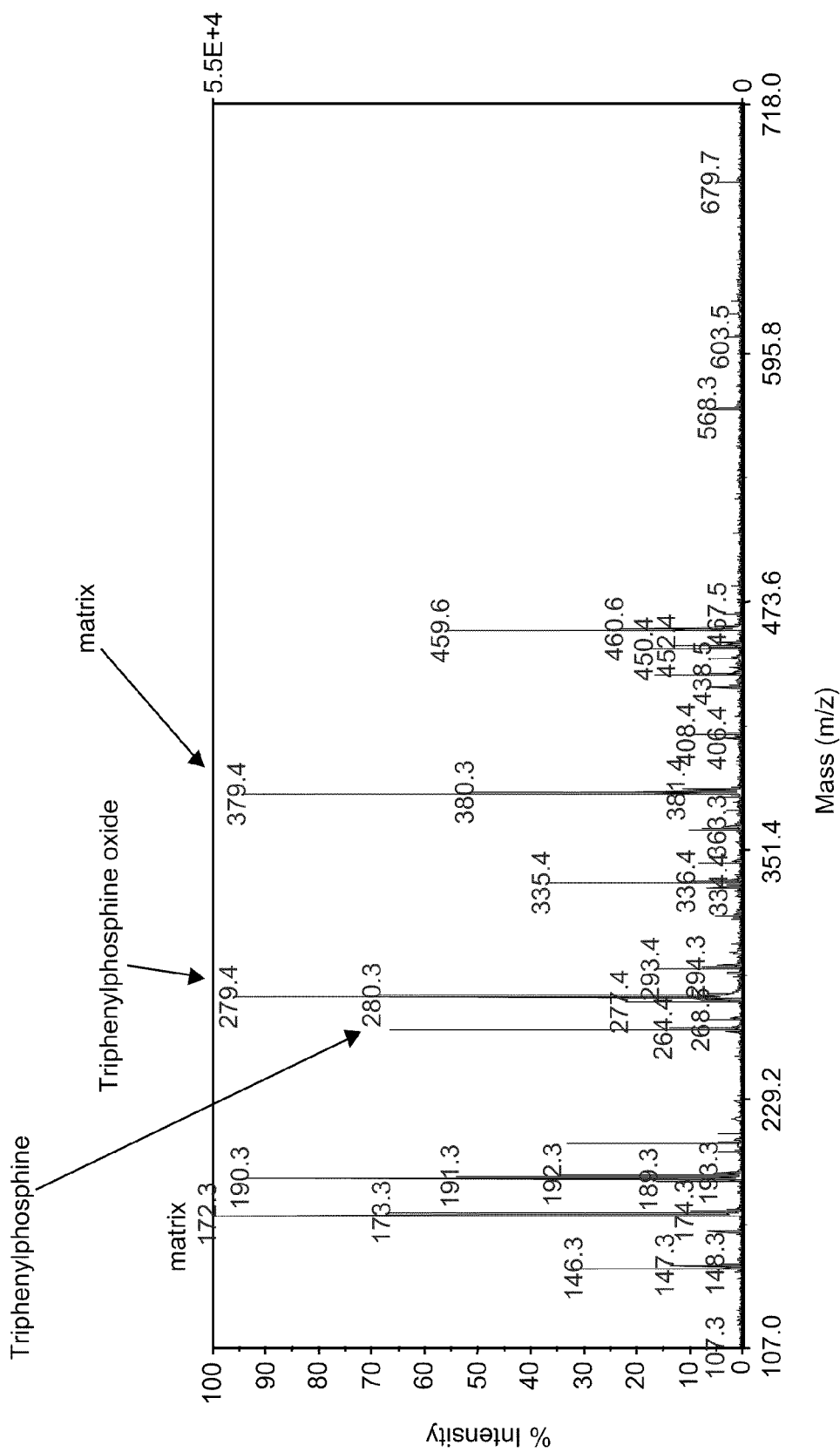

Triphenylphosphine Acts as an Oxygen Scavenger in Nanostructure Synthesis Reactions Triphenylphosphine is known as an oxide acceptor in reactions such as the Mitsunobu reaction (see Nagasawa and Mitsunobu (1981) Bull. Chem. Soc. Japan 54:2223). We have demonstrated that it can also act as an oxide acceptor in nanostructure synthesis reactions. An example reaction is schematically illustrated in FIG. 8 Panels A and B. MALDI TOF mass spec analysis of InP nanocrystal reaction mixtures (FIG. 8 Panels D and E; background matrix scan is shown in Panel C) reveals the presence of triphenylphosphine oxide, supporting the hypothesis that triphenylphosphine acts as an oxygen scavenger in nanocrystal synthesis reactions.

Example 11

Synthesis of Indium Tristearate and Use in InP Nanostructure Synthesis

Figure 9A:
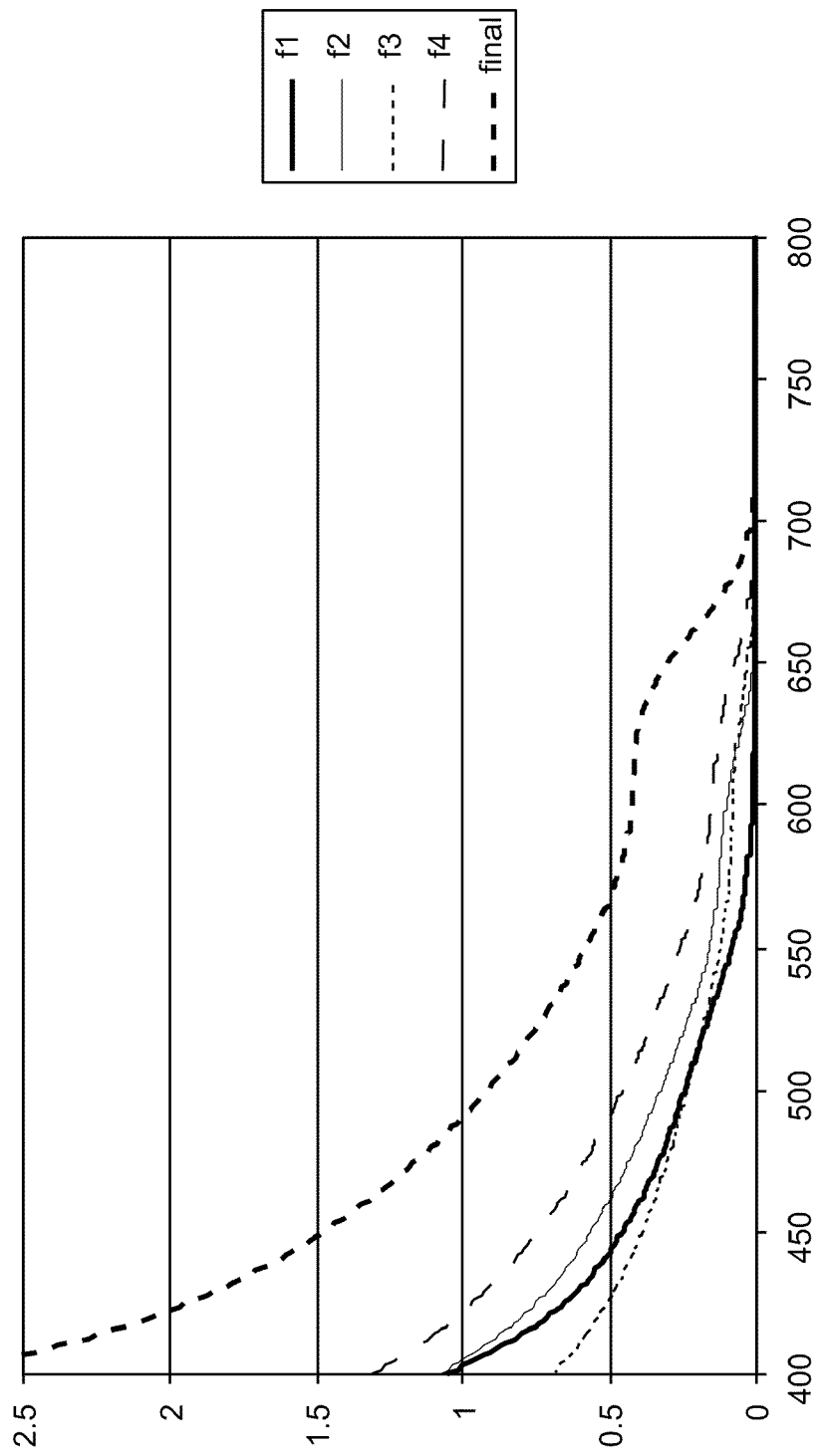
FIG. 9 Panel A shows a UV-visible absorption spectrum of InP nanocrystals. Panel B presents results of XRD analysis of the nanocrystals.
Figure 9B:
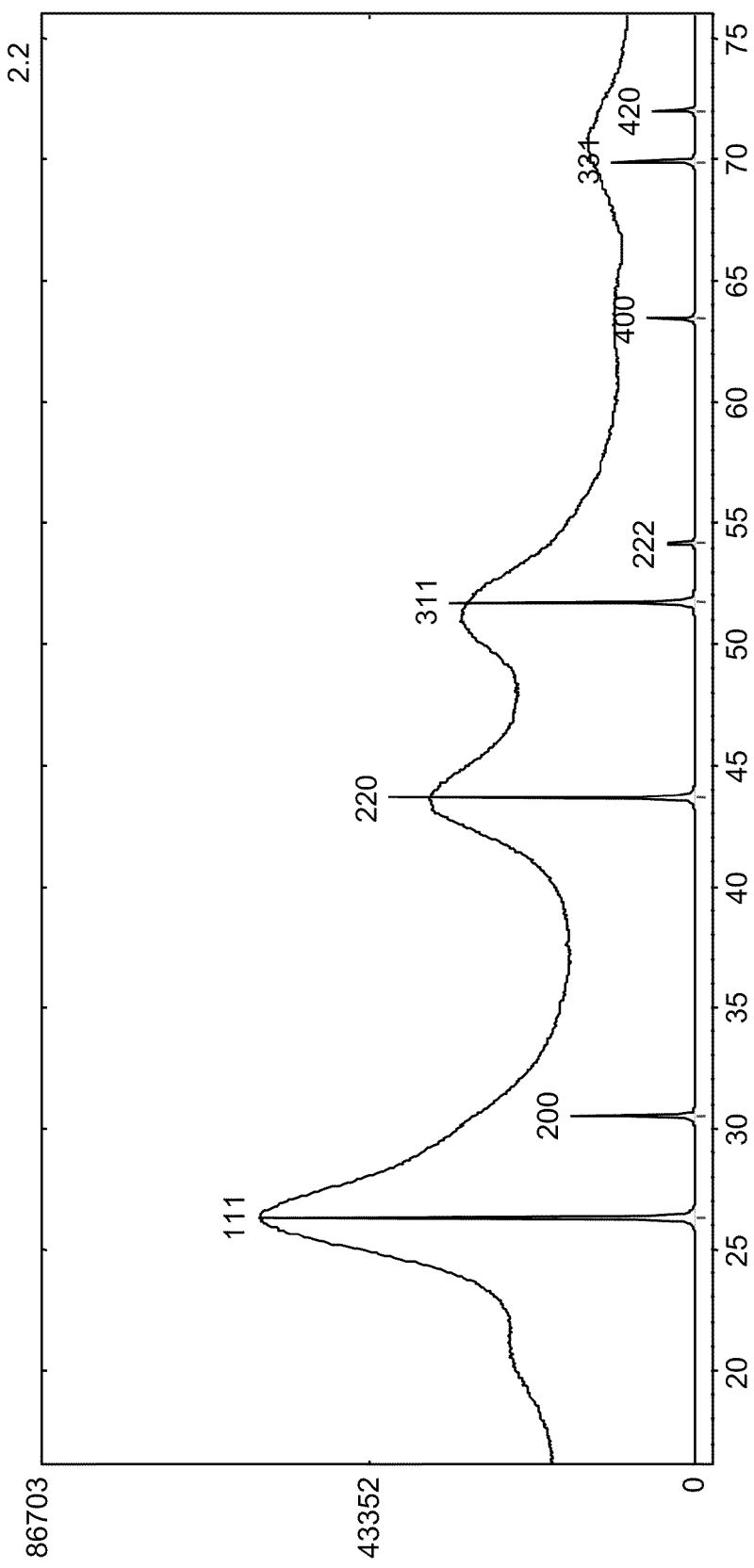

Trimethyl indium was reacted with three equivalents of stearic acid, yielding indium tristearate (and three equivalents of methane, which were evaporated). Two equivalents of $(TMS)_3P$ were added to react with the indium tristearate. The solvent was dodecylbenzene, and stearic acid served as the surfactant. The resulting InP nanocrystals were analyzed by UV-visible spectroscopy (FIG. 9 Panel A; f1-final indicate successive fractions removed from the growth solution over the course of the synthesis) and XRD (FIG. 9 Panel B).

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A method for production of Group III-V semiconductor nanostructures, the method comprising:
providing one or more surfactants;
providing a first precursor comprising a Group V atom;
providing a second precursor comprising a tricarboxylate substituted Group III atom;
heating the one or more surfactants to a first temperature;
contacting the first and second precursors and the one or more heated surfactants, whereby the first and second precursors react to form nuclei capable of nucleating nanostructure growth; and,
maintaining the first and second precursors, the one or more surfactants, and the nuclei at a second temperature, the second temperature permitting growth of the nuclei to produce the nanostructures, whereby the first and second precursors react to grow the nanostructures from the nuclei.

2. The method of claim 1, wherein the first temperature is at least 300° C.

3. The method of claim 1, wherein the second temperature is at least 250° C.

4. The method of claim 1, wherein the first temperature is greater than the second temperature by about 40-80° C., about 20-40° C., about 10-20° C., about 5-10° C., or about 0-5° C.

5. The method of claim 1, wherein each of the one or more surfactants has a boiling point that is greater than the first and second temperatures.

6. The method of claim 1, wherein the one or more surfactants comprise at least a second surfactant.

7. The method of claim 6, wherein the second surfactant is an alkyl amine, or wherein the second surfactant is a phosphonic acid, a phosphinic acid, a carboxylic acid, a boronic acid, or a sulfonic acid, or a deprotonated form or a condensate thereof.

8. The method of claim 7, wherein the second surfactant is a C2-30 alkylphosphonic acid, a C2-30 bialkylphosphinic acid, or a C2-30 alkylcarboxylic acid.

9. The method of claim 1, wherein the one or more surfactants comprise a first surfactant and a second surfactant, whereby the shape of the nanostructures produced is capable of being controlled by adjusting the ratio of the first and second surfactants.

10. The method of claim 9, wherein the ratio of the first and second surfactants is adjusted to produce substantially spherical nanocrystals.

11. The method of claim 9, wherein the ratio of the first and second surfactants is adjusted to produce one or more of: nanorods, branched nanostructures, or nanotetrapods.

12. The method of claim 1, wherein reacting the first and second precursors comprises reacting the first and second precursors in the presence of a second surfactant, whereby the shape of the nanostructures produced is capable of being controlled by adjusting the ratio of the second surfactant and the first or second precursor.

13. The method of claim 12, wherein the ratio of the second surfactant and the first or second precursor is adjusted to produce substantially spherical nanocrystals.

14. The method of claim 12, wherein the ratio of the second surfactant and the first or second precursor is adjusted to produce one or more of: nanorods, branched nanostructures, or nanotetrapods.

15. The method of claim 1, wherein the ratio of the first and second precursors is adjusted to control the shape of the nanostructures produced.

16. The method of claim 15, wherein the ratio of the first and second precursors is adjusted to produce substantially spherical nanocrystals.

17. The method of claim 15, wherein the ratio of the first and second precursors is adjusted to produce one or more of: nanorods, branched nanostructures, or nanotetrapods.

18. The method of claim 1, wherein the Group V atom is selected from the group consisting of N, P, As, Sb, and Bi.

19. The method of claim 1, wherein the Group III atom is selected from the group consisting of: B, Al, Ga, In, and Tl.

20. The method of claim 1, wherein the Group III-V semiconductor nanostructures comprise InN, InP, InAs, InSb, GaN, GaP, GaAs, GaSb, AlN, AlP, AlAs, or AlSb.

21. The method of claim 1, wherein the nanostructures comprise one or more of: nanocrystals, substantially spherical nanocrystals, nanorods, branched nanostructures, or nanotetrapods.

22. A nanostructure, nanocrystal, substantially spherical nanocrystal, nanorod, branched nanostructure, or nanotetrapod produced by the method of claim 1.

23. The method of claim 1, wherein the one or more surfactants comprise at least a first surfactant.

24. The method of claim 23, wherein the first surfactant is an alkyl amine, a monoalkyl amine, or a bialkyl amine.

25. The method of claim 23, wherein the first surfactant is a tri-n-alkyl phosphine or a tri-n-alkyl phosphine oxide.

26. The method of claim 25, wherein the first surfactant is a C12-C30 tri-n-alkyl phosphine.

27. The method of claim 26, wherein the first surfactant is tri-n-dodecyl phosphine or tri-n-hexadecyl phosphine.

28. The method of claim 1, wherein the first temperature is at least 360° C. and/or the second temperature is at least 300° C.

29. The method of claim 1, wherein the second precursor comprises a tristearate substituted Group III atom.

30. The method of claim 1, wherein the second precursor is an indium tricarboxylate.

31. The method of claim 1, wherein the second precursor is an indium tristearate.

32. The method of claim 31, wherein the first precursor comprises a trialkyl substituted Group V atom.

33. A composition, comprising: one or more surfactants, a first precursor comprising a Group V atom, and a second precursor comprising a tricarboxylate substituted Group III atom.

* * * * *